US007208528B1

(12) United States Patent
Vermeulin et al.

(10) Patent No.: US 7,208,528 B1
(45) Date of Patent: *Apr. 24, 2007

(54) POLYAMINE ANALOGUES AS THERAPEUTIC AND DIAGNOSTIC AGENTS

(75) Inventors: Nicolaas M. J. Vermeulin, Woodinville, WA (US); Christine L. O'Day, Mountlake Terrace, WA (US); Heather K. Webb, Seattle, WA (US); Mark R. Burns, Shoreline, WA (US); Donald E. Bergstrom, West Lafayette, IN (US)

(73) Assignee: MediQuest Therapeutics, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/396,523

(22) Filed: Sep. 15, 1999

Related U.S. Application Data

(63) Continuation-in-part of application No. 09/341,400, filed on Sep. 3, 1999, now Pat. No. 6,172,261, which is a continuation-in-part of application No. PCT/US98/14896, filed on Jul. 15, 1998.

(60) Provisional application No. 60/085,538, filed on May 15, 1998, provisional application No. 60/065,728, filed on Nov. 14, 1997, provisional application No. 60/052,586, filed on Jul. 15, 1997.

(51) Int. Cl.
*A61K 31/47* (2006.01)
*A61K 31/425* (2006.01)
*A61K 31/42* (2006.01)
*A61K 31/17* (2006.01)
*A61K 31/16* (2006.01)

(52) U.S. Cl. .............. 514/626; 514/311; 514/365; 514/378; 514/423; 514/445; 514/471; 514/481; 514/596; 514/602; 514/603; 514/616; 514/617; 514/625; 544/144; 548/200; 548/248; 548/375.1; 548/536; 549/479; 560/157; 564/197; 564/48; 564/80; 564/83; 564/84; 564/86; 564/161; 564/180

(58) Field of Classification Search ........ 514/423, 514/626, 311, 365, 378, 445, 471, 481, 596, 514/602, 603, 616, 617, 625; 548/536, 200, 548/248, 375.1; 564/197, 48, 80, 83, 84, 564/86, 161, 180; 549/479; 560/157; 544/144
See application file for complete search history.

(56) References Cited

U.S. PATENT DOCUMENTS

| 4,309,442 A | 1/1982 | Bey et al. ............. 424/319 |
| 4,774,339 A | 9/1988 | Haugland et al. ......... 548/405 |
| 4,818,770 A | 4/1989 | Weinstein et al. .......... 514/564 |
| 5,187,288 A | 2/1993 | Kang et al. .............. 548/110 |
| 5,248,782 A | 9/1993 | Haugland et al. ......... 548/110 |
| 5,252,714 A | 10/1993 | Harris et al. ............ 530/391.9 |
| 5,274,113 A | 12/1993 | Kang et al. .............. 548/405 |
| 5,433,896 A | 7/1995 | Kang et al. .............. 252/700 |
| 5,451,663 A | 9/1995 | Kang et al. .............. 530/367 |
| 5,656,671 A | 8/1997 | Bergeron, Jr. ............ 514/674 |

FOREIGN PATENT DOCUMENTS

| JP | 2-256656 A | 10/1990 |
| JP | 02 256656 | 1/1991 |
| JP | 09235271 A | 9/1997 |
| WO | WO 8502769 A | 7/1985 |
| WO | WO 91/00853 | 1/1991 |
| WO | WO 9214709 A | 9/1992 |
| WO | WO 9521612 A | 8/1995 |
| WO | WO 9622962 A | 8/1996 |
| WO | WO 9638464 A | 12/1996 |
| WO | WO 99/03823 | 1/1999 |
| WO | WO 00/34226 | 6/2000 |
| WO | WO 00/46187 | 8/2000 |

OTHER PUBLICATIONS

Blagbrough et al., Chem. Commun. (1998) 929-930.
Blagbrough et al., Toxicon (1992) 30(3):303-322.
Bruce et al., Toxicon (1990) 28(11):1333-1346.
Cullis et al., Chemistry & Biology (1999) 6(10):717-729.
Goodnow et al., Tetrahedron (1990) 46:3267-3286.
Koike et al., Neuroscience Research (1997) 29:27-36.
Nakanishi et al., Pure Appl. Chem. (1990) 62:1223-1230.
Tomasi et al., Bioorganic & Medicinal Chemistry Letters (1998) 8:635-640.
Yoneda et al., Bioorganic & Medicinal Chemistry Letters (2001) 11:1261-1264.

(Continued)

*Primary Examiner*—Peter O'Sullivan
(74) *Attorney, Agent, or Firm*—Connolly, Bove, Lodge & Hutz, LLP

(57) ABSTRACT

Novel inhibitors of polyamine transport having inhibition constants two orders of magnitude lower than those of known compounds are disclosed. These polyamine analogues are useful pharmaceutical agents for treating diseases where it is desired to inhibit polyamine transport or other polyamine binding proteins, for example cancer and postangioplasty injury. Novel chemical synthetic methods to obtain polyamine analogues are disclosed, including the production of a combinational polyamine library. These approaches yield analogues with desirable activities both for diagnostic and research assays and therapy. The assays of the invention are useful for high throughput screening of targets in the discovery of drugs that interact with the polyamine system.

19 Claims, 95 Drawing Sheets

OTHER PUBLICATIONS

Alhonen-Hongisto, L. et al. (1980). "Intracellular Putrescine Deprivation Induces Uptake of the Natural Polyamines and Methylglyoxal Bis(Guanylhydrazone)," *Biochem J* 192:941-945.

Alhohen-Hongisto, L. et al. (1985). "Tumourigenicity, Cell-Surface Glycoprotein Changes and Ornithine Decarbboxylase Gene Pattern in Ehrlich Ascites-Carcinoma Cells," *Biochem J* 229:711-715.

Aramaki, Y. et al. (1986). "Chemical Characterization of Spider Toxin, JSTX," *Proc Japan Acad* 62, Ser. B:359-362.

Asami, T. et al. (1989). "Acylpolyamines Mimic the Action of Joro Spider Toxin (JSTX) on Crustacean Muscle Glutamate Receptors," *Biomedical Res* 10:185-189.

Bardocz, S. et al. (1993) "Polyamines in food; Implications for Growth and Health," *J Biochem Nutr* 4:66-71.

Blagbrough, I.S. et al. (1998). "Practical Synthesis of Unsymmetrical Polyamine Amides," *Tetrahedron Lett* 39:439-442.

Bogle, R.G. et al. (1994). "Endothelial Polyamine Uptake: Selective Stimulation by L-arginine Deprivation," *Am J Physiol* 266:C776-C783.

Carrington, S. et al. (1996). "Inhibition of growth of B16 Murine Melanoma Cells by Novel Spermine Analogs," *Pharm Sci* 2(1):25-27.

Chamaillard, L. et al. (1997). "Polyamine Deprivation Prevents the Development of Tumor-Induced Immune Supression," *Br J Cancer* 76:365-370.

Chao, J. et al (1997). "N1-Dansy-Spermine and N1-(n-octanesulfonyl)-Spermine, Novel Glutamate Receptor Antagonists: Block and Permeation of N-Methyl-D-Aspartate Receptors," *Mol Pharmacol* 51(5):861-871.

Dhainaut et al. (1996). "New Purines and Purine Analogs as Modulators of Multidrug Resistance," *J Med Chem* 39:4099-4108.

DiPasquale, A. et al. (1978). "Epidermal Growth FActor Stimulates Putrescine Transport and Ornithine Decarboxylase Activity in Cultures Human Fibroblasts," *Exp Cell Res* 116:317-323.

Felshow, D.M. et al. (1997). "Selective Labeling of Cell-Surface Polyamine-Binding Proteins on Leukemic and Solid-Tumor Cell Types Using a New Polyamine Photoprobe," *Biochem J* 328(3):889-895.

Green, A.C. et al. (1996). "Polyamine Amides are Neuroprotective in Cerebellar Granule Cell Cultures Challenged with Excitatory Amino Acids," *Brain Research* 717/1-2:135-146.

Ha, H.C. et al. (1998). "The Natural Polyamine Spermine Functions Directly as a Free Radical Scavenger," *Proc Natl Acad Sci USA* 95:11140-11145.

Hayashi, S. et al. (1996). "Ornithine Decarboxylase Antizyme: A Novel Type of Regulatory Protein," *TIBS* 21:27-30.

Heller, J.S. et al. (1976). "Induction of a Protein Inhibitor to Ornithine Decarboxylse by the End Products of Its Reaction," *Proc Natl Acad Sci USA* 73:1858-1862.

Janne, J. et al. (1978). "Polyamines in Rapid Growth and Cancer," Biochim Biophys Acta 473:241-293.

Kashiwagi, K. et al. (1990). "Isolation of Polyamine Transport-Deficient Mutants of *Escherichia coli* and Cloning of the Genes for Polyamine Transport Proteins," *J Biol Chem* 265:20893-20897.

Khan, N., Quemener, V. et al. (1994). "Characterization of Polyamine Transport pathways", in *Neuropharmaacology of Polyamines* (Carter, C., ed.), Academic, San Diego, pp.37-60.

Kossorotov, A. et al. (1974). "Regulatory Effects of Polyamines on Membrane-Bound Acetylcholinesterase," *Biochem J* 144:21-27.

Krapcho, A.P. et al (1990). "Mono-Protected Diamines. N-tert-butoxylcarbonyl-α,ω-Alkanediamines from α,ω-Alkanediamines," *Syn Comm* 20:2559-2564.

Leveque, J. et al (1998). "The Gastrointestinal Polyamine Source Depletion Enhances DFMO induced Polyamine Depletion in MCF-7 Human Breast Cancer Cells In Vivo," *Anticancer Res* 18:2663-3668.

Li, Y. et al. (1997). "Comparative Molecular Field Analysis-Based Predictive Model of Structure-Function Relationships of Pilyamine Transport Inhibitors in L1210 Cells," *Cancer Res* 57:234-239.

Matsufuji, S. et al. (1996). "Reading Two Bases Twice: Mammalian Antizyme Fram Shifting in Yeast," *EMBO Journal* 15:1360-1370.

Matthews, H.R. (1993). "Polyamines, Chromatin Structure and Transription," *BioAssays* 15:561-566.

Moulinoux, J-P. et al. (1991). "Biological Significance of Circulating Polyamines in Oncology," Cell Mol Biol 37:773-783.

Moulinoux, J.P. et al. (1991). "Inhibition of growth of the U-251 Human Glioblastoma in Nude Mice by Polyamine Deprivation," *Anticancer Res* 11:175-180.

Moya, E. et al. (1994). "Synthesis and Neuropharmacological properties of Arthropod Polyamine Amide Toxins," *Neuropharmacology of Polyamines* (Carter, C., ed.), Academic, San Diego, pp. 167-184.

Murakami, Y. et al. (1992). "Ornithine Decarboxylase Is Degraded be the 26S Proteosome Without Ubiquitination," *Nature* 360:597-599.

Persson, L. et al. (1998). "Curative Effect of d,1-2-Difluoromethylornithine on Mice Bearing Mutant L1210 Leukemia Cells Deficient in Polyamine Uptake," *Cancer Res* 48:4807-4811.

Pohjanpelto, P. (1976). "Putrescine Transport is Greatly Increased in Human Fibroblasts Initiated to Prolifarete," *J Cell Biol* 68:512-520.

Porter, C.W. et al. (1984). "Aliphatic Chain Length Specificity of the Polyamine Transport System in Ascites L1210 Leukemia Cells," *J Cancer Res* 44:126-128.

Qarawi, M. et al. (1997). "Optimization of the MMT Assay for B16 Murine Melanoma Cells and Its Application in Assessing Growth Inhibition by Polyamines and Novel Polyamine Conjugates," *Pharm Sci.* 3(5/6):235-239.

Quemener, V. et al. (1992). "Polyamine Deprivation Enhances Antitumoral Efficacy of Chemotherapy," *Anticancer Res* 12:1447-1454.

Raditsch, M. et al. (1996). "Polyamine Spider Toxins and Mammalian N-Methyl-D-Aspartate Receptors. Structural Basis for Channel Blocking and Binding of Argiotoxin 636," *Eur J Biochem* 240:416-426.

Ransom, R.W. et al. (1988). "Cooperative Modulation of [3H]MK-801 Binding to the N-Methyl-D-Aspartate Receptor_Ion Channel Complex by L-Glutamate, Clycine, and Polyamines," *J Neurochem* 51:830-836.

Russell, D. et al. (1968). "Amine Synthesis in Rapidly Growing Systems: Ortithine Decarboxylase Activity in Generating Rat Liver, Chick Embryo, and Various Tumors," *Proc Natl Acad Sci USA* 60:1420-1427.

Sarhan, S. et al. (1989). "The gasrointestial Tract as Polyamine Source for Tumor Growth," *Anticancer Res.* 9:215:224.

Scalabrino, G. et al. (1981). "Polyamines in Mammalian Tumors. Part 1," *Adv Cancer Res* 35:151-268.

Scalabrino, G. et al. (1982). "Polyamines in Mammalian Tumors. Part 11," *Adv Cancer Res* 36:1-102.

Schechter, P.J. et al. (1987). "In Inhibition of Polyamine Metabolism. Biological Significance and Basis for New Therapies," McCann, P.P. et al., eds; pp. 345-364.

Seiler, N. (1987). "Functions of Polyamine Acetylation," *Can Pharmacol* 65:2024-2035.

Seiler, N. et al. (1990). "Polyamine Transport in Mammalian Cells," *Int J Biochem* 22:211-218.

Seiler, N. (1995). "Polyamine Oxydase, Properties and Functions," *Progress in Brain Res* 106:333-344.

Seiler, N. et al. (1998). "Polyamine Sulfonamides with NMDA Antagonist Properties Are Potent Calmodulin Antagonists and Cytotoxic Agents," *Int J Biochem Cell Biol* 30(3):393-406.

Sugiyama, S. et al. (1996). "Crystal Structure of PotD, the Primary Receptor of the Polyamine Transport System in *Escherichia coli,*" *J Biol Chem* 271:9519-9525.

Suzuki, T. et al. (1994). "Antizyme Protects Against Abnormal Accumulation and Toxicity of Polyamines in Ornithine Decarboxylase-Overproducing Cells," *Proc Natl Acad Sci USA.*

Tabor, H. et al. (1976). "1,4-Diaminobutrane (putrescine), Spermidine, and Spermine," *Ann Rev Biochem* 45:285-306.

Tomitori, H. et al. (1999). "Identification of a Gene for a Polyamine Transport Protein in Yeast," *J Biol Chem* 274:3265-3267.

Tsubokawa, H. et al. (1995). "Effects of a Spider Toxin and Its Analoque on Glutamate-Activated Currents in the Nippocampal CA1 Neuron after Ischemia," *J Neurophys* 74:218-225.

Veznik, F. et al. (1991). "Synthese von N1,4-Di(p-cumaroyl)spermin, einem moglichen Biogenese-Vorlaufer von Aphelandrin," *Helvetica Chimica Acta* 74:654-661.

Volkow, N. et al. (1983). "Labeled Putrescine as a Probe in Brain Tumors," *Science* 221:673-675.

Webb, H.K. et al. (1999). "1-(N-Alkylamino)-11-(N-Ethylamino)-4,8-Diazaundecanes: Simple Synthetic Polyamine Analogues That Differentially Alter Tubulin Polymerization," *J. Med Chem* (in press).

Williams, K. et al. (1991) "Minireview: Modulation of the NMDA Receptor by Polyamines" *Life Science* 48:269-298.

Williams, K. (1997). "Interaction of Polyamines with Ion Channels," *Biochem J* 325:289-297.

Wolff, J. (1998). "Promotion of Mircotubule Asembly by Oligocations: Cooperatively between Charged Groups," *Biochemistry* 37:10722-10729.

Xia, C.Q. et al. (1998). "QSAR Analysis of PolyamineTransport Inhibitors in L1210 Cells," *J Drug Target* 6:65-77.

Gallop, M.A., et al., "Applications of Combinatorial Technologies to Drug Discovery. Background and Peptide Combinatorial Libraries.," J. Med. Chem., (1994) 37(9): 1233-51.

Ganem, B., "New Chemistry of Naturally Occuring Polyamines," ACC. Chem. Res., (1982) 15:290-8.

Ganem, B., et al., "Chemistry of Naturally Occurring Polyamines. II. Unsaturated Spermidine and Spermine Derivatives," J. Org. Chem., (1987) 52:5044-6.

Ganem, B., et al., "Chemistry of Naturally Occuring Polyamines. 10. Nonmetabolizable Derivatives of Spermine and Spermidine," J. Org. Chem., (1986) 51:4856-61.

Goodnow, Jr. R.A., et al., "Oligomer Synthesis and DNA/RNA Recognition Properties of a Novel Oligonucleotide Backbone Analog: Glucopyranosyl Nuclei Amide (GNA)," Tetrahedron Lett., (1997) 38(18):3199-3202.

Goodnow, Jr., P.A., et al., "Synthesis of Thymine, Cytosine, Adenine, and Guanine Containing N-Fmoc Protected Amino Acids: Building Blocks for Construction of Novel Oligonucleotide Backbone Analogs," Tetrahedron Lett., (1997) 38(18):3195-8.

Gordon, E.M., et al., "Applications of Combinatorial Technologies to Drug Discovery Combinatorial Organic Synthesis, Library Screening Strategies, and Future Directions," J. Med. Chem., (1994) 37(10): 1385-1401.

Gorus, F., et al., "Applications of Bio- and Chemiluminescence in the Clinical Laboratory," Clin. Chem., (1979) 25(4):512-9.

Han, H. et al., "Liquid-Phase Combinatorial Synthesis," Proc. Natl. Acad. Sci. USA, (1995) 92:6419-23.

Hernandez, A.S. et al., "Solid-Supported tert-Alkoxycarbonylation Reagents for Anchoring of Amines During Solid Phase Organic Synthesis," J. Org. Chem., (1997) 62:3153-7.

Huber, M. et al., "2,2'-Dithiobis (N-ethyl-spermine-5-carboxamide) Is a High Affinity, Membrane-Impermeant Antagonist of the Mammalian Polyamine Transport System," J. Biol. Chem., (1996) 271(44):27556-63.

Laguzza, B.C., et al., "A New Protecting Group For Amines. Synthesis of Anticapsin from L-Tyrosine" Tetrahed. Lett., (1981) 22(16):1483-6.

Lakanen, J.R., et al., "α-Methyl Polyamines: Metabolically Stable Spermidine and Spermine Mimics Capable of Supporting Growth in Cells Depleted of Polyamines," J. Med. Chem., (1992) 35:724-34.

Lee, J., "Facile Preparation of Cyclopropylamines from Carboxamides," J. Org. Chem., (1997) 62:1584-5.

Li, Y. et al. "Synthesis and Antitumor Evaluation of a Highly Potent Cytotoxic DNA Cross-Linking Polyamine Analogue, 1,12-Diaziridinyl-4, 9-diazadodecane," J. Med. Chem., (1996) 39:339-41.

Lloyd-Williams, P., "*Convergent Solid-Phase Peptide Synthesis,*" Tetrahedron, (1993) 49(48): 11065-133.

Marton, L.J., et al., "*Polyamines as Targets for Therapeutic Intervention,*" Annu. Rev. Pharmacol. Toxicol., (1995) 35:55-91.

Muramoto, K., "Preparation and Characterization of Photoactivable Heterobifunctional Fluorescent Reagents," Agric. Biol. Chem., (1984) 48 (11), 2695-9.

Nakaoka, T., et al., "Inhibition of Rat Vascular Smooth Muscle Proliferation In Vitro and In Vivo by Bone Morphogenetic Protein-2," J. Clin. Invest., (1997) 100 (11): 2824-32.

Pfitzner, K.E., et al., "Sulfoxide-Carbodiimide Reactions. I.A Facile Oxidation of Alcohols," J. Am. Chem. Soc., (1965) 87(24): 5661-9.

Quemener, V., et al., "Polyamine Deprivation: A New Tool in Cancer Treatment," Anticancer Res., (1994) 14:443-8.

Raines, D.E., et al., "Potential-Dependent Phase Partitioning of Fluorescent Hydrophobic Ions in Phospholipid Vesicles," J.Membrane Biol., (1984) 82:241-7.

Rajeev, K.G., et al., "Conformationally Restrained Chiral Analogues of Spermine: Chemical Synthesis and Improvements in DNA Triplex Stability," J.Org Chem., (1997) 62:5169-73.

Ranganathan, R.S., et al., "Novel Analogs of Nucleoside 3',5'-Cyclic Phosphates. I. 5'-Mono-and Dimethyl Analogs of Adenosine 3', 5'- Cyclic Phosphate," J. Org. Chem., (1974) 39(3):290-8.

Rink, H., "Solid-phase synthesis of Protected Peptide Fragments Using A Trialkoxy-Diphenyl-Methylester Resin," Tetrahed. Lett., (1987) 28(33): 3787-90.

Salemme, F.R., et al., "Serendipity Meets Precision: The Integration of Structure-Based Drug Design and Combinatorial Chemistry for Efficient Drug Discovery," Structure, (1997) 5(3):319-24.

Sasaki, Y. et al., "Solid-Phase Synthesis and Biological Properties of Ψ[CH$_2$NH] Pseudopeptide Analogues of a Highly Potent Somatostatin Octapeptide," J. Med. Chem., (1987 30(7):1162-6.

Schallenberg, E.E., et al., "Ethyl Thioltriifluoroacetate As An Acetylating agent with Particular Reference to Peptide Synthesis," J.Am.Chem.Soc., (1955) 77:2779-83.

Seiler, N. et al., "*Polyamine transport in Mammalian Cells. An Update.,*" Int. J. Biochem. Cell Biol., (1996) 2898): 843-61.

Seiler, N. et al., "*Polyamine Transport In Mammalian Cells,*" Int.J.Biochem., (1990) 22(3):211-8.

Shyng, S.-L., et al., "Depletion of Interacellular Polyamines Relieves Inward Rectification of Potassium Channels," Proc. Natl. Acad. Sci. USA, (1996) 93:12014-9.

Siegel, M.G. et al., "Rapid Purification of Small Molecule Libraries b y Ion Exchange Chromatography," Tetrahedron Lett., (1997) 389(19): 3357-60.

Singh, S. et al., "Characterization of Simian Malarial Parasite (Plasmodium Knowlesi) -induced Putrescine Transport in Rhesus Monkey Erythrocytes," J. Biol. Chem., (1997) 272(21): 13506-11.

Thompson, L.A. et al., "Straightforward and General Method for Coupling Alcohols to Solid Supports," Tetrahed. Lett., (1994) 35:9333-6.

Ventura, C. et al., "Polyamine Effects on [Ca2+] 1 Homeostasis and Contractility in Isolated Rat Ventricular Cardiomyocytes," Am. J. Physiol., (1994) 267:H857-H592.

Wang, S.-S., "p-Alkoxybenzyl Alcohol Resin and p-Alkoxybenzloxycarbonylhydrazide Resin for Solid Phase Synthesis of Protected Peptide Fragments," J. Am. Chem. Soc., (1973) 95(4): 1128-1333.

"The natural polyamine spermine functions directly as a free radical scavenger" Ha et al., *Proc. Natl. Acad. Sci.* vol. 95, pp. 11140-11145, Sep. 1998.

"The role of polyamine catabolism in polyamine analogue-induced programmed cell death" Ha et al., *Proc. Natl. Acad. Sci.*, vol. 94, pp. 11557-11562, Oct. 1997.

| # | STRUCTURE | Ki(M)[a] | R[b] | METHOD[c] |
|---|---|---|---|---|
| 3 | 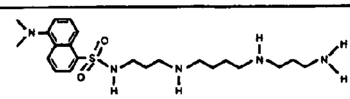 | 0.080 | 20 | I |
| 4 | 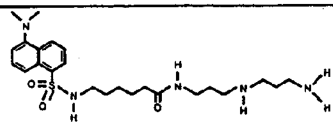 | 0.010 | 400 | IX, XIII |
| 5 | 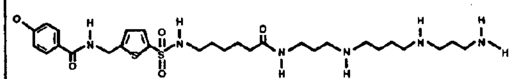 | 0.010 | 210 | XIII |
| 6 | 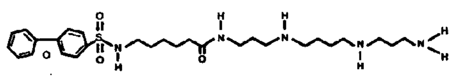 | 0.005 | 220 | XIII |
| 7 | 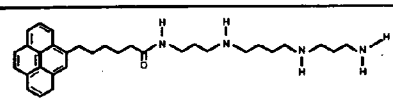 | 0.10 | 3.6 | III |
| 8 | 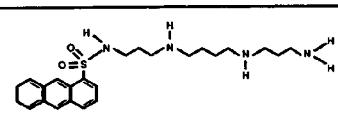 | 0.110 | 3.7 | II |
| 9 | 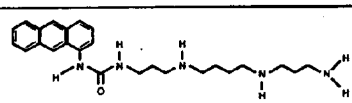 | 0.440 | 2.7 | IV |
| 10 | 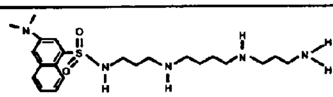 | 0.050 | >10 | XV |
| 11 | | 0.190 | 2.4 | XV | a INHIBITION OF POLYAMINE UPTAKE: Ki DETERMINED FROM LINEWEAVER-BURKE DOUBLE RECIPROCAL PLOTS
b INHIBITION OF TUMOR CELL GROWTH: R IS RATIO OF IC50 (COMPOUND ALONE) TO IC50 (COMPOUND + DFMO)
c NUMBERS REFER TO EXAMPLES (DESCRIBING SYNTHESIS)
d PURCHASED FROM ALDRICH CHEMICAL COMPANY

FIG. 2

| # | STRUCTURE | Ki(M)[a] | R[b] | METHOD[c] |
|---|---|---|---|---|
| 12 | 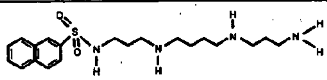 | 0.150 | 4.3 | XV |
| 13 | 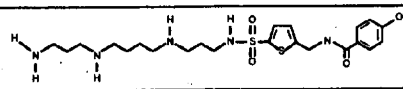 | 0.058 | >47 | XV |
| 14 | 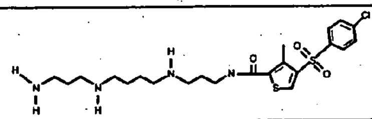 | 0.037 | 14 | XVII |
| 15 | 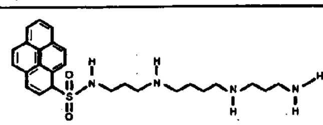 | 0.091 | 2.2 | II |
| 16 | 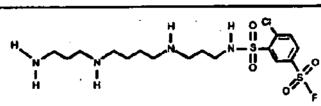 | 0.08 | 2.1 | XV |
| 17 | 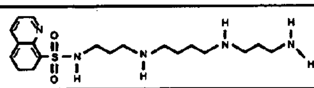 | 0.43 | >31 | XV |
| 18 | 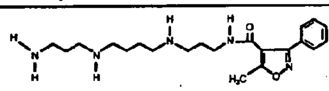 | 0.083 | 40 | XVII |
| 19 | 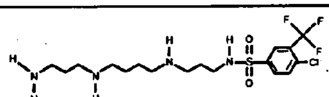 | 0.24 | >10 | XV |
| 20 | 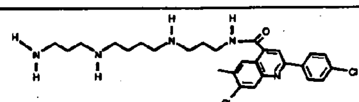 | 0.28 | 1.0 | XVII |
| 21 | 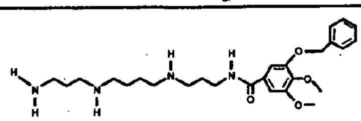 | 0.084 | 1.0 | XVII |

FIG. 2 (CONT.1)

| # | STRUCTURE | Ki(M)[a] | R[b] | METHOD[c] |
|---|---|---|---|---|
| 22 | 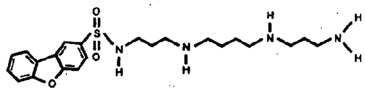 | 0.066 | 11 | XV |
| 23 | 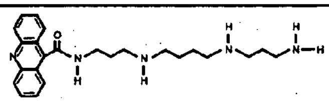 | 0.250 | 6.2 | II |
| 24 | 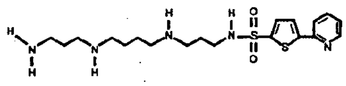 | 0.23 | 10 | XV |
| 25 | 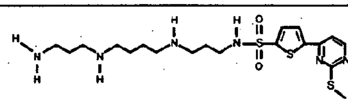 | 0.067 | 8.6 | XV |
| 26 | 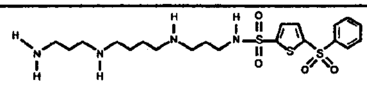 | 0.180 | 15 | XV |
| 27 | 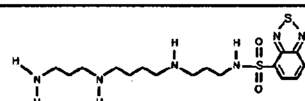 | 0.650 | 9.9 | XV |
| 28 | 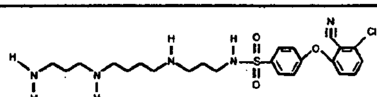 | 0.054 | 9.3 | XV |
| 29 | 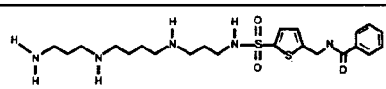 | 0.076 | >46 | XV |
| 30 | 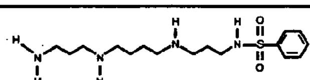 | 0.120 | >10 | XV |
| 31 | 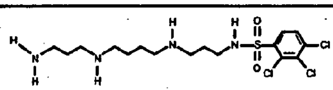 | 0.083 | >12 | XII |

FIG. 2 (CONT.2)

| # | STRUCTURE | Ki(M)[a] | R[b] | METHOD[c] |
|---|---|---|---|---|
| 32 | 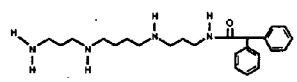 | 0.093 | 2.1 | XVII |
| 33 | 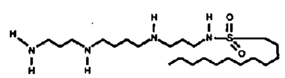 | 0.17 | 1.4 | XV |
| 34 | 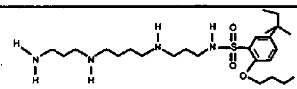 | 0.120 | 1.0 | XV |
| 35 | 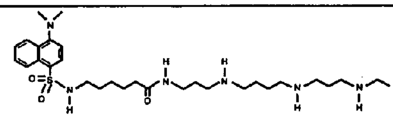 | 0.041 | 33 | XIII |
| 36 | 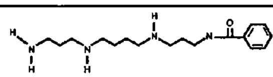 | 0.61 | >2 | XVII |
| 37 | 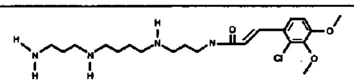 | 0.150 | 2.4 | XVII |
| 38 | 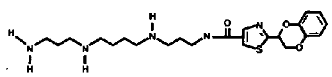 | 0.140 | 1.0 | XVII |
| 39 | 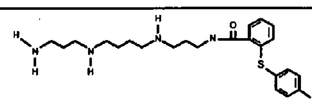 | 0.500 | 1 | XVII |
| 40 | 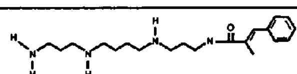 | 0.086 | 18 | XVII |
| 41 | 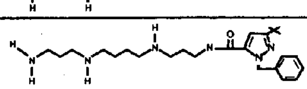 | 0.200 | 1.0 | XVII |

FIG. 2 (CONT.3)

| # | STRUCTURE | Ki(M)[a] | R[b] | METHOD[c] |
|---|---|---|---|---|
| 42 | 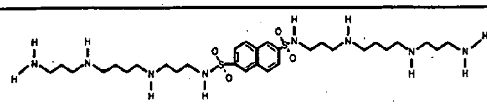 | 0.110 | 1.1 | XIV |
| 43 | 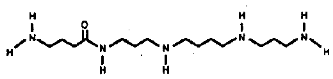 | 0.033 | 76 | XVII |
| 44 | 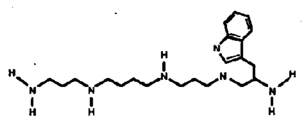 | 0.073 | 39 | XIII |
| 45 | 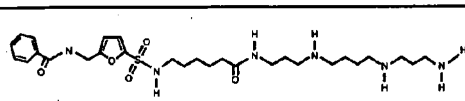 | 0.052 | 3.0 | XIII |
| 46 | 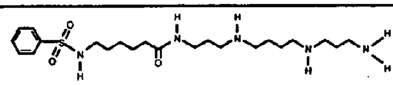 | 0.082 | 63 | XIII |
| 47 | 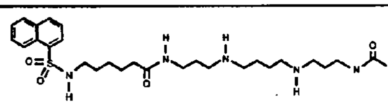 | 2.1 | 6.8 | XII |
| 48 | 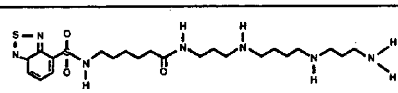 | 0.079 | >49 | XII |
| 49 | 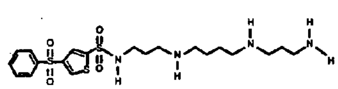 | 0.067 | 3.2 | XV |
| 50 | 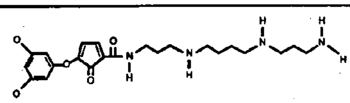 | 0.12 | 1.0 | XVII |
| 51 | 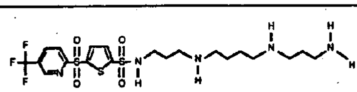 | 0.083 | 1.5 | XV |

FIG. 2 (CONT.4)

| # | STRUCTURE | Ki(M)[a] | R[b] | METHOD[c] |
|---|-----------|----------|------|-----------|
| 52 | 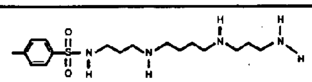 | 0.094 | 5.3 | XV |
| 53 | 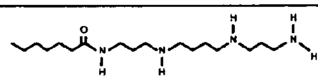 | 0.18 | 1.0 | XV |
| 54 | 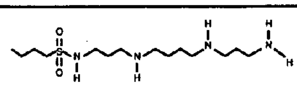 | 0.19 | 2.0 | XV |
| 55 | 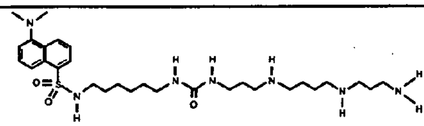 | 0.079 | >1.1 | IV |
| 56 | 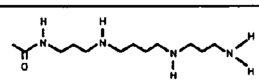 | 0.190 | | d |
| 57 | 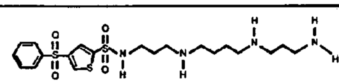 | 0.017 | 170 | XV |
| 58 | 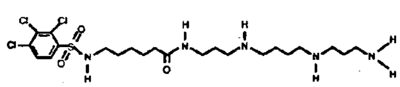 | 0.050 | 189 | XIII |
| 59 | 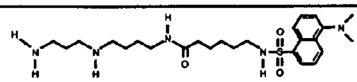 | | >1 | XIII |
| 60 | 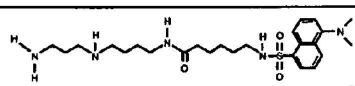 | | >1 | XIII |
| 61 | 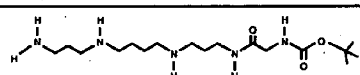 | 0.200 | 1.0 | XIII |

FIG. 2 (CONT.5)

| # | STRUCTURE | Ki(M)[a] | R[b] | METHOD[c] |
|---|---|---|---|---|
| 62 | 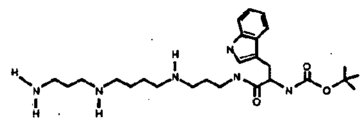 | | >2.0 | XIII |
| 63 | 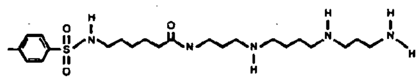 | 0.050 | >1 | XIII |
| 64 | 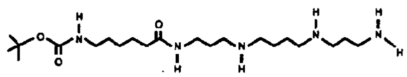 | 0.046 | | XIII |
| 65 | 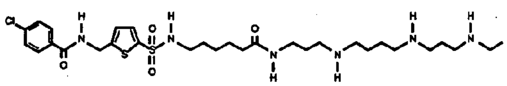 | 0.012 | | XIII |
| 66 | 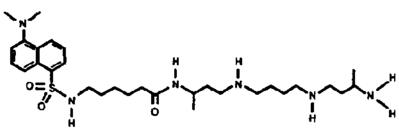 | 0.018 | 27 | XIII |
| 67 | 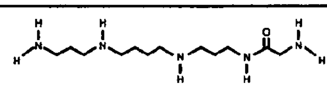 | 0.07 | 1.0 | XIII |
| 68 | 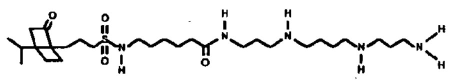 | 0.110 | >4.4 | XIII |
| 69 | 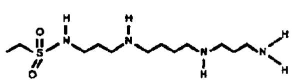 | 0.22 | 1 | XV |
| 70 | 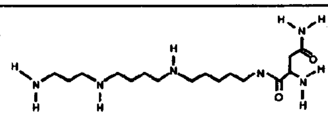 | 0.033 | >12.2 | XIII |
| 71 | 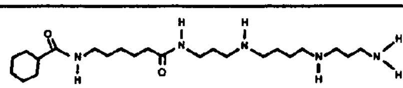 | 0.160 | >1.5 | XIII |

FIG. 2 (CONT.6)

| # | STRUCTURE | Ki(M)[a] | R[b] | METHOD[c] |
|---|---|---|---|---|
| 72 | 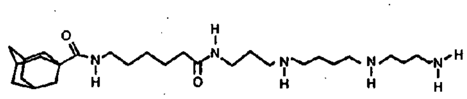 | 0.031 | >100 | XIII |
| 73 | 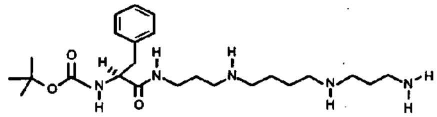 | 0.094 | >1 | XIII |
| 74 | 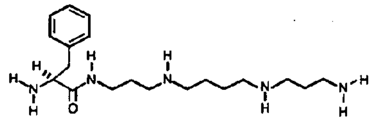 | 0.200 | 1.0 | XIII |
| 75 | 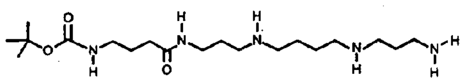 | 0.130 | >1 | XIII |
| 76 | 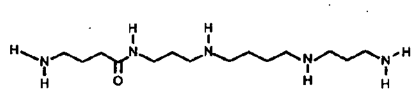 | 0.040 | 1.0 | XIII |
| 77 | 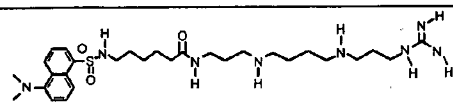 | 0.093 | 1 | XIII |
| 78 | 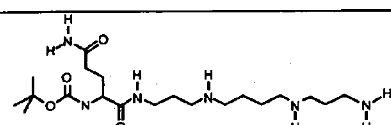 | 0.156 | | XIII |
| 79 | 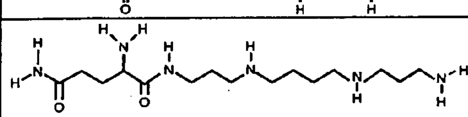 | 0.047 | 1 | XIII |
| 80 | 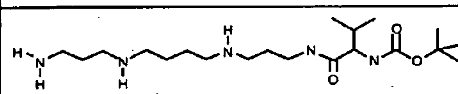 | 0.258 | | XIII |
| 81 | 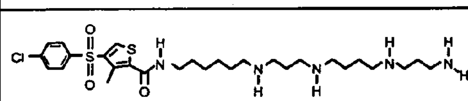 | 0.0096 | 153 | XIII |

FIG. 2 (CONT.7)

| # | STRUCTURE | Ki(M)[a] | R[b] | METHOD[c] |
|---|---|---|---|---|
| 82 | 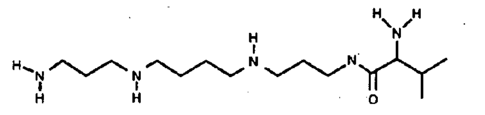 | 0.097 | >54 | XIII |
| 83 | 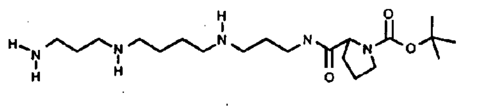 | 0.183 | | XIII |
| 84 | 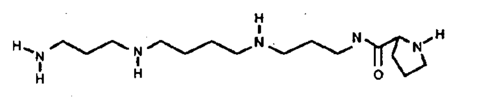 | 0.036 | >3.2 | XIII |
| 85 | 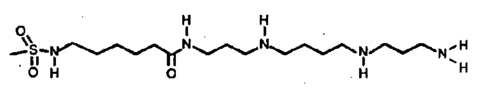 | 0.048 | >6.5 | XIII |
| 86 | 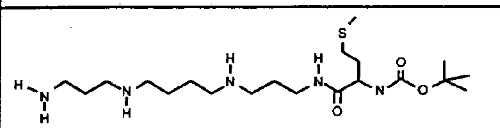 | 0.091 | | XIII |
| 87 | 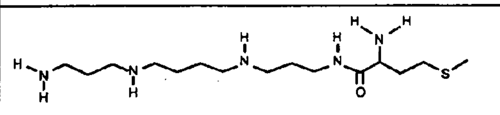 | 0.034 | >1 | XIII |
| 88 | 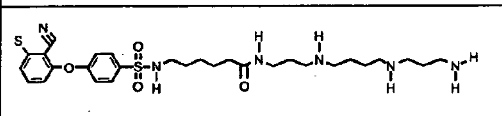 | 0.014 | >40 | XIII |
| 89 | 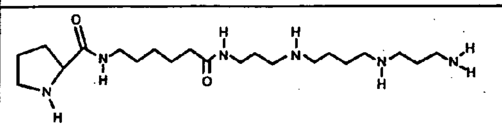 | 0.020 | >1 | XIII |
| 90 | 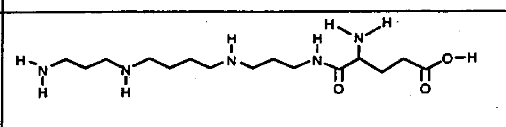 | 0.077 | | XIII |
| 91 | 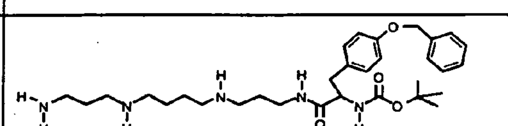 | 0.037 | 1 | XIII |

FIG. 2 (CONT.8)

| # | STRUCTURE | Ki(M)[a] | R[b] | METHOD[c] |
|---|---|---|---|---|
| 92 | 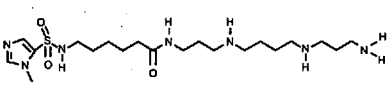 | 0.300 | 1 | XIII |
| 93 | 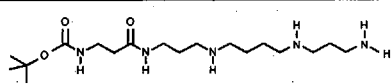 | 0.061 | 1 | XIII |
| 94 | 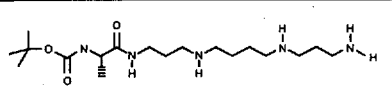 | 0.042 | 1 | XIII |
| 95 | 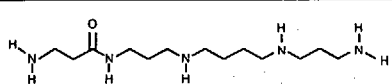 | 0.050 | 1 | XIII |
| 96 | 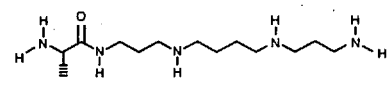 | 0.034 | 1 | XIII |
| 97 | 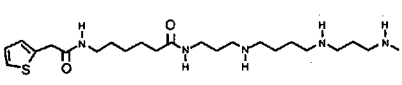 | 0.027 | 1 | XIII |
| 98 | 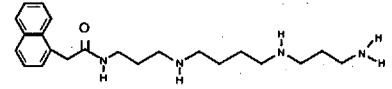 | 0.180 | 12 | d |
FIG. 2 (CONT.9)

111a

112a

111b

112b

113

114

X = 1 TO 4

X = 0 TO 3

115

COMPOUND 1202
L-LYS-SPM

COMPOUND 1390
D-LYS-SPM

COMPOUND 1380
L-LYS-SPM THIOMIDE

COMPOUND 1391
L-LYS-SPM(METHYLAMIDE)

COMPOUND 1392
L-LYS-SPM(α-METHYL)

COMPOUND 1393-1405
L-LYS-SPM(ISOAMIDE)

COMPOUND 1202 AND VARIATIONS THEREOF.

WHERE   Y = O, S OR NH;
R = VARIOUS GROUPS INCLUDING: PROPYLAZIRIDINE, PROPYLAMINE HEXYLDANSYLSULFONAMIDE
$R_1$ = H, $CH_3(CH_2)_n$-, WHERE n=1 TO 10;
X = H OR HALOGEN

WHERE  X= SPACER₁, Y= SPACER₂; AND Z= SPACER₃; AND
R₁, R₂ AND R₃ CAN BE ALICYCLIC, AROMATIC, OR HETEROCYLIC

161

162

163
TRIFLUOPERAZINE

164
THORAZINE

165
IMIPRAMINE

166

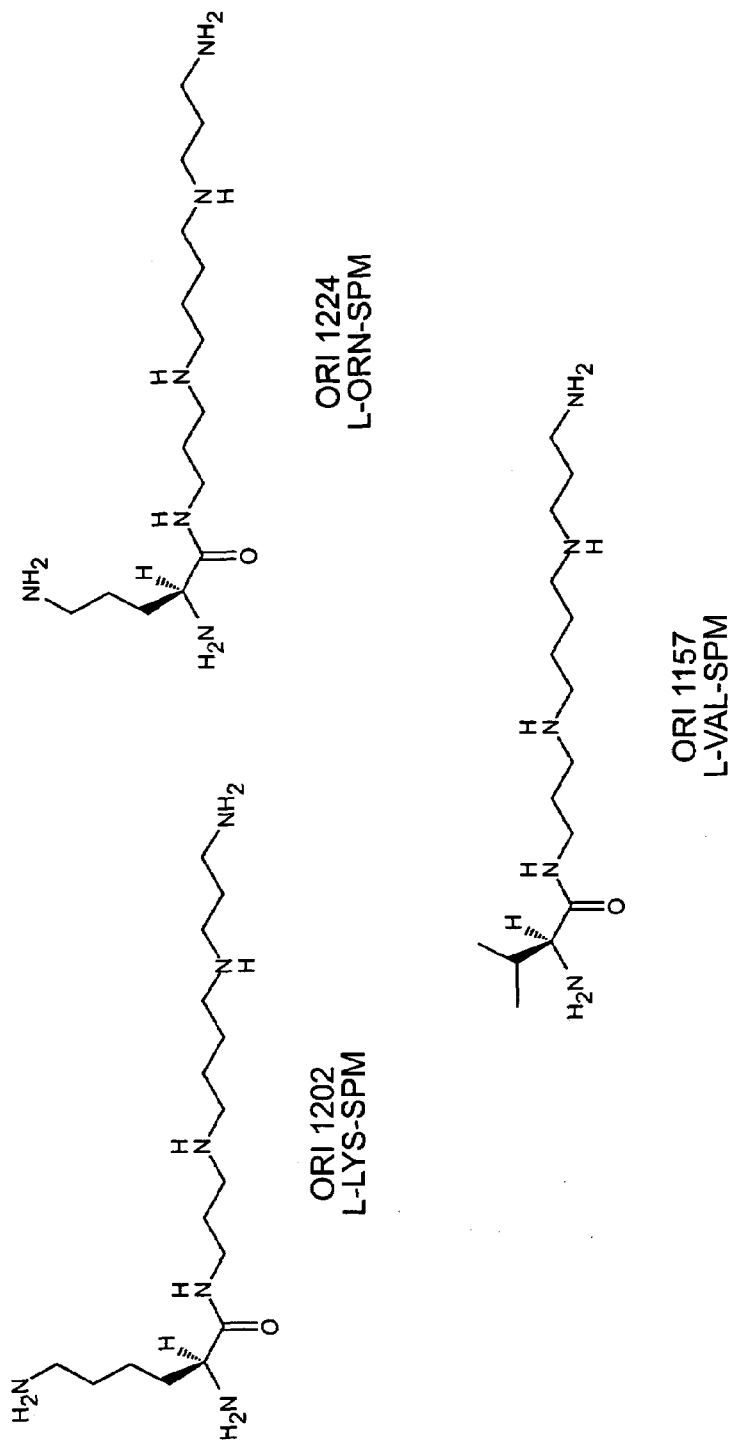
FIG. 44a PREFERRED NATURAL AND NON NATURAL AMINO ACID AMIDES OF SPERMINE.

ORTHO, META AND PARA AROMATIC SUBSTITUTION n = 1 TO 12

GENERAL STRUCTURE OF BIS-AMIDE DIMERS OF SPERMINE LINKED BY AN ALIPHATIC OR AROMATIC DI-ACID CHAIN.

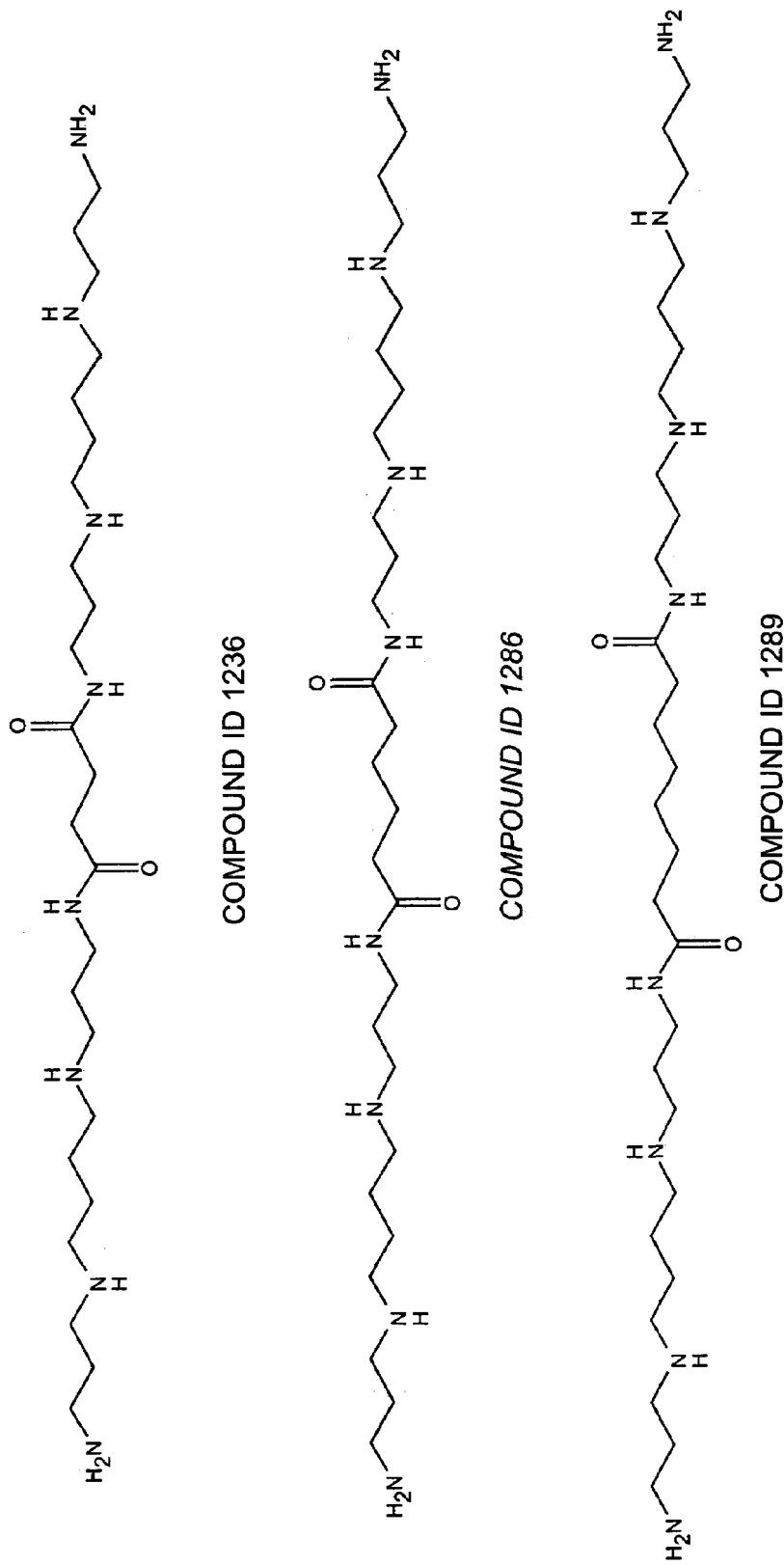
FIG. 44c  PREFERRED LINKED BIS-AMIDE DIMERS OF SPERMINE.

N1-MONOSUBSTITUTED POLYAMINES: AMIDES, NO LINKER

| ID | MOL WEIGHT | STRUCTURE | TRANSPORT>CELL LINE | Ki | GROWTH INHIBITION>CELL LINE | HALF EFFECT DRUG DFMO | IC50 |
|---|---|---|---|---|---|---|---|
| 1032 | 387.5295 | 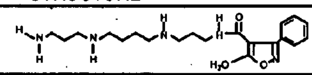 | MDA | 0.19 | MDA | 3.58 | >300 |
| 1033 | 421.9745 | 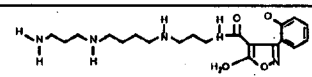 | MDA | 0.083 | | | |
| | | | MDA | 1.0 | MDA | | >300 |
| 1035 | 516.5189 | 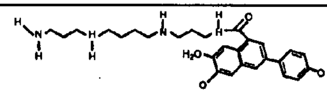 | MDA | 0.28 | MDA | | 50 |
| 1037 | 472.6331 | 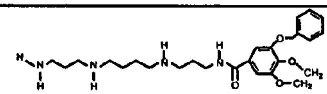 | MDA | 0.084 | MDA | | 100 |
| 1038 | 407.9474 | 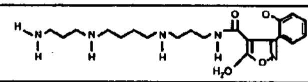 | MDA | >10 | MDA | | >300 |
| 1039 | 502.4918 | 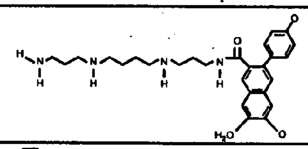 | MDA | >10 | MDA | | 30 |
| 1043 | 407.5635 | 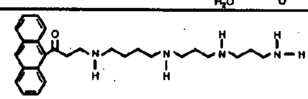 | MDA | 0.344* | MDA | 22.3 | 200 |
| 1053 | 394.5648 | 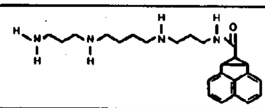 | MDA | 0.4 | MDA | | 260 |
| | | | MDA | 0.54 | | | |
| 1072 | 595.8762 | 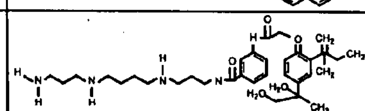 | mda | >1 | | | |

FIG. 45a

| | | | | | |
|---|---|---|---|---|---|
| 1073 | 306.4549 | | MDA | >10 | >300 |
| | | | MDA | 0.61 | 150 |
| 1076 | 426.9911 | | MDA | 0.116 | mda | 28.1 | 150 |
| 1077 | 501.1143 | | MDA | 0.165* | mda | | 56 |
| | | | MDA | 0.11* | mda | 2.46 | |
| 1078 | 447.604 | | MDA | 0.037 | mda | | 19 |
| | | | MDA | 0.19* | mda | | |
| | | | | | pc-3 | | 19.4 |
| | | | | | caco-2 | | 24.4 |
| | | | | | cem | | 6.9 |
| 1079 | 429.6323 | | MDA | 0.594* | pc-3 | | 83 |
| | | | | | mda | | 78 |
| 1080 | 346.5202 | | MDA | 0.062* | mda | 7.4 | 190 |
| | | | MDA | 0.086 | | | |
| 1081 | 442.6531 | | MDA | 0.297* | mda | | 26 |
| | | | MDA | 0.12 | mda | | |
| | | | | | pc-3 | | 5.5 |
| | | | | | caco-2 | | 23.0 |
| | | | | | cem | | 1.7 |
| 1104 | 457.4043 | | | | mda | | 18 |
| | | | | | pc-3 | | 20.2 |
| | | | | | caco-2 | | 36.2 |
| | | | | | cem | | 4.5 |

| | | | | | |
|---|---|---|---|---|---|
| 1163 | 302.4638 | | | | |
| 1166 | 230.36 | | | >100 | |
| 1167 | 256.3943 | | mda | | |
| | | | H157 | >100 | |
| | | | mda | >100 | |
| 1169 | 412.62 | MDA | h157 | >100 | |
| | | 0.0252 | mda | >300 | >300 |
| 1208 | 308.47 | | | | |
| 1210 | 352.57 | | pc-3 | 20.1 | >300 |
| 1211 | 341.41 | | | | |
| 1213 | 328.4829 | | | | |
| 1214 | 325.46 | | | | |
| 1215 | 284.45 | | | | |
| 1216 | 313.49 | | | | |

| | | | | | | |
|---|---|---|---|---|---|---|
| 1217 | 307.44 | 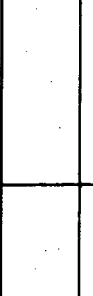 | MDA | | | |
| 1218 | 307.4424 | 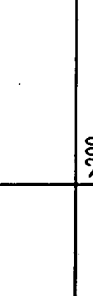 | | | | |
| 1235 | 364.5792 | 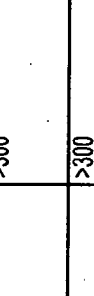 | MDA | 1.14 | | |
| 1240 | 378.6062 | 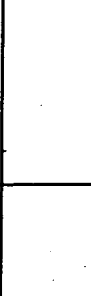 | | | mda | >300 |
| 1249 | 470.5594 | 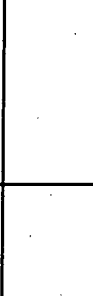 | MDA | >1 | pc-3 | >300 |
| 1251 | 392.5053 | 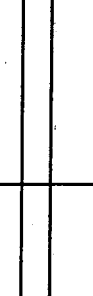 | MDA | | | |
| 1347 | 472.6795 |  | | | | |
FIG. 45a (CONT. 3)

FIG. 45b

N1-MONOSUBSTITUTED POLYAMINES: AMIDES, WITH LINKER

| ID | MOL WEIGHT | STRUCTURE | TRANSPORT>CELL LINE | Ki | GROWTH INHIBITION>CELL LINE | HALF EFFECT | DRUG DFMO IC50 |
|---|---|---|---|---|---|---|---|
| 1002 | 548.7972 | 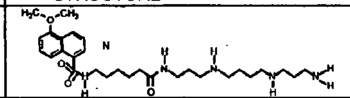 | MDA-MB-231 | .024* | MDA-MB-231 | 2.2 | >100 |
| | | | A172 | 0.16* | | | |
| | | | PC-3 | 0.0339* | | | |
| | | | MCF-7 | 0.012 | | | |
| | | | MDA | 0.0152* | | | |
| | | | CaCo | 0.0078* | | | |
| | | | mda | 0.0245-0.13 | MDA-MB-231 | 2.0 | >100 |
| | | | mda | 0.0052-0.03 | mda | 0.63 | 450 |
| | | | MDA | 8.6nM | mda | 2.0 | 380 |
| | | | | | mcf-7 | | 72 |
| | | | | | casmc | | |
| 1009 | 472.6795 | 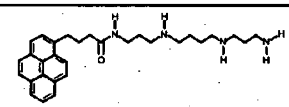 | MDA | 0.104 | MDA | <3 | 25 |
| | | | A172 | 0.12 | | | |
| 1022 | 370.5425 | 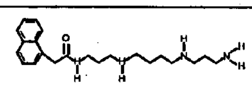 | | | MDA | 9.4 | 79 |
| | | | MDA | 0.230 | MDA | 8.26 | >300 |
| 1040 | 401.5974 | 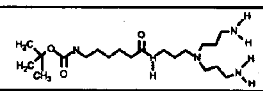 | | | mda | | >100 |
| 1055 | 398.5718 | 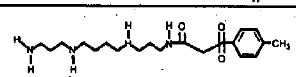 | MDA | | mda | | 6.9 |
| 1056 | 396.5807 | 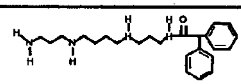 | MDA | 0.11* | MDA | | 150 |

| | | | | | |
|---|---|---|---|---|---|
| 1059 | 546.822 | [structure] | MDA | 6.5* | mda | | 70 |
| 1060 | 439.8164 | [structure] | MDA | 0.099 | mda | >300 | >300 |
| 1061 | 576.8513 | [structure] | MDA | 0.00895 | mda | <3 | 360 |
| 1063 | 550.7666 | [structure] | MDA MDA MDA | 0.0942 41.2 nM 57.8 nM | mda | 9.81 | 560 |
| 1064 | 510.7013 | [structure] | MDA | 88* | mda | | 18 |
| 1065 | 632.9597 | [structure] | MDA | >30 | mda | >100 | >100 |
| 1066 | 650.9722 | [structure] | MDA | 0.76 | mda | >30 | >30 |
| | | | | 19.2* | mda | | 27 |
| | | | | | pc-3 | | 8.7 |
| | | | | | caco-2 | | >30 |
| | | | | | cem | | 2.9 |
| 1067 | 492.6888 | [structure] | MDA | 0.070* | mda | >30 | >30 |
| 1068 | 506.7567 | [structure] | MDA MDA | 0.43 >30 | | >30 | >30 |
| 1069 | 459.431 | [structure] | mda | >1 | | | |
| | | | MDA | 0.74 | | | |

FIG. 45b (CONT. 1)

| | | | | | |
|---|---|---|---|---|---|
| 1083 | 401.5974 | [structure] | | | |
| 1085 | 373.5025 | [structure] | mda | 81.3 | mda | >100 |
| | | | | | | >300 |
| 1086 | 481.6 | | mda | 2.2 | | |
| 1090 | 629.2897 | [structure] | mda | 0.0147 | mda | 300 |
| | | | MDA | 0.00997 | | |
| | | | PC-3 | 0.070* | | |
| | | | MDA | 0.01324 | | |
| | | | MCF-7 | 0.0252 | | 0.960 |
| | | | CaCo | 0.013* | | |
| | | | MDA | 0.022* | | |
| | | | MDA | 13.3-15.7 nM | mda | |
| | | | MDA | 0.0216 Pre- | | >300 |
| | | | MDA | 0.0273 | | 1.54 |
| | | | HT-29 | 0.0397 | | |
| | | | HT-29 | 0.0812 | | |
| | | | Du145 | 0.016 | | |
| 1093 | 630.9845 | [structure] | mda | >30 | | |
| | | | | 19.2* | | |
| 1096 | 594.8446 | [structure] | MDA | 0.094* | mda | 190 |
| | | | | | | 26.5 |
| 1097 | 455.6678 | [structure] | MDA | 0.0397 | mda | 1200 |
| | | | MDA | 0.117 | | |
| | | | MDA | 0.0817 | mda | 5.24 |
| 1098 | 590.8348 | [structure] | MDA | 2.1 | mda | 1200 |
| | | | | | | 5.52 |
| | | | | | | >1000 |
| | | | | | | 263 |

| | | | | | | 180 |
|---|---|---|---|---|---|---|
| 1100 | 545.75 | [structure] | MDA | 0.0195* | mda | 0.588 |
| | | | MDA | 0.00485 | | |
| | | | PC-3 | 0.0164 | | |
| | | | MDA | 0.0105* | | |
| | | | MCF-7 | 0.0196 | | |
| | | | CaCo | 0.00663 | | |
| 1101 | 513.7292 | [structure] | MDA | 0.0793 | pc-3 | 3.0 | >300 |
| 1107 | 314.5186 | [structure] | | 0.182 | mda | 6.17 | >300 |
| | | | MDA | | mda | | 63 |
| 1111 | 565.7189 | [structure] | MDA | 0.19 | | | |
| 1113 | 564.8402 | [structure] | MDA | 0.0167 | mda | 1.44 | 380 |
| 1114 | 559.0029 | [structure] | MDA | 0.073 | pc-3 | 1.43 | 320 |
| 1115 | 491.7012 | [structure] | | | mda | 1.59 | >300 |
| | | | | | pc-3 | | >300 |
| 1116 | 491.7012 | [structure] | | | mda | 315 | >300 |
| | | | | | pc-3 | | >300 |
| 1119 | 469.6949 | [structure] | MDA | 0.0568* | mda | 315 | >300 |
| | | | | | pc-3 | 5.1 | >10 |
| 1120 | 415.6245 | [structure] | MDA | 0.0687* | mda | 11.5 | >10 |

| ID | Mass | Structure | Cell | Value | Value2 | Value3 |
|---|---|---|---|---|---|---|
| 1122 | 343.5604 | | MDA | 0.248 | | |
| 1122 | 657.3438 | | MDA | 0.397 | | |
| | | | MDA | 0.012 | 5.20 | 255 |
| | | | MDA | 0.0136 | 1.23 | 530 |
| | | | PC-3 | 0.038 | | |
| | | | Du145 | 0.0985 | | |
| 1124 | 576.8513 | | MDA | 0.0178 | 13.2 | >300 |
| 1129 | 529.7915 | | MDA | 0.0466 | 68.2 | >300 |
| | | | MDA | 0.17* | | |
| 1135 | 425.6633 | | | 0.167* | 71.3 | >300 |
| | | | pc-3 | | 29.2 | >300 |
| 1136 | 477.7398 | | mda | 0.0446* | 66.5 | >100 |
| | | | mda | | 9.68 | >1000 |
| 1149 | 387.5703 | | pc-3 | 0.0344 | 9.23 | >1000 |
| | | | mda | 0.136* | >100 | >100 |
| 1152 | 490.8377 | | pc-3 | 0.0903 | | 99 |
| 1156 | 614.275 | | mda | 0.085 | 1.55 | >100 |
| | | | mda | 0.00955 | 2.56 | >300 |
| | | | pc-3 | | | >300 |
| 1160 | 393.5961 | | MDA | 0.0564* | 45.8 | >300 |
| | | | pc-3 | | | 64 |
| 1161 | 357.5438 | | MDA | >0.3 | >300 | >300 |
| | | | MDA | >1 | >300 | >300 |

FIG. 45b (CONT. 4)

| | | | | | | |
|---|---|---|---|---|---|---|
| 1165 | 607.2209 | | MDA | 0.0143 | mda | <3 | 199 |
| 1174 | 459.66 | | | | pc-3 | <3 | 188 |
| 1175 | 373.5432 | | | | mda | >300 | >300 |
| | | | | | pc-3 | >300 | >300 |
| 1179 | 369.555 | | MDA | 0.061 | pc-3 | 24.7 | >300 |
| | | | | 1>uM | mda | >300 | >300 |
| 1180 | 439.6684 | | MDA | 0.0265 | mda | >300 | >300 |
| | | | | | pc-3 | >300 | >300 |
| 1203 | 244.3832 | | | | | | |
| 1209 | 359.52 | | MDA | >1 | mda | 62 | 277 |
| 1233 | 587.2084 | | MDA | 0.0355* | pc-3 | 72 | 227 |
| | | | MDA | 0.0185* | mda | 1.9 | >300 |
| 1234 | 506.7159 | | MDA | 0.0565 | pc-3 | 0.56 | >300 |
| | | | | | mda | 1.6 | >300 |
| 1238 | 364.5792 | | MDA | >1 | pc-3 | 0.87 | >300 |
| | | | | | mda | | 235 |
| 1239 | 392.6333 | | | | pc-3 | | 208 |
| | | | | | mda | | 195 |
| | | | | | pc-3 | | 173 |

*FIG. 45b (CONT. 5)*

| | | | | |
|---|---|---|---|---|
| 1241 | 615.2626 | [structure] | MDA | 0.0262 |
| 1243 | 428.6448 | [structure] | | |
| 1244 | 359.5189 | [structure] | MDA | 0.46 |
| 1245 | 313.4495 | [structure] | | |
| 1254 | 505.666 | [structure] | MDA | 0.0577 |
| 1281 | 392.6333 | [structure] | MDA | >1 |
| 1298 | 413.5865 | [structure] | | |
| 1305 | 348.5361 | [structure] | | |
| 1315 | 477.4338 | [structure] | | |
| 1340 | 644.3043 | [structure] | | |

FIG. 45b (CONT. 6)

| N1-MONOSUBSTITUTED POLYAMINES: AMIDES, AMINO ALKYL | | | | | | | |
|---|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO | IC50 |
| 1091 | 301.4791 |  | | | mda | | >100 |
| 1094 | 315.5062 |  | MDA | 0.075 | mda | 18 | >300 |
| | | | MDA | 0.117 | mda | 51.5 | >1000 |
| | | | MDA | 0.040 | mda | | |
| | | | MDA | 0.028- | mda | 54 | >300 |
| | | | MDA | 0.043 | | | |
| 1110 | 244.3832 |  | MDA | 0.162 | MDA | | |
| 1121 | 343.5604 |  | MDA | 0.190 | MDA | >300 | >300 |
| | | | MDA | 0.64 | | | |
| 1122 | 343.5604 |  | MDA | 0.5 | PC-3 | | >300 |
| | | | MDA | 0.248 | | | |
| 1126 | 301.4791 |  | MDA | 0.397 | mda | | |
| | | | MDA | >10 | | | >100 |
| 1150 | 287.452 |  | MDA | 0.043* | mda* | | >100 |
| 1177 | 273.4249 |  | MDA | 0.0756* | mda | >300 | >300 |
| | | | PC-3 | 0.0636 | DC-3 | <3 | >300 |
| | | | Du145 | 0.147 | MDA | >100 | >100 |
| | | | | | PC-3 | 2.85 | >100 |
| 1197 | 301.4791 |  | MDA | 0.39 | MDA | | >300 |
| | | | | | PC-3 | >300 | 460 |

| 1198 | 301.4791 | [structure] | MDA | 0.424 | MDA | >300 | >300 |
|---|---|---|---|---|---|---|---|
| | | | | | PC-3 | 299 | >300 |

| N1-MONOSUBSTITUTED POLYAMINES: AMIDES, PROTECTED AMINO ACID HEAD GROUP | | | | | | | |
|---|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO | IC50 |
| 1117 | 359.5161 | | MDA | 0.232* | mda | | >100 |
| 1118 | 488.679 | | | | pc-3 | 22.64 | >300 |
| 1127 | 458.6526 | | | | mda | 50.4 | >100 |
| 1147 | 481.7281 | | MDA | 0.098* | mda | >100 | >100 |
| 1151 | 416.5685 | | MDA | >1 | | | |
| 1153 | 430.5955 | | mda | 0.156 | | | |
| 1155 | 401.5974 | | MDA | 0.258 | | | |
| 1158 | 399.5815 | | MDA | 0.183 | | | |
| 1162 | 433.6614 | | MDA | 0.0913 | | | |
| | | | MDA | 0.083 | | | |

| | | | | | | | |
|---|---|---|---|---|---|---|---|
| 1170 | 521.7061 | [structure] | MDA | | mda | >300 | >300 |
| 1172 | 555.7673 | [structure] | MDA | >1 | pc-3 | >300 | >300 |
| | | | | 37.1 | mda | | 20 |
| 1176 | 373.5432 | [structure] | MDA | 0.0418 | pc-3 | >300 | 20 |
| 1176 | 373.5432 | [structure] | MDA | | mda | | >300 |
| 1176 | 373.5432 | [structure] | MDA | 0.0418 | pc-3 | 14.0 | >300 |
| | | | MDA | | mda | >300 | >300 |
| 1176 | 373.5432 | [structure] | MDA | 0.0418 | pc-3 | 14.0 | >300 |
| | | | MDA | | mda | >300 | >300 |
| 1176 | 373.5432 | [structure] | MDA | 0.0418 | pc-3 | 14.0 | >300 |
| | | | MDA | | mda | >300 | >300 |
| 1176 | 373.5432 | [structure] | MDA | 0.465 | pc-3 | 14.0 | >300 |
| | | | MDA | | MDA | 52 | >300 |
| 1189 | 493.6956 | [structure] | | | PC-3 | 100 | >300 |

*FIG. 45d (CONT.1)*

| | | | | | | |
|---|---|---|---|---|---|---|
| 1193 | 415.6245 | 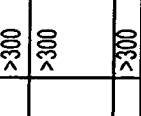 | MDA | | pc-3 | >300 |
| | | | | | MDA | 89.2 | >300 |
| 1195 | 401.5974 | 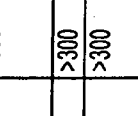 | MDA | 0.265 | PC-3 | 91.9 | >300 |
| | | | | 0.271 | MDA | 37.9 | >300 |
| 1199 | 564.775 | 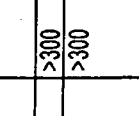 | MDA | 0.060* | PC-3 | 70.9 | >300 |
| | | | | | MDA | 15.5 | >300 |
| 1200 | 464.6567 | 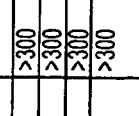 | MDA | 0.039 | PC-3 | 9.20 | >300 |
| | | | | | MDA | 29.8 | >300 |
| 1201 | 430.6392 | 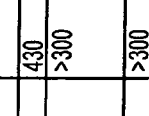 | MDA | 0.191 | MDA | 41.3 | >300 |
| | | | | | PC-3 | 7.87 | >300 |
| | | | | | PC-3 | 8.51 | >300 |
| | | | | | MDA | 36.9 | >300 |
| 1205 | 403.5697 | 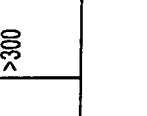 | | | pc-3 | 16.9 | 430 |
| | | | | | mda | 100 | >300 |
| 1206 | 393.5773 |  | MDA | 0.1094 | pc-3 | >300 | >300 |
| | | | | | mda | 19 | >300 |
*FIG. 45d (CONT.2)*

| | | pc-3 | 67 | >300 |
|---|---|---|---|---|
| 1219 | 387.5703 | | | |
| 1221 | 550.7479 | | | |
| 1222 | 450.6296 | | | |
| 1223 | 416.6121 | | | |
| 1229 | 415.6245 | | | |
| 1231 | 415.6245 | | | |
| 1259 | 760.9417 | | | |

FIG. 45d (CONT.3)

N1-MONOSUBSTITUTED POLYAMINES: AMIDES, NATURAL ALPHA-AMINO ACID HEAD GROUP

| ID | MOL WEIGHT | STRUCTURE | TRANSPORT>CELL LINE | Ki | GROWTH INHIBITION>CELL LINE | HALF EFFECT DRUG | DFMO IC50 |
|---|---|---|---|---|---|---|---|
| 1095 | 388.5607 | 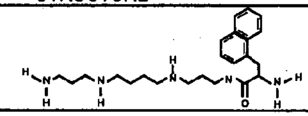 | MDA | 0.073 | mda | 5.3 | >300 |
| | | | | | mda | | 560 |
| | | | | | pc-3 | 8.44 | >1000 |
| | | | MDA | 0.011- | mda | 14.05 | >300 |
| 1125 | 259.3978 | 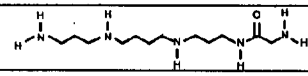 | MDA | 0.07 | mda | 30.0 | >100 |
| 1131 | 316.4501 | 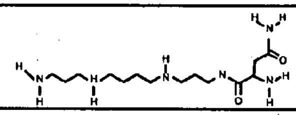 | MDA | 0.1036* | | | |
| | | | | | pc-3 | 57.0 | >300 |
| | | | | | mda | 81.97 | >1000 |
| | | | | | mda | 113 | >300 |
| | | | | | pc-3 | 57 | >300 |
| 1148 | 349.5237 | 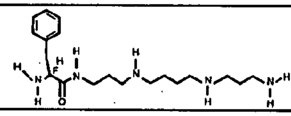 | MDA | 0.214* | mda | | >100 |
| 1154 | 330.4772 | 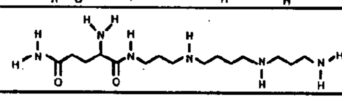 | MDA | 0.047 | mda | >300 | >300 |
| 1157 | 301.4791 | 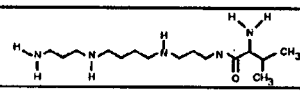 | MDA | 0.160* | pc-3 | >300 | |
| | | | | | mda | 5.58 | |
| | | | MDA | 0.0392 | pc-3 | 14.35 | >300 |
| | | | PC-3 | 0.149 | mda | 26.42 | >300 |
| | | | Du145 | 0.109 | PC-3 | 3.86 | >300 |
| | | | MDA | 0.0514 | pc-3 | 5.28 | |
| | | | Du145 | 0.0467 | | | |

FIG. 45e

| | | | | | |
|---|---|---|---|---|---|
| 1159 | 299.4632 | | MDA | 0.0255 | 92.8 | >300 |
| 1164 | 333.5431 | | MDA | 0.0499 | 16.5 | 81 |
| | | | MDA | 0.21.5-50 | >100 | >100 |
| | | | | | 12.1 | >100 |
| 1171 | 331.462 | | MDA | 0.0335 | mda | >300 |
| | | | | | >300 | >300 |
| | | | MDA | 0.0765 | dc-3 | >300 |
| | | | MDA | | 300 | |
| 1173 | 365.5231 | | MDA | 0.13 | PC-3 | >300 |
| | | | MDA | 0.0768 | MDA | >300 |
| 1178 | 273.4249 | | MDA | 0.0526* | PC-3 | >300 |
| | | | | | mda | >300 |
| 1186 | 317.4349 | | MDA | 0.167 | dc-3 | >300 |
| | | | | | MDA | 300 |
| 1187 | 289.4243 | | MDA | 0.38 | PC-3 | 213 |
| | | | MDA | 0.0453 | MDA | 25.5 |
| 1202 | 330.5209 | | MDA | 0.0295 | PC-3 | 20.8 |
| | | | | | MDA | 4.75 |
| | | | PC3 | 0.748 | PC-3 | 5.30 |
| | | | MDA | 0.147 | dc-3 | 1.7 |
| | | | MDA | 0.032* | | |
| | | | MDA | 0.05 | | >300 |
| | | | HT-29 | 0.185 | | |

FIG. 45e (CONT.2)

| | | | | | | |
|---|---|---|---|---|---|---|
| 1207 | 303.4514 | [structure] | MDA | 0.13 | mda | 6.5 | >300 |
| 1228 | 315.5062 | [structure] | MDA | 0.124 | pc-3 | 6.2 | >300 |
| | | | | | mda | 9.1 | >300 |
| 1230 | 315.5062 | [structure] | MDA | 0.0323 | pc-3 | 4.0 | >300 |
| | | | | | mda | >300 | >300 |
| 1237 | 374.6181 | [structure] | MDA | 0.113 | pc-3 | 6.2 | >300 |
| | | | | | mda | >300 | >300 |
| 1260 | 358.5343 | [structure] | MDA | 0.099 | pc-3 | >300 | >300 |
| | | | | | mda | 6.80 | >100 |
| | | | | | pc-3 | 3.04 | >100 |

| ID | MOL WEIGHT | STRUCTURE | TRANSPORT>CELL LINE | Ki | GROWTH INHIBITION>CELL LINE | HALF EFFECT DRUG DFMO | IC50 |
|---|---|---|---|---|---|---|---|
| 1188 | 313.4466 | 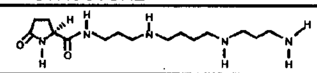 | MDA | >1 µM | MDA | | 320 |
| 1194 | 315.5062 | 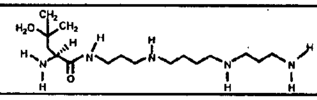 | MDA | 10.6 | PC-3 | | 214 |
| | | | MDA | 0.0727* | MDA | 5.32 | >300 |
| | | | | | PC-3 | 7.51 | >300 |
| | | | | | MDA | 16.19 | >300 |
| | | | | | PC-3 | 1.82 | >300 |
| 1196 | 301.4791 | 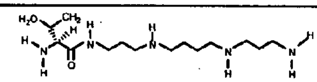 | MDA | 0.0483 | MDA | 9.03 | >300 |
| 1220 | 287.452 | 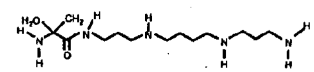 | MDA | 0.16 | PC-3 | 8.01 | >300 |
| | | | | | | 8.0 | >300 |
| 1224 | 316.4938 | 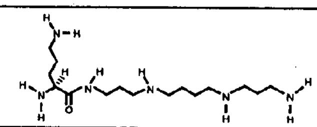 | MDA | 0.0432 | pc-3 | 2.4 | >300 |
| | | | | | pc-3 | 3.0 | >300 |
| 1227 | 355.5715 | 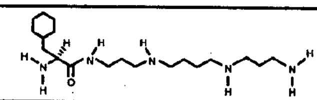 | MDA | 0.0515 | mda | 4.37 | >300 |
| | | | MDA | 0.241 | mda | 7.8 | >30 |
| 1309 | 388.5607 | 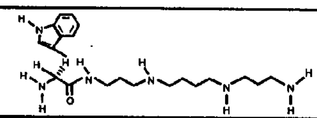 | | | pc-3 | 0.95 | >30 |

FIG. 45g

| N1-MONOSUBSTITUTED POLYAMINES: AMIDES, AMINO ACID DERIVATIVE HEAD GROUP | | | | | | |
|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO IC50 |
| 1304 | 418.6337 | | | | mda | 85 >300 |
| 1310 | 510.7726 | | | | pc-3 | 15.0 244.8 |
| | | | | | mda | 4.2 |
| 1355 | 145.206 | | | | pc-3 | 1.7 |
| | | | | | mda | >10000 |

FIG. 45h

N1-MONOSUBSTITUTED POLYAMINES: SULFONAMIDES

| ID | MOL WEIGHT | STRUCTURE | TRANSPORT>CELL LINE | Ki | GROWTH INHIBITION>CELL LINE | HALF EFFECT | DRUG DFMO IC50 |
|---|---|---|---|---|---|---|---|
| 1001 | 435.6365 | 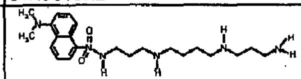 | MDA | .039 | MDA | 20 | 600 |
| 1003 | 421.6094 | 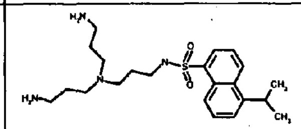 | A172 MDA | .08 1 | A172 MDA | 100uM | >300 |
| 1005 | 318.3975 | 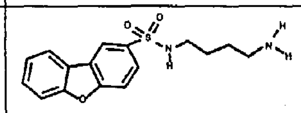 | A172 | 23 | A172 | | 28 uM |
| 1006 | 446.6164 | 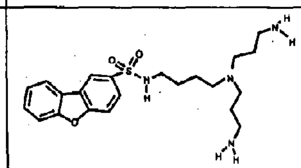 | mda | 1.46 | MDA A172 | | 40 uM 20 |
| 1007 | 302.4389 | 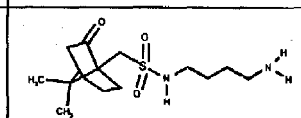 | A172 | 60 | MDA mda | | 50 >300 |
| 1008 | 416.6308 | 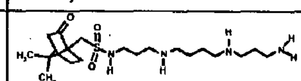 | MDA | >10 | MDA | | >300 |
| 1010 | 442.6282 | 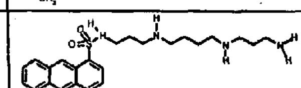 | MDA | 0.110 | MDA | 1.7 | 20 |
| | | | A172 | 0.082 | MDA | 1.05 | 18 |

| | | | | | |
|---|---|---|---|---|---|
| 1011 | 435.6365 | ☒ | MDA | 0.066* | MDA | 6.0 | 50 |
| 1012 | 421.6094 | ☒ | MDA | >10 | MDA | <30 | 50 |
| 1013 | 435.6365 | ☒ | MDA | 3.5 | MDA | | 150 |
| 1014 | 421.6094 | ☒ | A172<br>MDA | 1.34<br>>10 | MDA | 13.4 | 50 |
| 1015 | 489.6881 | ☒ | MDA<br>A172 | 2.9<br>1.6 | MDA | | 100 |
| 1016 | 475.661 | ☒ | MDA | >10 | MDA<br>pc-3<br>caco-2<br>cem<br>MDA | | 15<br>>30<br>18.2<br>>30<br>13 |
| 1017 | 392.5676 | ☒ | MDA<br>A172 | .187<br>.24 | MDA | 14.2 | 50 |

FIG. 45h (CONT.1)

| # | MW | Structure | | | | |
|---|---|---|---|---|---|---|
| 1018 | 278.3758 | | mda | >30 | | 120 |
| 1019 | 392.5676 | | MDA | 0.2* | MDA | 50 7.5 |
| 1020 | 379.5281 | | A172 MDA | 0.37 >30 | MDA MDA | 50 4.4 110 |
| 1023 | 466.6505 | | MDA | .091 | MDA | 22 |
| 1024 | 407.5823 | | A172 MDA | .075 5.4 | MDA | 50 |
| 1025 | 365.501 | | MDA | 4.3 | MDA | >300 |
| 1026 | 364.5135 | | MDA | 2.7 | MDA | 50 |
| 1027 | 322.4322 | | MDA | >10 | MDA | >300 |
| 1028 | 421.6094 | | MDA | 11.4 | MDA | 50 |

FIG. 45h (CONT.2)

| ID | MW | Structure | | | | | |
|---|---|---|---|---|---|---|---|
| 1029 | 379.5281 | (structure) | MDA | | | | >300 |
| 1030 | 458.0054 | (structure) | MDA | | | 125 | >250 |
| 1031 | 393.5552 | (structure) | MDA | | | <10 | >300 |
| 1034 | 444.9505 | (structure) | MDA | | | <3 | 50 |
| 1036 | 430.5735 | (structure) | MDA | 3.4 | MDA | | |
| | | | | 0.08 | MDA | | |
| | | | | 0.43 | MDA | | |
| | | | | 0.24 | MDA | | |
| | | | | 0.84 | mda / MDA | 8.7 | 50 |
| 1041 | 432.5893 | (structure) | MDA | 0.066 | MDA | .95 | >300 |
| | | | | | pc-3 | | 12 |
| | | | | | caco-2 | | 6.2 |
| | | | | | cem | | 16.1 |
| | | | | | mda | | 0.79 |
| | | | | | pc-3 | | 53.0 |
| | | | | | mda | | 12.4 |
| | | | | | pc-3 | | 46.1 |
| 1044 | 516.129 | (structure) | MDA | 0.156* | MDA | 3 | 6.5 |
| | | | MDA | 0.0582 | mda | <3.0 | 180 |
| | | | MDA | 0.130 | | | 190 |
| | | | MDA | 0.13 | | | |
| 1045 | 425.6192 | (structure) | MDA | 0.228 | MDA | 13 | 180 |
| | | | MDA | 0.164 | mda | 7.3 | 140 |
| | | | | 0.32 | | | |

*FIG. 45h (CONT.3)*

| | | | | | | |
|---|---|---|---|---|---|---|
| 1046 | 472.6979 | (structure) | MDA | 0.4 | mda | 6.92 | 58 |
| 1047 | 488.6944 | (structure) | MDA | 0.0677 | pc-3 | | 34.8 |
| | | | | | caco-2 | | >30 |
| | | | | | cem | | 8.9 |
| 1048 | 400.5686 | (structure) | MDA | 0.375 | mda | 7.3 | 170 |
| 1049 | 423.0024 | (structure) | MDA | 0.177 | | | |
| | | | MDA | 0.421 | mda | 26.7 | >300 |
| 1050 | 494.0602 | (structure) | MDA | >3 | mda | | >300 |
| 1051 | 481.684 | (structure) | MDA | 0.108 | MDA | 2.26 | 140 |
| | | | MDA | 0.0537 | | | |
| | | | MDA | 0.28 | mda | 6.5 | >300 |
| 1052 | 342.5071 | (structure) | MDA | 0.076 | | | |
| | | | MDA | 0.16* | mda | 30 | >300 |
| 1054 | 445.8422 | (structure) | MDA | 0.025 | MDA | <3.0 | 50 |
| | | | | 0.0829 | mda | 7.89 | 20 |
| | | | | | pc-3 | | 19.8 |
| | | | | | caco-2 | | 27.1 |
| | | | | | cem | | 2.6 |
| 1057 | 434.7334 | (structure) | MDA | 0.17 | mda | | 100 |

*FIG. 45h (CONT.4)*

| | | | | | |
|---|---|---|---|---|---|
| 1058 | 484.7503 | 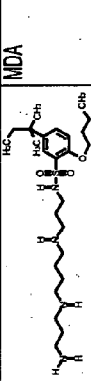 | MDA | 0.17* | mda | 6 |
| | | | | | pc-3 | 5.9 |
| | | | | | caco-2 | 14.8 |
| | | | | | cem | 0.71 |
| 1070 | 587.7877 | 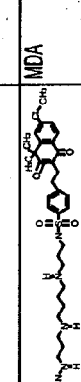 | MDA | >10 | mda | 13 |
| | | | | | pc-3 | >30 |
| | | | | | caco-2 | >30 |
| | | | | | cem | >30 |
| 1074 | 437.606 | 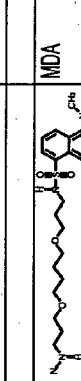 | MDA | >30 | MDA | |
| 1075 | 433.6206 | 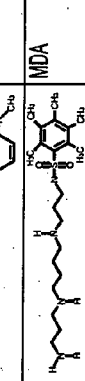 | MDA | >100 | | |
| 1082 | 412.6426 |  | MDA | >3 | mda | 140 |
| 1088 | 278.3758 | 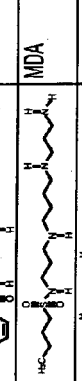 | mda | 5.4* | | |
| 1103 | 488.6944 |  | MDA | 0.067 | mda | 58 | 3.5 |
| 1105 | 557.6804 | | MDA | 0.083 | mda | 44 |
| 1106 | 356.5342 |  | MDA | 0.094 | mda | 160 |
| 1108 | 322.5167 | | MDA | 0.19 | mda | 150 |
| 1130 | 294.4625 |  | MDA | 0.22 | mda | >300 | >300 |
*FIG. 45h (CONT.5)*

*FIG. 45h (CONT.6)*

| N1-MONOSUBSTITUTED POLYAMINES: N1-MONOSUBSTITUTED AMINES | | | | | | |
|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO IC50 |
| 1004 | 372.4712 | | MDA<br>A172 | 2.2<br>3 | MDA | 5 |
| 1350 | 316.5374 | | | | | |

FIG. 45i

| N1-MONOSUBSTITUTED POLYAMINES: OTHER | | | TRANSPORT>CELL LINE | Ki | GROWTH INHIBITION>CELL LINE | HALF EFFECT DRUG DFMO | IC50 |
|---|---|---|---|---|---|---|---|
| ID | MOL WEIGHT | STRUCTURE | | | | | |
| 1021 (UREA) | 421.5906 | | MDA | 0.44 | MDA | 8.2 | 35 |
| 1042 (UREA) | 569.7752 | | A172 | .04* | | | |
| 1071 | 641.0454 | | MDA | 1 | MDA | 14.8 | 100 |
| 1109 (UREA) | 563.8118 | | MDA | 0.0674 | pc-3 | 30 | >100 |
| | | | MDA | 0.090 | mda | 95 | >100 |
| 1295 (THIOUREA) | 591.735 | | MDA | >3 | | | |

FIG. 45j

N1,N12-DISUBSTITUTED POLYAMINES: N1,N12-DIACYLPOLYAMINE

| ID | MOL WEIGHT | STRUCTURE | TRANSPORT>CELL LINE | Ki | GROWTH INHIBITION>CELL LINE | HALF EFFECT DRUG DFMO | IC50 |
|---|---|---|---|---|---|---|---|
| 1099 | 895.2488 | 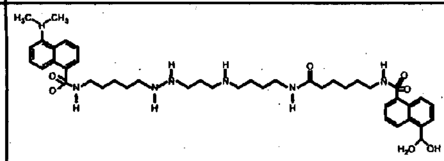 | MDA | 0.54 | mda | | 64 |
| 1132 | 628.9035 | 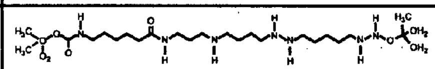 | MDA | 11.6* | | | |
| 1133 | | 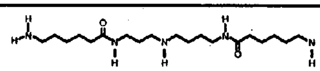 | MDA | 8.44* | MDA | | |
| 1168 | 324.4702 | 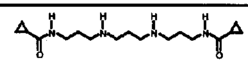 | | | mda | | >100 |
| 1242 | 554.867 | 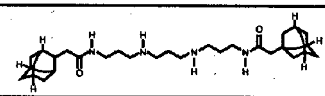 | MDA | 7.4 | h157 | | >100 |
| | | | | | mda | | 45.8 |
| 1250 | 1042.21 | 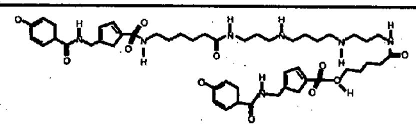 | MDA | 0.38 | pc-3 | | 20.5 |
| 1258 | 516.6923 | 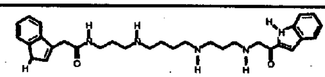 | MDA | 0.44 | | 15.0 | |
| 1282 | 582.9211 | 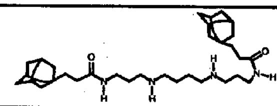 | | | mda | | 59.2 |

*FIG. 46a*

| N1,N12-DISUBSTITUTED POLYAMINES:N1,N12-ACYLSULFONYLPOLYAMINES | | | | | | | |
|---|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO | IC50 |
| 1266 | 763.4255 | | | | | | |
| 1276 | 522.7589 | | MDA | 0.104 | | | |
| 1280 | 687.3267 | | | | | | |

FIG. 46b

N1,N12-DISUBSTITUTED POLYAMINES: N1,N12-DIALKYLAMINEPOLYAMINES

| ID | MOL WEIGHT | STRUCTURE | TRANSPORT>CELL LINE | Ki | GROWTH INHIBITION>CELL LINE | HALF EFFECT DRUG DFMO IC50 |
|---|---|---|---|---|---|---|
| 1247 | 534.53 | 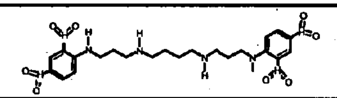 | | | mda | 0.74 |
| | | | | | pc-3 | 0.61 |
| | | | | | mda | 1.27 |
| | | | | | pc-3 | 0.84 |
| 1279 | 520.5061 | 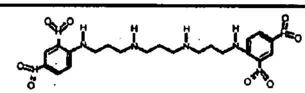 | | | mda | 21.3 |
| | | | | | pc-3 | 33.2 |
| | | | | | mda | 2.0 |
| 1352 | 717.0217 | 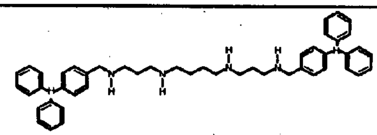 | | | pc-3 | 1.9 |

FIG. 46c

| N1,N12-DISUBSTITUTED POLYAMINES: N1,N12-ACYLALKYLAMINEPOLYAMINE | | | | | | |
|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO | IC50 |
| 1270 | 544.7001 | | | | mda | | 161 |
| | | | | | pc-3 | | 104 |

| N1,N12-DISUBSTITUTED POLYAMINES: N1,N12-DISULFONYLPOLYAMINE | | | | | | | |
|---|---|---|---|---|---|---|---|
| ID | MOL WEIGHT | STRUCTURE | TRANSPORT>CELL LINE MDA | Ki | GROWTH INHIBITION>CELL LINE | HALF EFFECT DRUG DFMO | IC50 |
| 1278 | 829.91 | | | 0.19 | | | |
| 1293 | 662.8332 | | | | mda | | 2.0 |
| 1321 | 510.7229 | | | | pc-3 / mda / pc-3 | | 1.9 / 2.03 / 1.81 |
| 1322 | 648.8929 | | | | mda / pc-3 / mda | | 0.60 / 0.51 / 55.9 |
| 1323 | 598.7916 | | | | pc-3 / mda | | 25.6 / 9.4 |
| 1328 | 775.0434 | | | | pc-3 / mda | | 15.2 / >300 |
| 1329 | 494.7202 | | | | pc-3 | | 147 |

| N1, N12-DISUBSTITUTED POLYAMINES: N1, N12-SULFONYLALKYLAMINEPOLYAMINE | | | | | | | |
|---|---|---|---|---|---|---|---|
| ID | MOL WEIGHT | STRUCTURE | TRANSPORT>CELL LINE | Ki | GROWTH INHIBITION>CELL LINE | HALF EFFECT DRUG DFMO | IC50 |
| 1349 | 598.6832 |  | | | | | |

POLYAMINE LEVELS (pmol/MILLION CELLS) IN MDA CELLS AFTER EXPOSURE TO ORI 1202 (30μM)

| ORI 1202 | 0 | BACKGROUND ≤1 MIN. | 10 MIN. | 30 MIN. | 1 HR. | 2 HR. | 6 HR. |
|---|---|---|---|---|---|---|---|
|  |  | 32.5 (1X) | 198.5 (6.1X) | 52.2 (1.6X) | 40.2 | 85.3 | 48.5 (1.5X) |
| SPM | 591.7 | 606.8 (1X) | 1955.2 (3.2X) | 1038.2 (1.7X) | 1071.17 | 1095.4 | 935.8 (1.5X) |
| SPD | 398.6 | 345.2 (1X) | 358.3 (1.0X) | 529.2 (1.5X) | 554.6 | 591.8 | 519.5 (1.5X) |
| PUT | 217.5 | 180.2 (1X) | 217.9 (1.2X) | 269.2 (1.5X) | 279.7 | 291.6 | 318.5 (1.8X) |

FIG. 58

POLYAMINE ANALOGUES AS THERAPEUTIC AND DIAGNOSTIC AGENTS

RELATED APPLICATIONS

This is a continuation-in-part of U.S. Ser. No. 09/341,400, filed Sep. 3, 1999, now U.S. Pat. No. 6,172,261 which is a continuation of PCT/US98/14896 filed Jul. 15, 1998, which claims benefit of priority from U.S. Provisional Application 60/052,586, filed Jul. 15, 1997; 60/065,728, filed Nov. 14, 1997; and 60/085,538, filed May 15, 1998; all of which are hereby incorporated by reference as if fully set forth.

FIELD OF THE INVENTION

The invention in the field of chemistry and biochemistry relates to the synthesis and use of novel polyamine transport (PAT) inhibitor compounds with pharmacological or agricultural uses and as probes for biochemical assays or for purification of selected polyamine binding targets. As drugs, these compounds are used to treat disorders of undesired cell proliferation, primarily cancer, alone or combined with other agents such as polyamine synthesis inhibitors.

The invention also relates to the synthesis and use of such novel polyamines as part of combinatorial libraries. These libraries are used to discover compositions that inhibit PAT and/or that bind to a cellular polyamine transporter (PATr). Various members of these libraries or compounds discovered through use of the libraries have utility as drugs, agricultural chemicals, and as probes.

BACKGROUND OF THE INVENTION

Decades of research on the myriad of biological activities that the polyamines, putrescine, spermidine and spermine play in cellular processes have shown the profound role they play in life (Cohen, S. S., "A Guide to the Polyamines" 1998, Oxford University Press, New York). As polycations at physiological pH, they bind tightly to and strongly modulate the biological activities of all of the anionic cellular components. Specific and strong interactions have been associated with DNA and RNA together with their associated chromatin proteins (Tabor, H. et al. 1,4-Diaminobutrane (putrescine), spermidine, and spermine. *Ann Rev. Biochem.* 1976, 45, 285–306; Matthews, H. R. Polyamines, chromatin structure and transcription. *BioEssays,* 1993, 15, 561–566). Spermine has been shown to function directly as a free radical scavenger that protects DNA from insults by reactive oxygen species (Ha, H. C. et al. *Proc. Natl. Acad. Sci. USA,* 1998, 95, 11140–11145). Specific interactions of multicationic polyamines with microtubules has been recently shown (Wolff, J. Promotion of Microtubule Assembly by Oligocations: Cooperativity between Charged Groups. *Biochemistry,* 1998, 37, 10722–10729; Webb, H. K. et al., *J. Med. Chem* 1999, in press). Allosteric regulation of membrane-bound enzymes including acetylcholinesterase has been shown (Kossorotow, A. et al. Regulatory effects of polyamines on membrane-bound acetylcholinesterase. *Biochem. J.* 1974, 144, 21–27). Polyamines have a direct influence on many neurotransmitter receptors and ion channels (Carter, C. The Neuropharmacology of Polyamines, 1994, Academic Press, San Diego, Calif.; Williams, K. Interaction of polyamines with ion channels, *Biochem. J.,* 1997, 325, 289–297). Specific polyamine binding sites have also been demonstrated for the NMDA receptor complex (Ransom, R. W. et al. Cooperative modulation of [$^3$H]MK-801 Binding to the N-Methyl-D-Aspartate Receptor-Ion Channel Complex by L-Glutamate, Glycine, and Polyamines. *J. Neurochem.* 1988, 51, 830–836; Williams, K. et al. Minireview: Modulation of the NMDA receptor by polyamines. *Life Sci* 1991, 48, 469–498).

Many stimuli involved in both normal and neoplastic growth activate the polyamine biosynthetic pathway. A great number of multidisciplinary studies have shown that the intracellular concentrations of the polyamines is highly regulated at many steps in their biosynthesis, catabolism and transport. The fact that cells contain such complex apparatus for the tight control of the levels of these molecules shows that only a very narrow concentration range is tolerated. Ornithine decarboxylase (ODC), the rate-limiting enzyme in polyamine biosynthesis, catalyzes the production of putrescine from its precursor ornithine. This enzyme, with a very short biological half-life, is one of the most inducible mammalian enzymes known (Russell, D. et al. Amine synthesis in rapidly growing tissues: ornithine decarboxylase activity in regenerating rat liver, chick embryo, and various tumors. *Proc. Natl. Acad. Sci. USA* 1968, 60, 1420–1427). Many biological stimuli involved in cellular growth have been shown to induce this enzyme and a distinct growth advantage is gained by induction of ODC (Alhonen-Hongisto, L. et al. Tumourigenicity, cell-surface glycoprotein changes and ornithine decarboxylase gene pattern in Ehrlich ascites-carcinoma cells. *Biochem. J.* 1985, 229, 711–715). An increase in the activity of ODC has been associated with tumor growth (Jänne, J. et al. Polyamines in rapid growth and cancer. *Biochim. Biophys. Acta* 1978, 473, 241–493; Scalabrino, G. et al. Polyamines in mammalian tumors. Part I. *Adv. Cancer Res.* 1981, 35, 151–268; Scalabrino, G. et al. Polyamines in mammalian tumors. Part II. *Adv. Cancer Res.* 1982, 36, 1–102). Feedback inhibition of ODC activity is mediated by ODC-antizyme protein. Following elevation of polyamine concentrations, a polyamine-stimulated +1 frameshift of the ODC-antizyme mRNA reading frame causes elevation of this ODC-inhibiting protein (Hayashi, S. et al. Ornithine decarboxylase antizyme: a novel type of regulatory protein. *TIBS,* 1996, 21, 27–30; Matsufuji, S. et al. *EMBO Journal,* 1996, 15, 1360–1370). The ODC-antizyme protein binds to ODC with high affinity to form an inactive complex that is then tagged for degradation in an ATP-dependent fashion by the 26S proteosome (Heller, J. S. et al. *Proc. Natl. Aced. Sci. USA* 1976, 73,1858–1862; Murakami, Y. et al. Ornithine decarboxylase is degraded by the 26S proteosome without ubiquitination. *Nature,* 1992, 360, 597–599). ODC-antizyme also represses the polyamine uptake system of cells (Suzuki, T. et al. Antizyme protects against abnormal accumulation and toxicity of polyamines in ornithine decarboxylase-overproducing cells. *Proc. Natl. Acad. Sci. USA.* 1994, 91, 8930–8934).

The polyamine catabolism pathway is important to prevent the toxic effects of excess polyamines on cells (Seiler, N. Functions of polyamine acetylation. *Can. J. Physiol. Pharmacol.* 1987, 65, 2024–2035; Seiler, N. Polyamine oxidase, properties and functions. *Progress in Brain Res.* 1995, 106, 333–344). This pathway is used by the cell to interconvert the various polyamines and to eliminate excess polyamines before they reach toxic levels. This pathway introduces no additional carbon precursors into the polyamine pool.

Polyamine transport into mammalian cells is energy and temperature dependent, saturable, carrier mediated and operates against a substantial concentration gradient (Seiler, N. et al. Polyamine transport in mammalian cells. *Int. J. Biochem* 1990, 22, 211–218; Khan, N. A.; Quemener, V. et al. Characterization of polyamine transport pathways, in *Neu-* ropharmacology of Polyamines (Carter, C., ed.), 1994, Academic, San Diego, pp. 37–60). Ample experimental proof exists that polyamine concentration homeostasis is mediated via this transport system. Changes in the requirements for polyamines in response to growth stimulation is reflected by increases in the transport activity. Stimulation of human fibroblasts to cell proliferation by serum or epidermal growth factor was followed by an 18–100 fold increase in the uptake of putrescine (DiPasquale, A. et al. Epidermal growth factor stimulates putrescine transport and ornithine decarboxylase activity in cultures human fibroblasts. *Exp. Cell Res.* 1978, 116, 317–323; Pohjanpelto, P. Putrescine transport is greatly increased in human fibroblasts initiated to proliferate *J. Cell Biol.* 1976, 68, 512–520). Tumors have been shown to have an increased rate of putrescine uptake (Volkow, N. et al. Labeled putrescine as a probe in brain tumors. *Science,* 1983, 221, 673–675; Moulinoux, J- P. et al. Biological significance of circulating polyamines in oncology. *Cell. Mol. Biol.* 1991, 37, 773–783). Inhibition of polyamine biosynthesis in cells in culture by α-difluoromethylornithine (DFMO), a well-studied mechanism-based inhibitor of ODC, causes a substantial depletion of intracellular putrescine and spermidine with resultant cell growth inhibition. Upon supplementing the culture media with exogenous polyamines this depletion causes transport activity to rise several-fold (Bogle, R. G. et al. Endothelial polyamine uptake: selective stimulation by L-arginine deprivation or polyamine depletion. *Am. J. Physiol.* 1994, 266, C776–C783; Alhonen-Hongisto, L. et al. Intracellular putrescine deprivation induces uptake of the natural polyamines and methylglyoxal bis(guanylhydrazone). *Biochem. J.* 1980, 192, 941–945). The cells then returned to their original rate of growth.

Several experimental lines of evidence support the conclusion that increased effectiveness of ODC inhibition can be obtained by interfering with the polyamine transport apparatus. A mutant L1210 leukemia cell line was shown to have greatly reduced polyamine transport activity following selection for resistance to methylglycoxal bis(guanylhydrazone) (MGBG), an extremely cytotoxic AdoMetDC inhibitor that is taken up by the same transport system as the polyamines. Mice inoculated with these cells had a much greater response to DFMO treatment (87% increase in median survival time; 13 of 40 mice cured) than mice inoculated with the parental cell line (22% increase in median survival time). See Persson, L. et al. Curative effect of d,1-2-difluoromethylornithine on mice bearing mutant L1210 leukemia cells deficient in polyamine uptake. *Cancer Res* 1988, 48, 4807–4811. A significant source of extracellular polyamines is produced by the microbial flora in the gastrointestinal tract (Sarhan, S. et al. The gastrointestinal tract as polyamine source for tumor growth. *Anticancer Res* 1989, 9, 215–224). When this source of polyamines is removed by decontamination of this flora, DFMO's previous moderate growth inhibitory effects on Lewis lung carcinoma cells or L1210 zenografts is markedly potentiated (Hessels, J. et al. Limitation of dietary polyamines and arginine and the gastrointestinal synthesis of putrescine potentiates the cytostatic effect of a-difluoromethylornithine in L1210 bearing mice. *Int. Symp. Polyamines in Biochemical and Clinical Research*, Sorrento (Italy), 1988, Abstr. P105). An additional source of polyamines is from dietary sources (Bardocz, S. et al. Polyamines in food; implications for growth and health. *J. Biochem Nutr.* 1993, 4, 66–71). By feeding a polyamine-free diet to DFMO-treated nude mice the MCF-7 human breast cancer zenografts contained greatly reduced levels of putrescine in comparison to DFMO treatment alone (Levêque, J. et al. The gastrointestinal polyamine source depletion enhances DFMO induced polyamine depletion in MCF-7 human breast cancer cells in vivo. *Anticancer Res.* 1998, 18, 2663–2668). In additional animal models, complete polyamine deprivation also enhanced DFMO's growth inhibitory effectiveness (Moulinoux, J. P. et al. Inhibition of growth of the U-251 human glioblastoma in nude mice by polyamine deprivation. *Anticancer Res.* 1991, 11, 175–180; Quemener, V. et al. Polyamine deprivation enhances antitumoral efficacy of chemotherapy. *Anticancer Res.* 1992, 12, 1447–1454; Chamaillard, L. et al. Polyamine deprivation prevents the development of tumour-induced immune suppression. *Br. J. Cancer* 1997, 76, 365–370).

The Polyamine Transporter (PATr)

The increased demand for polyamines by rapidly growing, transformed cancer cells is only partially met by an increased rate of synthesis. To exploit this increased need for polyamines, synthesis inhibitors have been sought. Additionally, lowering polyamine concentrations can result in aberrations in chromatin structure leading to cell death or inhibition of proliferation (Quemener, V. et al., *Anticancer Res.* 14:443448, 1994; Porter, C. W. et al., *Cancer Res.* 53:581–586, 1993). It has become increasingly apparent that the initial disappointing results observed in the clinic with polyamine synthesis inhibitors arises from compensatory increases in transport of polyamines by a specific active transport system (Seiler, N. et al., *Int. J. Biochem* 22:211–218, 1990; Seiler, N. et al, *J. Biochem. Cell Biol.* 28:843–861, 1996). The promising results observed in cell culture with a suicide substrate inhibitor of ornithine decarboxylase, α-difluoromethylornithine (DFMO), or with an inhibitor of S-adenosylmethionine decarboxylase, methylglyoxal bis(guanylhydrazone) (MGBG) did not transfer to human clinical trials (Schecter, P. J. et al., In *Inhibition of Polyamine Metabolism. Biological Significance and Basis for New Therapies*; McCann, P. P. et al., eds; 1987, pp 345–364). Since the only two avenues for carbon transfer into polyamine pools are synthesis or transport, simultaneous inhibition of both of these pathways is considered by the present inventors to be a promising anticancer therapeutic approach.

A study confirming the validity of this chemotherapeutic approach used transplanted murine L1210 leukemia cells that were deficient in PAT. Mice transplanted with the wild-type L1210 cancer cells (with intact PAT) died after 12 days, even when treated with DFMO. In contrast, DFMO mice transplanted with PAT-deficient L1210 cells lived longer than 60 days (Ask, A. et al., *Cancer Lett.* 66:29–34, 1992). These authors also showed that treatment of mice harboring wild-type L1210 cells with a combination of (1) DFMO (2) a low polyamine diet and (3) antibiotics (which decrease polyamine production by gut flora) resulted in prolonged survival compared to treatment with DFMO alone.

Augmented PAT into cancer cells promotes cell killing. J. L. Holley et al. (*Cancer Res.* 52:4190–4195, 1992) showed up to a 225-fold increase in cytotoxicity of a chlorambucil-spermidine conjugate compared to chlorambucil alone. A series of nitroimidazole-polyamine conjugates were also effective (Holley, J. L. et al., *Biochem. Pharmacol.* 43:763–769, 1992). Others showed that mice infected with a multi-drug resistant strain of malaria were cured by treatment with a chloroquinoline-putrescine conjugate (Singh, S. et al., *J. Biol. Chem.* 272:13506–13511, 1997). Thus, the effectiveness of cytotoxic compounds could be enhanced by their conjugation with polyamines. These effects may have been due to the exploitation of the PAT system to deliver these compounds into cancer cells.

The gene for the polyamine transport protein has been cloned from *Escherichia coli* and recently from yeast (Kashiwagi, K. et al. *J. Biol. Chem.* 1990, 265, 20893–20897; Tomitori, H. et al. Identification of a gene for a polyamine transport protein in yeast. *J. Biol. Chem.* 1999, 274, 3265–3267). The genes for the mammalian transporter await identification. The transporter from *E. coli* has been crystallized and its X-ray structure has been determined (Sugiyama, S. et al. Crystal structure of PotD, the primary receptor of the polyamine transport system in *Escherichia coli*. *J. Biol. Chem.* 1996, 271, 9519–9525). This structure represents one of only a few but growing number determined for spermidine-binding proteins. Since this structure was determined on a prokaryotic species its use in the design of mammalian transport inhibitors was deemed to be of limited value. Despite this, several insights were obtained and used through analysis of this structure. In addition to the expected presence of carboxylate residues positioned to form salt bridges with the protonated amino groups of spermidine, numerous aromatic residues, especially tryptophan residues appeared to strengthen hydrophobic interactions with the methylene groups of the substrate. Additionally, a $H_2O$ molecule was positioned at one end of spermidine substrate, providing stronger interactions with the ionic residues in this position.

Several researchers have studied the ability of polyamine analogs to inhibit the uptake of $^3$H-spermidine into cells. Bergeron and coworkers studied the effect of addition of different alkyl group substitution on the terminal nitrogen atoms of spermidine or spermine analogs (Bergeron, R. J. et al. Antiproliferative properties of polyamine analogues: a structure-activity study. *J. Med. Chem.* 1994, 37, 3464–3476). They showed larger alkyl groups diminished the ability to prevent uptake of radiolabeled spermidine. They later concluded that increases in the number of methylenes between the nitrogen atoms decreased the ability to compete for $^3$H spermidine uptake (Bergeron, R. J. et al. A comparison of structure-activity relationships between spermidine and spermine antineoplastics *J. Med. Chem.* 1997, 40, 1475–1494). Of greater importance to the present work was their conclusion that the polyamine transport apparatus requires only three cationic centers for polyamine recognition and transport (Porter, C. W. et al. *J. Cancer Res.* 1984, 44, 126–128). Two groups analyzed literature examples of the polyamine analogs ability to inhibit $^3$H spermidine uptake into L1210 cells by CoMFA and QSAR methods (Li, Y. et al. Comparative Molecular field analysis-based predictive model of structure-function relationships of polyamine transport inhibitors in L1210 cells. Cancer Res-1997, 57, 234–239; Xia, C. Q. et al. QSAR analysis of polyamine transport inhibitors in L1210 cells. *J. Drug Target* 1998, 6, 65–77).

Polyamine Transport (PAT) Assays

There is no known high-throughput assay for measuring PAT. A radiochemical assay is used for biochemical analysis of transport and has been used to study PAT in yeast and a variety of mammalian cells (Kakinuma, Y. et al., *Biochem. Biophys. Res. Comm.* 216:985–992, 1995; Seiler, N. et al., *Int. J. Biochem. Cell Biol* 28:843–861, 1996). See, for example Huber, M. et al. *Cancer Res.* 55:934–943, 1995.

The radiometric assay uses radiolabeled polyamines such as putrescine, spermidine or spermine, but, due to the low signal, large numbers of adherent or non-adherent cells are required. Additional care is required with spermine due to its nonspecific adsorption to cells and plastics. Cells are mixed with the test compounds and the radiolabeled polyamine to initiate the assay. The cells are incubated for 1–60 minutes, depending on cell type. The assay is terminated by removal of the medium and cooling the plates to 4° C. The cells are then washed with cold medium three times, dissolved in 0.1% sodium dodecyl sulfate and the radioactivity in solution is then determined by scintillation counting. This assay is difficult to scale up to a high throughput procedure due to the low signal from the radiolabel and the handling requirements inherent in procedures with radioactivity.

A great number of polyamine amide natural products have been recently been discovered in the venom of arthropods such as spiders and wasps. These acylpolyamine analogs have been shown to have specific and strong interactions with the neuromuscular junctions of insects (Moya, E. et al. Syntheses and neuropharmacological properties of arthropod polyaminne amide toxins. *Neuropharmacology of Polyamines* (Carter, C., ed.), 1994, Academic, San Diego, pp. 167–184). With this capability these toxins give the insect predators the ability to paralyze or kill their prey. Most of these natural products have the common molecular features of a polyamine moiety (many with structurally diverse polyamine analogs) connected through an amide with an aromatic amino acid structural analog. Simpler synthetic analogs have been sought that attempt to maximize interactions with either crustacean neuromuscular synapses or mammalian glutamate receptors (Asami, T. et al. Acylpolyamines mimic the action of Joro spider toxin (JSTX) on crustacean muscle glutamate receptors. *Biomedical Res.* 1989, 10, 185–189; Raditsch, M. et al. Polyamine spider toxins and mammalian N-methyl-D-aspartate receptors. Structural basis for channel blocking and binding of argiotoxin 636. *Eur. J. Biochem.* 1996, 240, 416–426; Tsubokawa, H. et al. Effects of a spider toxin and its analoque on glutamate-activated currents in the nippocampal CA1 Neuron after ischemia. *J. Neurophys.* 1995, 74, 218–225).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to various polyamine analogues and derivatives and their use as drugs, as agricultural or as environmentally useful agents. The invention defines sites and structures within these compounds that are key to their binding (and polyamine binding) to membrane (and soluble) proteins, particularly the PATr.

The compositions of the present invention include polyamine derivatives substituted at one or more positions. Disubstituted polyamines are preferably substituted at the two terminal nitrogens, but may be alternatively or additionally substituted at internal nitrogen and/or internal carbon atoms.

A preferred embodiment is a highly specific PAT inhibitor with pharmaceutical utility as an anti-cancer chemotherapeutic. Preferred compounds with such activity include $N^1$-dansylspermine (also termed monodansylspermine or MDS (1), $N^1$-dansylspermidine (also termed monodansylspermidine or MDSd, $N^1$-[($N^6$-dansyl)-6-aminocaproyl] spermine (termed DACS, 4), $N^1$-[($N^6$-dansyl)-6-aminocaproyl]spermidine (DACSd), $N^1$-[($N^6$-5-(4-chlorobenzamidomethyl)-thiophene-2-sulfonyl)-6-aminocaproyl] spermine 5 or $N^1$-[($N^6$-(2-dibenzofuran-sulfonyl)-6- aminocaproyl]spermine 6. The latter two compounds have surprisingly high binding and inhibitory activity compared to the corresponding compounds lacking the C6 caproyl spacer between the aryl group and the polyamine. For this reason, DACS 4 and DACSd, and compounds 5 and 6 are preferred pharmaceutical compositions. Use of alternate spacers (or linkers or couplers) and other aryl or heterocyclic "head" groups, all of which are disclosed herein, is expected to yield even more potent PAT inhibitors.

Additional preferred compounds include N1-acyl aminoacid-spermine conjugates. Natural and non-natural amino acid amides of spermine produce a series of very effective polyamine transport inhibitors. Preferred compounds in this series include L-Lys-spermine (compound 1202), L-Val-spermine (compound 1157) and L-Orn-spermine (compound 1224).

Preferred substituents are structures that increase binding affinity or otherwise enhance the irreversibility of binding of the compound to a polyamine binding molecule, such as the PATr, an enzyme or DNA. Such additional substituents include the aziridine group and various other aliphatic, aromatic, mixed aliphatic-aromatic, or heterocyclic multi-ring structures. Reactive moieties which, like aziridine, bind irreversibly to a PATr or another polyamine binding molecule, are also within the scope of this invention. Examples of reactive groups that react with nucleophiles to form covalent bonds include chloro-, bromo- and iodoacetamides, sulfonylfluorides, esters, nitrogen mustards, etc. Such reactive moieties are used for affinity labeling in a diagnostic or research context, and subserve pharmacological activity as sites within a drug that inhibit PAT or polyamine synthesis. The reactive group can be a reactive photoaffinity group such as an azido or benzophenone group. Chemical agents for photoaffinity labeling are well-known in the art (Flemming, S. A., *Tetrahedron* 51:12479–12520, 1995). Photoreactive compounds for cancer treatment are also known in the art.

Specifically, a composition which is a polyamine analogue or derivative that binds to a polyamine-binding site of a molecule and/or inhibits polyamine transport, which composition has the formula $$R_1-X-R_2$$

wherein
R$_1$ is H, or is a head group selected from the group consisting of a straight or branched C$_1$-10 aliphatic, alicyclic, single or multi-ring aromatic, single or multi-ring aryl substituted aliphatic, aliphatic-substituted single or multi-ring aromatic, a single or multi-ring heterocyclic, a single or multi-ring heterocyclic-substituted aliphatic and an aliphatic-substituted aromatic;
R$_2$ is a polyamine; and
X is CO, NHCO, NHCS, or SO$_2$ In another embodiment of the above composition, R$_2$ has the formula

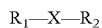

wherein
(a) n, p and q vary independently and n=p=q=1 to 12;
(b) R$_3$ is H; C$_1$-10 alkyl; C$_1$-10 alkenyl; C$_1$-10 alkynyl; alicyclic; aryl; aryl-substituted alkyl, alkenyl or alkynyl; alkyl-, alkenyl-, or alkynyl-substituted aryl; guanidino; heterocyclic; heterocyclic-substituted alkyl, alkenyl or alkynyl; and alkyl-, alkenyl-, or alkynyl-substituted heterocyclic.

The above composition may further comprise, linked between X and R$_2$, a linker L and an additional group y, such that said composition has the formula:

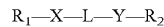

wherein,
L is a C$_{10}$ alkyl, C$_1$-10 alkenyl, C$_1$-10 alkynyl, alicyclic, or heterocyclic;
X is CO, SO$_2$, NHCO or NHCS; and
Y is CONH, SO$_2$NH, NHCO, NHCONH, NHCSNH, NHSO$_2$,SO$_2$, O, or S.

In the foregoing compositions R$_1$ can have the formula:

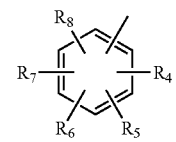

wherein
R$_4$, R$_5$, R$_6$, R$_7$ and R$_8$ are, independently, H, OH, halogen, NO$_2$, NH$_2$, NH(CH)$_n$CH$_3$, N((CH)$_n$CH$_3$)$_2$, CN, (CH)$_n$CH$_3$, O(CH)$_n$CH$_3$, S(CH$_2$)$_n$CH$_3$, NCO(CH$_2$)$_n$CH$_3$, O(CF$_2$) CF$_3$, or CO—O(CH)CH$_3$ where n=0 to 10;
Alternatively, R$_1$ has the formula:

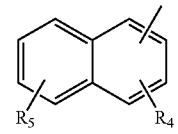

wherein
R$_4$ and R$_5$ are, independently, H, OH, halogen, NO$_2$, NH$_2$, NH(CH)CH$_3$, N((CH)$_n$CH$_3$)$_2$, CN, (CH)$_n$CH$_3$, O(CH)$_n$CH$_3$, S(CH$_2$)$_n$CH$_3$, NCO(CH$_2$)$_n$CH$_3$, O(CF$_2$)$_n$CF$_3$, or CO—O(CH)$_n$CH$_3$, where n=0 to 10;
In yet another embodiment, R$_1$ has the formula:

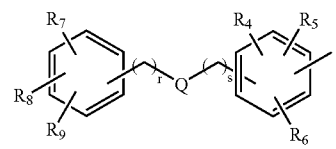

wherein
r and s vary independently and r=s=0 to 6;
R$_4$, R$_5$, R$_6$, R$_7$, R$_8$ and R$_9$ are, independently, H, OH, halogen, NO$_2$, NH$_2$, NH(CH)$_n$CH$_3$, N((CH)$_n$CH$_3$)$_2$, CN, (CH)$_n$CH$_3$, O(CH)$_n$CH$_3$, S(CH$_2$)$_n$CH$_3$, NCO(CH$_2$)$_n$CH$_3$, O(CF$_2$)$_n$CF$_3$, or CO—O(CH)$_n$CH$_3$ where n=0 to 10; and Q is CONH, SO$_2$NH, NHCO, NHCONH, NHCSNH, NHSO$_2$, SO$_2$, O, or S.
Furthermore, R$_1$ may have the formula:

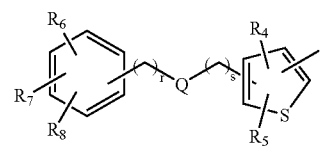

wherein r and s vary independently and are 0 to 6;

$R_4$, $R_5$, $R_6$ and $R_7$ are, independently, H, OH, $NO_2$, $NH_2$, $NH(CH)NCH_3$, $N((CH)_nCH_3)_2$, CN, $(CH)_nCH_3$, $O(CH)CH_3$, $S(CH_2) CH_3$, $NCO(CH_2)_nCH_3$, $O(CF_2)_n CF_3$, or $CO-O(CH)_nCH_3$ where n=0 to 10; and Q is CONH, $SO_2NH$, NHCO, NHCONH, NHCSNH, $NHSO_2$, $SO_2$, O, or S.

In the foregoing compositions, $R_1$ may be selected from the group consisting of naphthalene, phenanthrene, anthracene, pyrene, dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, pipiridine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 3-phenyl-5-methylisooxazole, 3-(2-chlorophenyl)-5-methylisooxazole, 2-(4-chloropheny)-6-methyl-7-chloroquinoline, 6-chloroimidazo[2,1-β]thiazole, α-methylcinnamic acid, and 2-[1,2-dihydro-2H-1,4-benzodioxepinyl]thiazole.

$R_1$ may also be a D- or L-amino acid.

Also provided is the above composition where $R_1$ has a formula selected from the group consisting of (A) $R_{12}$—$R_{13}$—$Y_1$—$R_{14}$ (B) $R_{12}Y_1R_{13}ZR_{14}$ (C)

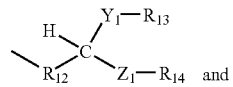

and (D)

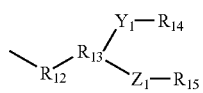

wherein $R_{12}$ and $R_{13}$, independently, are H, naphthalene, phenanthrene, anthracene, pyrene, dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, pipiridine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H 1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 3-phenyl-5-methylisooxazole, 3-(2-chlorophenyl)-5-methylisooxazole, 2-(4-chloropheny)-6-methyl-7-chloroquinoline, 6-chloroimidazo[2,1-p]thiazole, α-methylcinnamic acid, or 2-[1,2-dihydro-2H-1,4-benzodioxepinyl]thiazole;

and further, wherein a ring of $R_{12}$, $R_{13}$ or both in formulas (A), (B) and (D), is optionally substituted with one or more of OH, halogen, $NO_2$, $NH_2$, $NH(CH)_nCH_3$, $N((CH)_nCH_3)_2$, CN, $(CH)_nCH_3$, $O(CH)CH_3$, $S(CH_2)_nCH_3$, $NCO(CH_2)_nCH_3$, $O(CF_2) CF_3$, or $COO(CH)_nCH_3$, where n=0 to 10;

$R_{14}$ and $R_{15}$, and, in formula (C), $R_{13}$, independently, are $(CH_2)_n$, $(CH_2)_nCH=CH$, $(CH_2)_n(CH=CH)_mCO$, or $(CH_2)_nCo$ where n=0 to 5 and m=1 to 3;

$Y_1$ and $Z_1$, independently, are CONH, $SO_2NH$, NHCO, NHCONH, NHCSNH, $NHSO_2$, $NHSO_2$, $SO_2$—$NHSO_2$, $SO_2$, O, S, COO or when $R_1$ is of formula (A) or (B), $Y_1$ represents a bond between a C or N atom of $R_{12}$ and a C or N atom of $R_{13}$ and $Z_1$ represents a bond between a C or N atom of $R_{13}$ and a C or N atom of $R_{14}$; or when $R_1$ is of formula (C) or $Y_1$ represents a bond between the C and a C or N atom of $R_{13}$ and $Z_1$ represents a bond between the C and a C or N atom of $R_{14}$; or when $R_1$ is of formula (D) $Y_1$ represents a bond between a C or N atom of $R_{12}$ and a C or N atom of $R_{14}$ and $Z_1$ represents a bond between a C or N atom of $R_{13}$ and a C or N atom of $R_{15}$.

In the above compositions, $R_2$ preferably has the formula $$NHCH(Z_1)(CH_2)_nNH(CH_2)_pNH(CH_2)_qCH(Z_1)NHR_3$$

wherein (a) n, p and q vary independently and n=p=q=1 to 12;

(b) $R_3$ is H; $C_1$-10 alkyl; $C_1$-10 alkenyl; $C_1$-10 alkynyl; alicyclic; aryl; aryl-substituted alkyl, alkenyl or alkynyl; alkyl-, alkenyl-, or alkynyl-substituted aryl; gauanidino or heterocyclic; and (c) $Z_1$ is $CH_3$, $CH_2CH_3$ or cyclopropyl.

In another embodiment, $R_2$ has the formula:

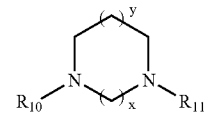

wherein x=1 to 4; y=1 to 3, $R_{10}$ and $R_{11}$ are, independently, H, $(CH_2)_nNHR_{12}$ or $(CH_2)_kNH(CH_2)_lNHR_{12}$ where n=k=l=1 to 10, and $R_{12}$ is H or C(N=H)$NH_2$ In the above compositions, $R_2$ is preferably selected from the group consisting of $N^1$-acetylspermine, $N^1$-acetylspermidine, $N^8$-acetylspermidine, $N^1$-guanidinospermine, cadaverine, aminopropylcadaverine, homospermidine, caldine (horspermidine), 7-hydroxyspermidine, thermine (norspermine), thermospermine, canavalmine, aminopropylhomospermidine, N,N'-bis(3-aminoppropyl)cadaverine, aminopentylnorspermidine, $N^4$-aminopropylnorspermidine, $N^4$-aminopropylspermidine, caldopentamine, homocaldopentamine, $N^4$-bis(aminopropyl)norspermidine, thermopentamine, $N^4$-bis(aminopropyl)spermidine, caldohexamine, homothermohexamine, homocaldohexamine, N-(3-aminopropyl)-1,3-propanediamine, N,N'-bis(3-aminopropyl)ethylendiamine, N,N'-bis(3-aminopropyl)-1,4-piperazine, N,N'-bis(3-aminopropyl)-1,3-piperazine, N,N'-bis(3-aminopropyl)-1,3-propanediamine, N,N'-bis(2-aminoethyl)-1,3-propanediamine, tris(3-aminopropyl)amine, and tris(aminoethyl) amine Preferred compositions are polyamine analogues selected from the group consisting of compounds designated herein 3, 4, 5, 6, 13, 14, 29, 40, 43, 44, 45, 57, 58, 56, 66, 67, 72, 76, 84, 88, 89, 95 and 96, most preferably, compounds 4, 5, 6, 43, 65, 66, 84, 89, 95 or 96

$R_1$ or $R_3$ may be bonded at one or more sites to a reactive moiety that is capable of forming covalent bonds with a nucleophilic site on a target molecule, such as a protein or a nucleic acid, preferably a cellular receptor or other cell surface molecule. Such composition permit essentially irreversible binding that is advantageous in both diagnostic and therapeutic uses.

Disubstituted polyamines, preferably having a reactive group at one end, may also be employed as assay or biochemical probes.

Additional substituents which may be present on the polyamine core (with or without a reporter group), are structures which increase binding affinity, or otherwise enhance the irreversibility of binding of the compound to a polyamine binding molecule, such as a PATr, an enzyme or DNA. Such additional substituents include the aziridine group and various other aliphatic, aromatic or heterocyclic multi-ring structures. A reactive moiety, which, like aziridine, can bind irreversibly to a PATr or another polyamine binding molecule is also contemplated. Examples of groups which react with nucleophiles to form covalent bonds include chloro-, bromo- and iodoacetamides, sulfonylfluorides, esters, nitrogen mustards, etc. Such reactive moieties are used for affinity labeling in a diagnostic or research context, and subserve pharmacological activity as parts of drugs that inhibit PAT or polyamine synthesis. The reactive group can also be a reactive photoaffinity group such as an azido- and benzophenone group. Chemical reagents in photoaffinity labeling are well-known (Flemming, S. A., *Tetrahedron* 51:12479–12520, 1995). Moreover, photoreactive compounds for cancer treatment are known in the art.

The polyamine analogues and derivatives of the invention may be categorized in a variety of ways. One category of polyamine analogues and derivatives are the acyl polyamines, which may be classified as $N^1$-monosubstituted and $N^1,N^{12}$-disubstituted. The monosubstituted polyamines can be further classified into categories such as amides, sulfonamides, $N^1$-monosubstituted amines and other. Among the amides, further classification into those without linkers, those with linkers, amino alkyls, and amino acid head groups is possible. The amino acid head groups can be further categorized as those that are protected, natural α-amino acids, non-natural α-amino acids, and amino acid derivatives. The full range of head groups is further detailed below.

The disubstituted polyamines can be further classified into $N^1,N^{12}$-diacyl-polyamines, $N^1,N^{12}$-acylsulfonyl-polyamines, $N^1,N^{12}$-dialkylamine-polyamines, $N^1,N^{12}$-acylalkylamine-polyamines, $N^1,N^{12}$-disulfonyl-polyamines, and $N^1,N^{12}$-sulfonylalkyl-aminepolyamines.

The theoretical classification scheme described above contains categories that are overlapping and thus not mutually exclusive. For example, many of the amino acid head group containing monosubstituted polyamines may also be considered to be a linker containing amide.

Once a polyamine analogue which inhibits polyamine transport at a desirable level has been identified, it can readily be further optimized by structural and functional comparisons with other polyamine analogues in the same or different categories to improve its utility. Examples of such improvements include, but are not limited to, increased inhibitory activity, enhanced metabolic stability, enhanced specificity, ease of handling and administration, binding affinity, non-incorporation into cellular polyamine pools, and decreases in side effects.

The present invention is also directed to a pharmaceutical composition useful for treating a disease or condition in which the inhibition of polyamine transport is desirable, comprising a composition as described above and a pharmaceutically acceptable excipient. The pharmaceutical composition may further include an inhibitor of polyamine synthesis; preferably DFMO. Other combinations include the above pharmaceutical composition and one or more additional agents known to be useful for treating said disease or condition This invention also provides a method for treating a disease or a condition in a subject associated with undesired cell proliferation and/or which is treatable by inhibition of polyamine transport, comprising administering to said subject an effective amount of a pharmaceutical composition as described above. The undesired cell proliferation may be associated with proliferation of cells of the immune system, cell of the vascular neontima, tumor cells or with undesired angiogenesis. Preferred diseases to be treated as above include cancer or post-angioplasty injury.

Thus the analogues and derivatives of the invention, alone or in combination with other agents, may be used for the treatment of cancer and other diseases of unwanted cellular proliferation, including angiogenesis and post-injury cell growth. Preferably, such treatments act by inhibiting PAT, deoxyhypusyl synthase, or cell growth or by the induction of apoptosis. As such, they may act by cytostatic and/or cytotoxic mechanisms. The analogues and derivatives of the invention, individually or in combinations with or without other agents, may also be used to treat hypertension, osteoporosis, Alzheimer's disease, ischemia, autoimmune diseases, psychosis, depression, strokes, cardiovascular disease, infection with microorganisms or parasites, plant pathogens including fungi. Cellular processes susceptible to inhibition by the analogues and derivatives of the invention, alone or in combination with other agents, include those involving nucleic acids (DNA or RNA), such as replication, transcription or translation. The analogues and derivatives of the invention may also be efficacious as anti-diarrheal, anti-peristaltic, anti-spasmodic, anti-viral, anti-psoratic and insecticidal agents.

The invention is also directed in part to rapid and efficient testing of many such analogues and derivatives for their transport into cells. By creating a database of structure-activity-relationships (SARs) of such analogues and derivatives, the invention identifies elements that are key for polyamine binding to membrane proteins such as PATr or soluble proteins. With such information, the invention permits predictions as to the transportability and activity of novel polyamine analogues and derivatives.

The polyamine analogues and derivatives of the invention may also be employed as assay or biochemical probes. A preferred assay method employs a polyamine analogue or derivative with a moiety that serves as a detectable label (a "reporter"), preferably a fluorophore, most preferably the dansyl group, or another substituent that can be detected through a variety of means, including by ELISA. A preferred assay method employs an analogue or derivative immobilized to a solid support.

The present invention is also directed to a series of polyamine analogues useful in diagnostic compositions. Methods for the synthesis of such compounds are also described.

Details concerning SARs databases, the use of polyamine analogues as assay probes, and diagnostic compositions are set forth in PCT/US98/14896.

The invention further identifies elements that are key for polyamine binding to membrane proteins such as the PATr (PATr), and to soluble proteins.

BRIEF DESCRIPTION OF THE DRAWINGS

FIG. 2 (sheets 2/1 to 2/10) is a tabular representation of a large number of chemical structures 3–98 that were tested for their effects on cell growth. R, an index of growth inhibitory activity, is the ratio of the growth of cells in the presence of the test compound to the growth in the presence of the compound plus DFMO. The $K_i$, (inhibition constant) reflects a compound's inhibition of PAT in cell culture. These biological effects provide a basis for SAR analysis.

FIG. 44a shows preferred compounds of the invention.

FIG. 44c shows preferred linked bis-amide dimers of spermine.

FIGS. 45a to 45j contains tables classifying a large number of $N^1$-monosubstituted polyamines.

FIGS. 46a to 46f contains tables classifying a large number of $N^1,N^{12}$-disubstituted polyamines.

FIG. 58 contains a table showing polyamine levels in a mammalian cell line after exposure to compound 1202.

DETAILED DESCRIPTION

Figure 1:
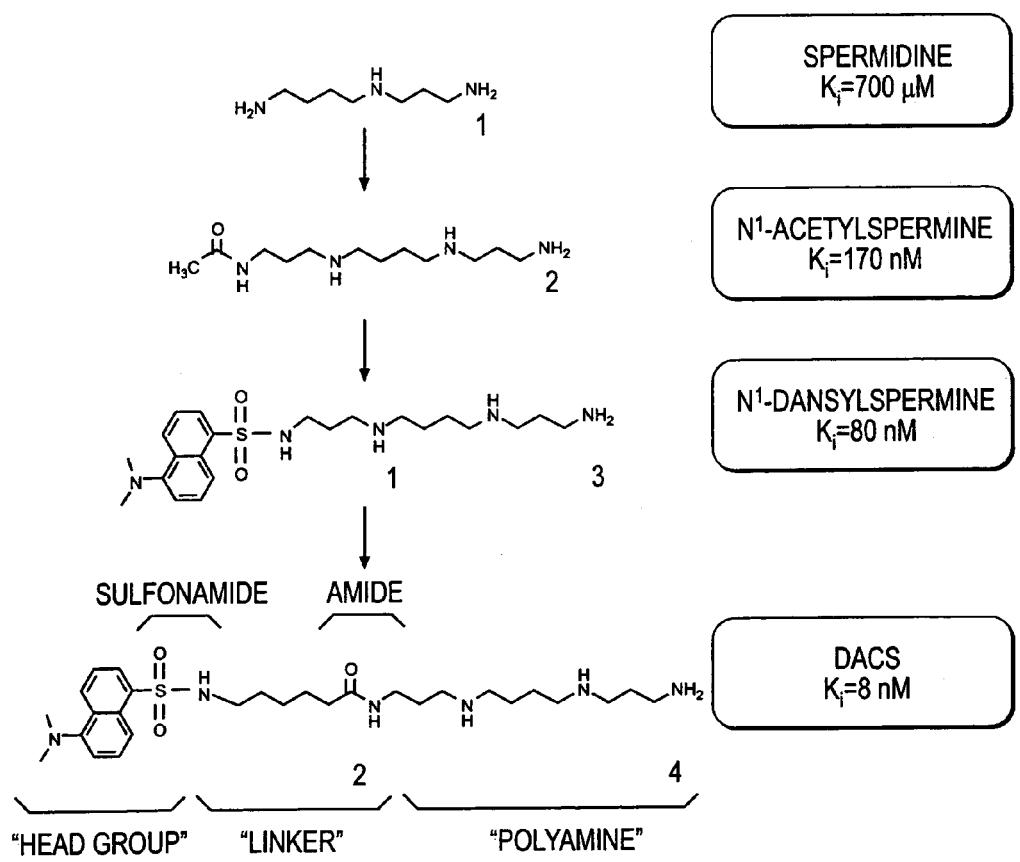
FIG. 1 shows the structure and activity relationships (SAR) between spermidine, MDS and DACS. $K_i$ values are the inhibitory constants obtained in a PAT inhibition assay.

The present inventors have designed novel compounds for therapeutic uses and have devised tests using such compounds as probes for measuring PAT and polyamine binding in an efficient, high throughput assay. Using the novel methods, they have screened for and discovered compounds with high affinity for the PATr that inhibit uptake, both competitively and non-competitively. Such compounds are useful as drugs in a number of diseases, particularly cancer. They can also be used as a component of novel drug combinations with, for example, a polyamine synthesis inhibitor such as DFMO (which inhibits ornithine decarboxylase) or with other agents. The compounds of the present invention are also useful in other diseases or conditions in which polyamines play a role as described above, and have agricultural and environmental uses.

The inventors found that various chemical groups can be attached to a polyamine to give it advantageous properties as an inhibitor of PAT or as a probe in an assay of PAT and for drug screening. Such chemical modification does not destroy the effective binding and, in fact, enhances the affinity of the derivatized polyamine for the PATr. Hence, these compounds are useful for discovery of inhibitors of polyamine uptake.

Definitions

As used herein, the term "polyamine" includes putrescine, spermine or spermidine, as well as longer linear polyamines, branched polyamines, and the like, which may have between 2 and about 10 nitrogens. Also included in this definition are polyamine derivatives or analogues comprising a basic polyamine chain with any of a number of functional groups bound to a C atom or a terminal or internal N atom. A polyamine derivative may include a terminal linker or spacer group between the polyamine core and a derivatizing function.

A "head group" is defined as a moiety bonded either directly to the polyamine or attached to a linker that is bonded to the polyamine. It is preferably an aromatic or heterocyclic group, although aliphatic groups or aroalkyl groups are included. Thus, a head group may be a fluorescent moiety, which also serves as a "reporter."

An "inhibitor" moiety or group is a chemical group derivatizing a polyamine that (1) causes the derivative to bind to the PATr with higher affinity than does a native polyamine and/or (2) by other means blocks the uptake of a polyamine (or a probe of this invention) into a cell or a subcellular PATr preparation. The inventors disclose herein compounds that efficiently inhibit PAT in MDA-MB-231 human breast carcinoma cell and other cells. A number of different types of such inhibitors have been synthesized; various of the synthetic schemes are disclosed herein.

A "reporter moiety" is a chemical moiety forming part of a probe which renders the probe detectable (either directly or, for example, through enzymatic enhancement) and hence permits the determination of the activity of the PATr to which the probe binds. A reporter is detectable either because it itself emits a detectable signal, or by virtue of its affinity for a reporter-specific partner which is detectable or becomes so by binding to, or otherwise reacting with, the reporter. In a preferred embodiment the polyamine analogue is immobilized to a solid support which enables removal of the analogue and any interacting/binding molecules from a complex mixture.

The various inhibitor compounds disclosed herein are identified by various numerical designations, including a counting scheme (using values from 1 to 166 and above) and an identifier number scheme (using four digit compound numbers alone or in combination with an "ORI" or "Ori" identifier). Irrespective of what identifying scheme is used, the identifier merely represents the actual molecular structure of the compound involved and imposes no limitation on said compound.

Overview of Structure-Activity Relationships (SARs)

The PAT inhibitors were developed by modification of the natural substrate of the transporter, spermidine. The present inventors discovered that introduction of a 3-amidopropyl group to the diaminobutyl part of spermidine produced a significantly better transport inhibitor as shown in FIG. 1. The optimal amido or sulfonamide substituent was found to be a medium sized aromatic group, leading to the invention of $N^1$-dansylspermine (MDS) as both a transport inhibitor and a transport assay reporter molecule. MDS has increased binding affinity to cells compared to spermidine and $N^1$-acetylspermine. Significantly enhanced inhibition of cell growth and PAT resulted from the introduction of a 6-carbon atom linker between the aromatic "head" group of MDS and the polyamine core. This new molecule, $N^1$-[($N^6$-dansyl)-6-aminocaproyl]spermine (or DACS) 4, is one of the most potent PAT inhibitors known. In its interaction with biological systems, DACS shows many of the desired properties set forth above. The present inventors have studied DACS and other related analogues extensively.

The SARs around DACS 4 as a lead compound have been explored extensively as shown in FIG. 2 (in particular, compounds 73–98). As discussed above, changes were made in each of several regions of DACS, and effects on transporter binding were measured. The impact of changing the aromatic "head" group was explored by synthesizing a number of different activated 4-nitrophenyl esters with different aromatic and non-aromatic N-sulfonamides at the distal amino end. Another series of "headless" analogues were synthesized to explore the importance of the hydrophobic aromatic grouping. In sum, the present inventors have designed and synthesized a large number of compounds that efficiently inhibit PAT. As described herein, all mono, di and multi-substituted polyamines with the various substituents are intended for use as drugs.

A. $N^1$-Substituted Polyamine Analogues

Figure 3:
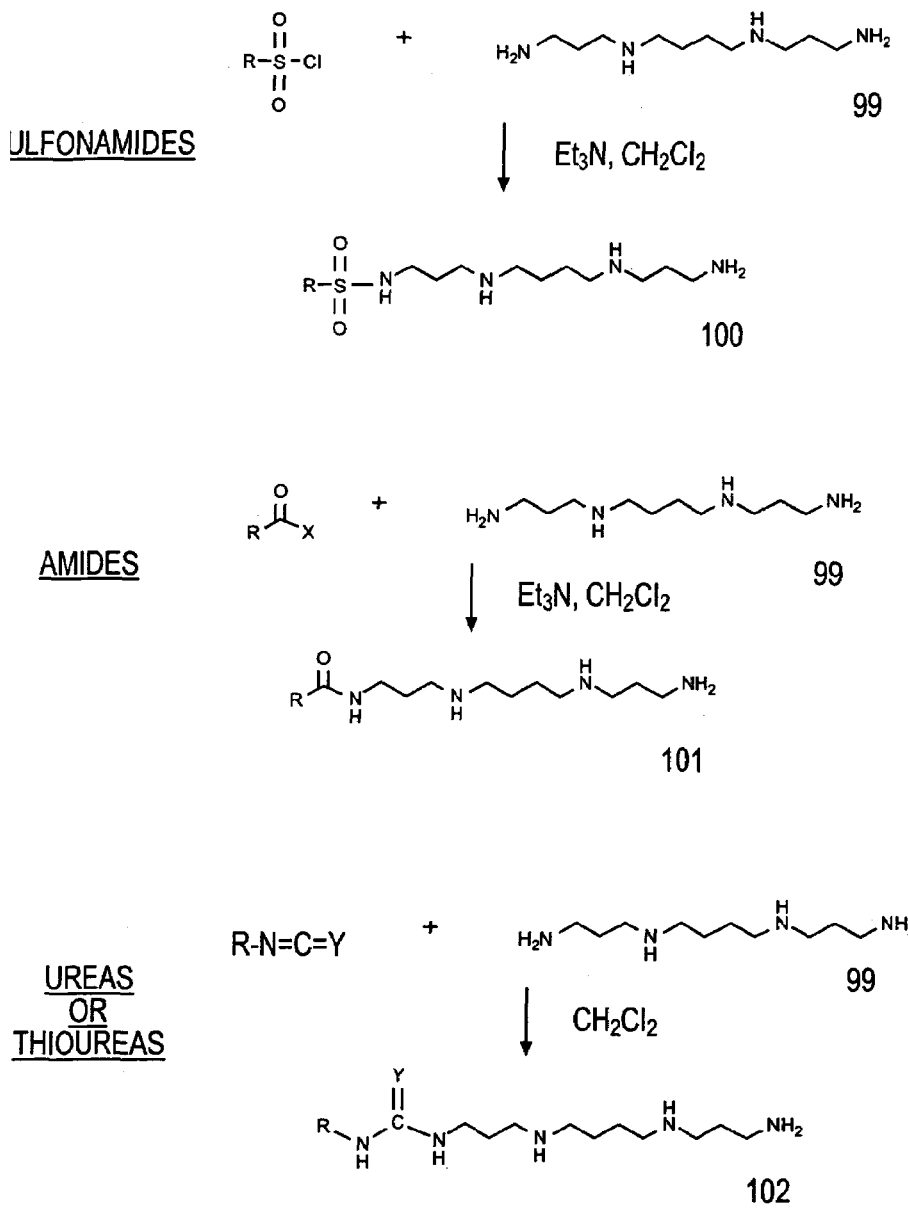
FIG. 3 shows synthetic routes to $N^1$-substituted polyamine analogues 99–102.

A series of inhibitors was made by direct reaction of a polyamine with a sulfonyl chloride, acyl, isocyanate, isothiocyanate, alkyl chloride or an N-hydroxysuccinamide-activated carboxy ester as described in FIG. 3 and in Examples I–IV. Different head groups, linkages and polyamines were combined. Many of the Figures show spermine as a nonlimiting example of the polyamine core of the molecule.

The polyamine core can be varied as defined above. The synthesis of $N^1$-(1-pyrenylsulfonyl)spermine 15 from spermine and 1-pyrenesulfonyl chloride (FIG. 5) is described in detail in Example II.

The synthesis of $N^1$-((1-carbonyl)-4-(1-pyrenyl)butane) spermine 7, from spermine and pyrenebutyric acid (FIG. 6) illustrates the use of 1-(3-dimethylaminopropyl)-3-ethylcarbodiimide hydrochloride (or EDAC) to form, in situ, the activated N-hydroxysuccinimide ester of a carboxylic acid. This one-step method produces the amide analogues of polyamines (see Example III). The synthesis of N-(1-anthracenyl)-N'-($N^1$-spermidyl)urea 9 from 1-aminoanthracene and spermine (FIG. 4) is described in more detail in Example IV. This illustrates the synthesis of ureas by activated urethanes as intermediates. Urea derivatives can also be synthesized using substituted isocyanates. For example, 1-aminoanthracene is first activated with p-nitrophenyl chloroformate to form the urethane which is reacted with spermine to yield a substituted urea 9. The synthesis of N-($N^1$-spermidyl)-2-(naphthoxy)acetamide 104 and O-(fluorenylmethyl)-N-(N1-spermidyl)urethane 105 are described in Examples V and VI, respectively.

Figure 4:
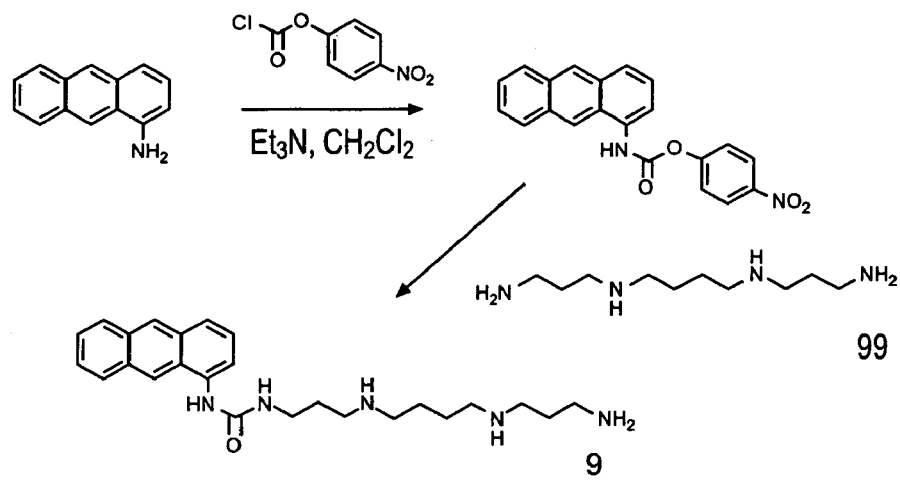
FIG. 4 is a scheme of the synthesis of N-(1-anthracenyl)-N'-(N-spermidyl)-urea 9
Figure 5:
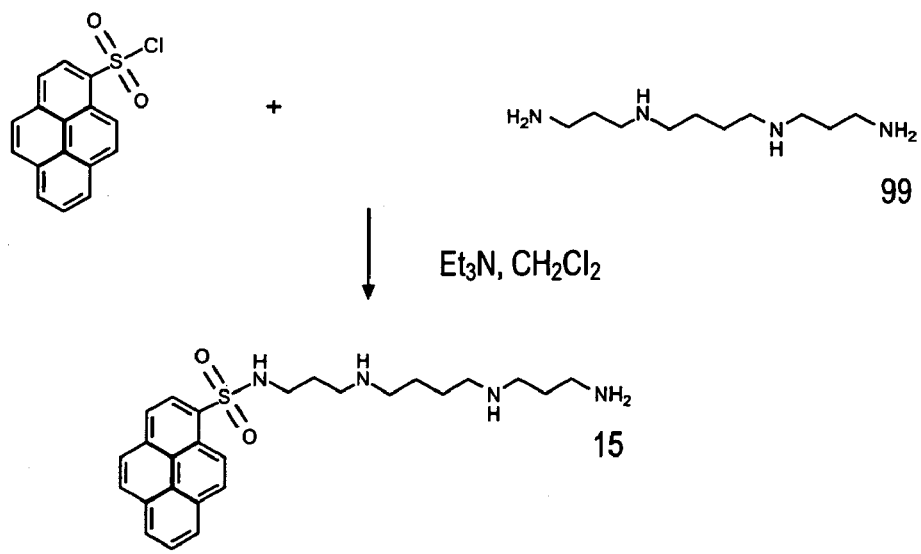
FIG. 5 is a scheme of the synthesis of $N^1$-(1-pyrenylsulfonyl)spermine 15

The best PAT inhibitors of this group have spermine as the polyamine core and include a head group such as pyrenyl (see FIG. 5; Example II (15)), 5-(4-chlorobenzamidomethyl) thiophenenyl (13) or dansyl (3) (FIG. 7; Example 1). These three compounds inhibit the PATr with $K_i$'s of 91, 58 and 80 nM, respectively. A head group can also be attached to spermine via an amide bond as illustrated by compound 14, resulting in a $K_i$ of 37 nM. Inhibitors of this type typically have $K_i$ values of approximately 100 nM and R values in the MDA growth assay of >1. However, when spermine was substituted with N-(3-aminopropyl)-1,3-propanediamine, N,N'-bis-(3-aminopropyl)ethylenediamine, N,N'-bis(3-aminopropyl)piperazine, N,N'-bis(3-aminopropyl)-1,3-propanediamine, N,N'-bis(2-aminoethyl)-1,3-propanediamine, tris(3-aminopropyl)amine or tris(2-aminoethyl)amine, the $K_i$ values in the polyamine transport assay were above 200 nM. Such less inhibitory compounds are omitted from FIG. 2 (which lists compounds 3–98). The synthesis of these types of compounds is exemplified in FIGS. 4–7 (Examples I–IV).

The Examples illustrate a key point regarding the synthetic methods. In Example I, the polyamine in $CH_2Cl_2$ solvent was treated dropwise to a solution of the acid chloride in the same solvent. This gave a statistical mixture of the unsubstituted, monosubstituted and disubstituted polyamine derivatives, which is advantageous because purification by the methods described herein resulted in pure mono- and di-substituted derivatives. Each analogue was then tested in the biological assays (PAT inhibition and cell growth inhibition). It was sometimes an advantage to produce an individual mono-substituted derivative using a mono-protected polyamine intermediate. Large-scale (>5 grams) production of the analogues was accomplished in this fashion because removal of side products was greatly facilitated.

Figure 8:
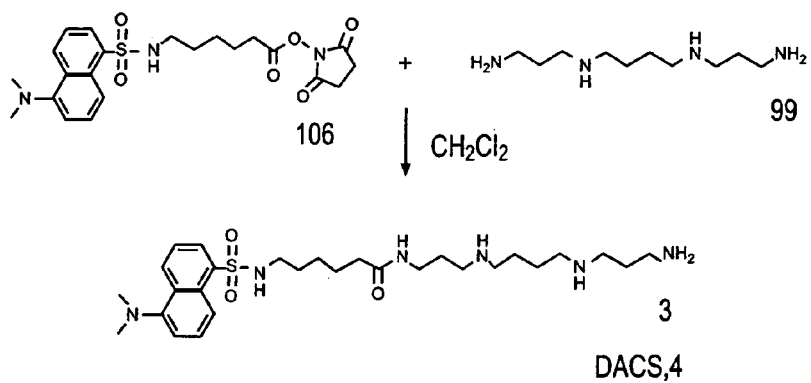
FIGS. 8 and 9 each show a different synthetic scheme for the synthesis of DACS.
Figure 9:
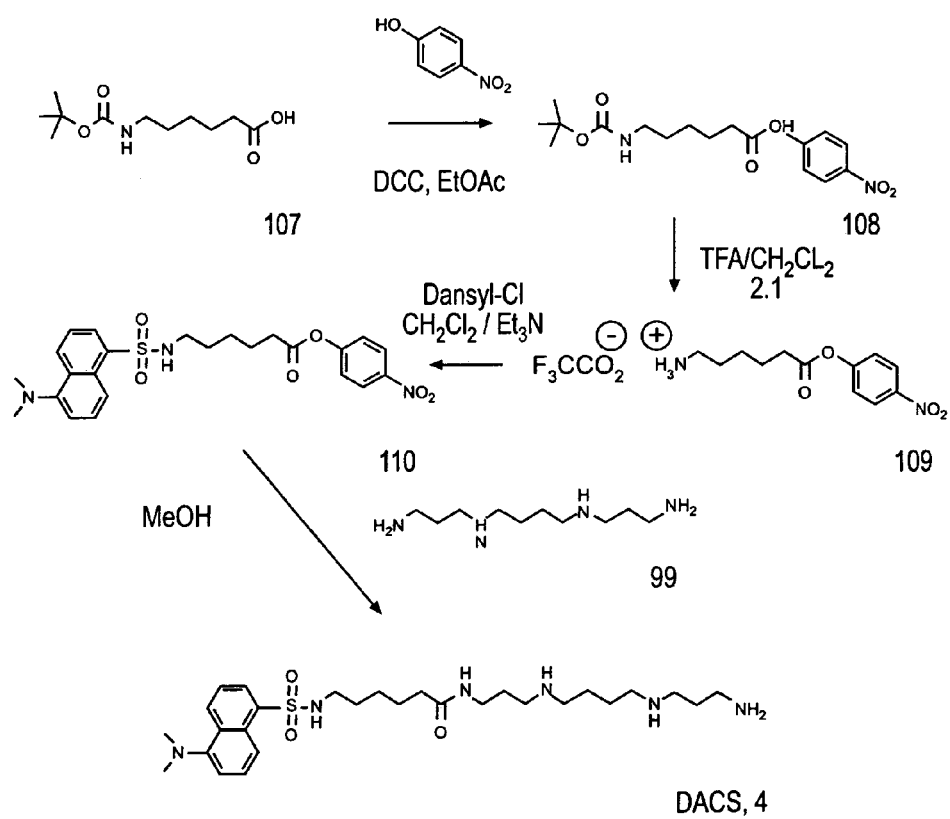

The preferred mono-protected polyamine intermediates were the $N^1$-tBoc derivatives produced according to Blagbrough et al., (*Tetrahedron Lett.* 35:20572060, 1994), using di-tert-butyldicarbonate in tetrahydrofuran. Mono protected spermine was used to synthesize naphthyl-2,6-bis(N,N'-spermidylsulfonamide) as described in Example VII B. Discovery of Lead Compound Following structural explorations around the amide, sulfonamide or urea substituent, it was determined that introduction of a six carbon, straight chain aliphatic linker between the polyamine core and the head group led to a 10-fold increase in binding to the PATr (see FIG. 1). Given the high affinity this compound, DACS 4, to its biological target, it was selected as a lead compound for further modification. Two methods for the synthesis of DACS 4 are presented. The first method uses two commercially available starting materials, appropriate for synthesizing small amounts of DACS 4. The synthesis DACS 4 from spermine and 6-((5-dimethylaminonaphthalene-1-sulfonyl)amino) hexanoic acid succinimidyl ester is shown in FIG. 8, (showing compounds 4, 99, 106) and described in more detail in Example VII. The second, multistep method (FIG. 9; showing compounds 4, 99, 107–110), uses structurally flexible synthetic procedures for producing the modified analogues. The multistep production of DACS 4 in the second method (Examples IX–XII) illustrates the procedure used to synthesize many of the linker analogues in described herein. This method is based in part on R. Goodnow et al., (*Tetrahedron Lett* 46:3267, 1990). The p-nitrophenyl ester of a N-tBoc blocked amino acid is synthesized using DCC in EtOAc and then deblocked by the trifluoroacetic/$CH_2Cl_2$ method. The p-nitrophenylalkylaminoester is then derivatized with an acyl chloride, sulfonyl chloride, or the equivalent, to introduce the head group. The N-substituted amino acid p-nitrophenyl ester reacts readily in methanol with excess polyamine to yield the desired product. The desired monosubstituted product is purified from the excess polyamine and a minor di-substituted side-product by low-pressure C18 reversed phase chromatography (RPLC) and $CH_3OH$/0.5N HCl elution. Alternatively, the product can be separated on a weak cation exchanger such as BioRad®70, with a $NH_4OH$ gradient. A more detailed description is provided in Examples IX–XII. The two methods shown in FIGS. 8 and 9 compare the two purification methods used throughout this work (Examples VIII, XII)

Using the second procedure, different "head" groups can be easily coupled to the p-nitrophenyl activated ester (different "head" groups outlined below). Following purification of this active ester, it can be readily coupled to the various polyamine derivatives. This method also gives great flexibility in the choice of linkers. Any compound possessing both an acid and an amino functionality can be incorporated into the molecule. See Examples VIII–XII.

Structural Modifications of DACS

The Polyamine Core

1. General Structural Issues

The structure below shows the general modifications that can be made to the polyamine core of the compound.

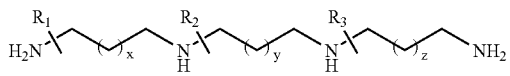

where x, y and z vary independently and may be 0 to 12, and $R_1$, $R_2$, and $R_3$ may be H, alkyl or aryl group. Stereoisomers can be separated A fruitful general approach to realize selectivity of binding to a target (e.g., protein) of interest has been to synthesize conformationally or stereochemically defined analogues of a binding molecule. By significantly reducing the number of possible rotomers or conformations a molecule can adopt, one can attain increased binding to the desired site. Since the molecule no longer has to search the entire "conformational space," its energy of interaction with the target increases many times.

Others have tried to solve the selectivity problem with polyamine analogues by synthesizing conformationally restricted analogues. Ganem replaced the butyl portion of spermine with 2-butene and 2-butyne diamino derivatives (Ganem, B., *J. Org. Chem* 1987, 52, 5044–5046). Rajeev, K. G. et al., *J. Org. Chem.* 1997, 62, 5169–5173, incorporated a stereochemically defined, conformationally restrained pyrrolidine ring into the spermine backbone (FIG. 10; 115, x=1) Brand, G. et al., Tetrahedron Lett 1994, 35, 8609–8612, synthesized cyclopolyamine analogues of spermidine and spermine. See, for example FIG. 10 (113, x=3, 4, and 5). The present inventors extended this work by producing the other analogues shown in FIG. 10. These analogues are synthesized using variations of known methods. The analogues where x=1 are produced by reacting spermine or N,N'-bis (3-aminopropyl)-1,3-propanediamine with formaldehyde as described by Ganem, B., *Acc. Chem. Res.,* 1982, 15, 290). The primary amines are protected as N-tBoc derivatives for the analogues 111 and 113. Acid deprotection then gives the desired products. The derivative 112, where x=1, was also synthesized Ganem.

Analogues 111 and 113 (FIG. 10), where x=2 to 4, were produced by reductive alkylation. $N^1$, $N^{14}$-Bis(tBoc)spermine was reacted with the dialdehyde, $OHC(CH_2)_x 2CHO$ and $NaBH_4$ in EtOH. Compounds 112 and 114 were made by the same procedure on a suitable $N^1,N^4$-bisprotected spermine derivative.

Figure 10:
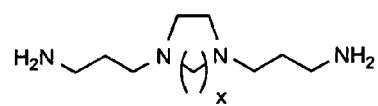
FIG. 10 shows four classes (111–114) of conformationally restricted polyamine analogues, and at the bottom, a stereochemically defined, internally cyclic polyamine analogues (116).
Figure 10:
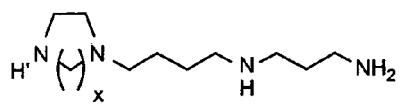
Figure 10:
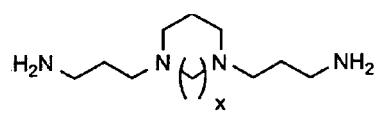
Figure 10:
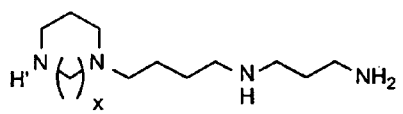
Figure 10:
Figure 10:
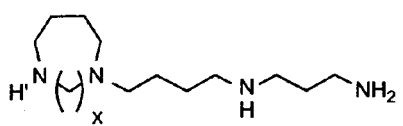
Figure 10:
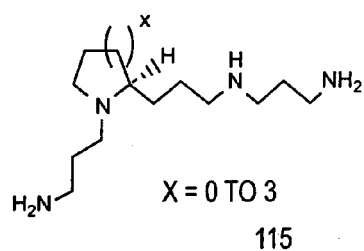

Stereochemically defined, internally cyclic structures (FIG. 10, 115 are synthesized using an intermediate aldehyde produced from alcohol 130 shown in FIG. 4. This protected alcohol 130 can be oxidized to the aldehyde using Swern conditions. Aldehyde extension by the Wittig reaction with formylmethylene triphenylphosphorane, followed by reduction (overreduced alcohol can be reoxidized to the aldehyde using pyridinium chlorochromate) and reductive amination/cyclization completed the sequence to make the analogues where x=2. By Wittig reaction with 3-bromopropyl triphenylphosphonium bromide, deprotection and intramolecular alkylative cyclization, the analogue where x=3 can be produced. Either stereoisomer can be produced by starting with L- or D-ornithine. Polyamines containing a guanidinium group are synthesized according to Iwanowicz, E. J. et al., *Synthetic Comm.* 23 1443–1445, 1993.

2. Natural Polyamines

The natural polyamines, including putrescine, spermidine and spermine, are incorporated into the compositions of this invention by coupling them to the various "head" and "linker" groups. Other naturally occurring polyamines that can be employed similarly include: $N^1$-acetylspermine, $N^1$-acetylspermidine, $N^8$-acetylspermidine, $N^1$-guanidinospermine, cadaverine, aminopropylcadaverine, homospermidine, caldine (norspermidine), 7-hydroxyspermidine, thermine (norspermine), thermospermine, canavalmine, aminopropylhomospermidine, N, N'-bis(3-aminopropyl)cadaverine, aminopentylnorspermidine, $N^4$-aminopropylnorspermidine, $N^4$-aminopropylspermidine, caldopentamine, homocaldopentamine, $N^4$-bis(aminopropyl)norspermidine, thermopentamine, $N^4$-bis(aminopropyl)spermidine, caldohexamine, homothermohexamine and homocaldohexamine.

3. $N^1$-Alkylated polyamines

The metabolic stability in vivo of monosubstituted polyamine analogues is increased by modifying these compounds to resist enzymatic degradation. For example, substitution of the terminal primary amine group with an alkyl group would achieve this by preventing oxidative metabolism. This invention also includes compounds with alkylated secondary amino groups. N-alkylation of the amide nitrogens slows down proteolytic degradation.

Figure 11A:
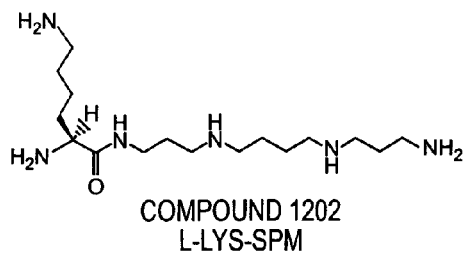
FIG. 11a shows compound 1202 L-Lys-spermine and variations of that compound.
Figure 11A:
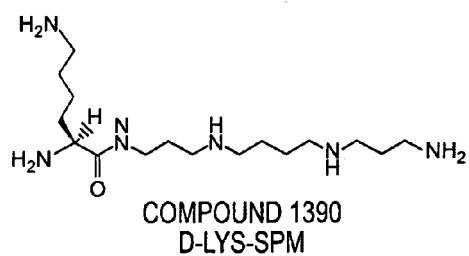
Figure 11A:
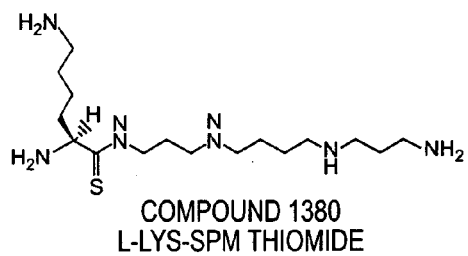
Figure 11A:
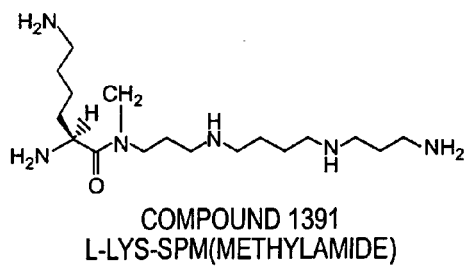
Figure 11A:
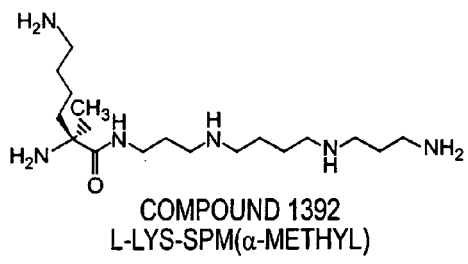
Figure 11A:
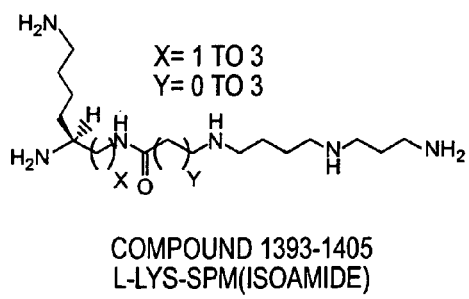

An additional method to prevent metabolic degradation of amide bonds is to produce the thioamide derivative. FIG. 11a shows these changes implemented into compound 1202 L-Lys-spermine conjugates. Combinations of these changes are also encompassed as part of the present invention.

The foregoing changes can be achieved by a number of synthetic routes. Substitution of carbon atoms a to secondary nitrogens and acylation of nitrogens can also slow degradation by polyamine oxidase. Such chemical modifications may minimize potential pharmacological side effects of these compounds.

Figure 11B:
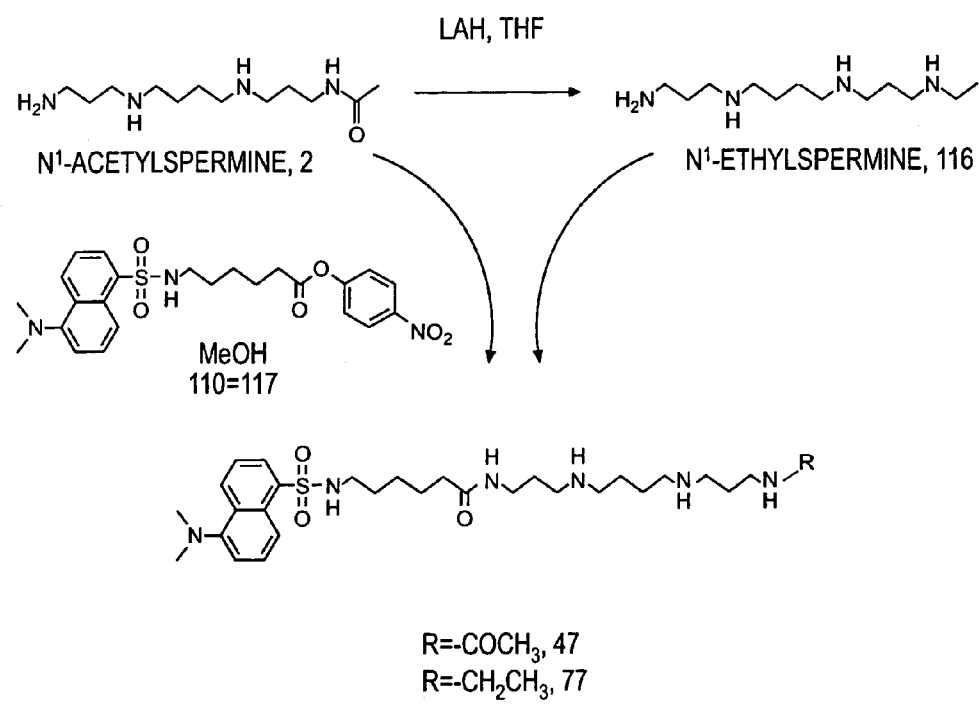
FIG. 11b is a synthetic scheme wherein free primary amino groups are blocked by N-acylation (44) and N-alkylation (77), thereby reducing potential metabolic degradation of the derivatized PAT inhibitors.

To reduce potential metabolic degradation of derivatized PAT transport inhibitors, the terminal free primary amino group can be blocked by N-alkylation (Bergeron, R. J. et al., *J. Med. Chem.* 37:3464–347, 1994) as illustrated in FIG. 11b (compounds 2, 47, 77, 116–117). Lithium aluminum hydride (LAH) reduction of $N^1$-acetylspermine 2 yields the desired $N^1$-ethylspermine 116. Reaction of $N^1$-ethylspermine 116 or $N^1$-acetylspermine 2 with a N-substituted p-nitrophenylester of an amino acid in methanol gives the desired compound modified with either an ethyl or an acetyl group at the primary $N^1$.

Figure 12:
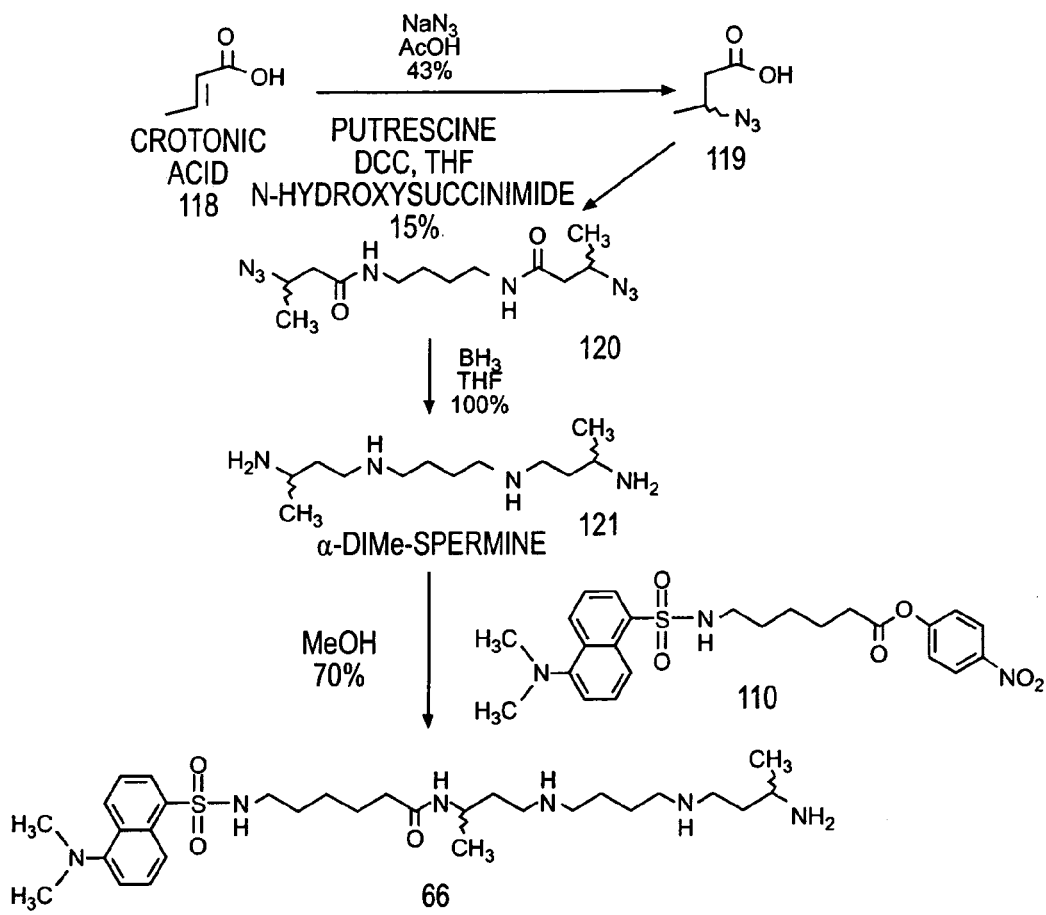
FIG. 12 is a synthetic scheme for α-dimethylpolyamine analogues 121.
Figure 13:
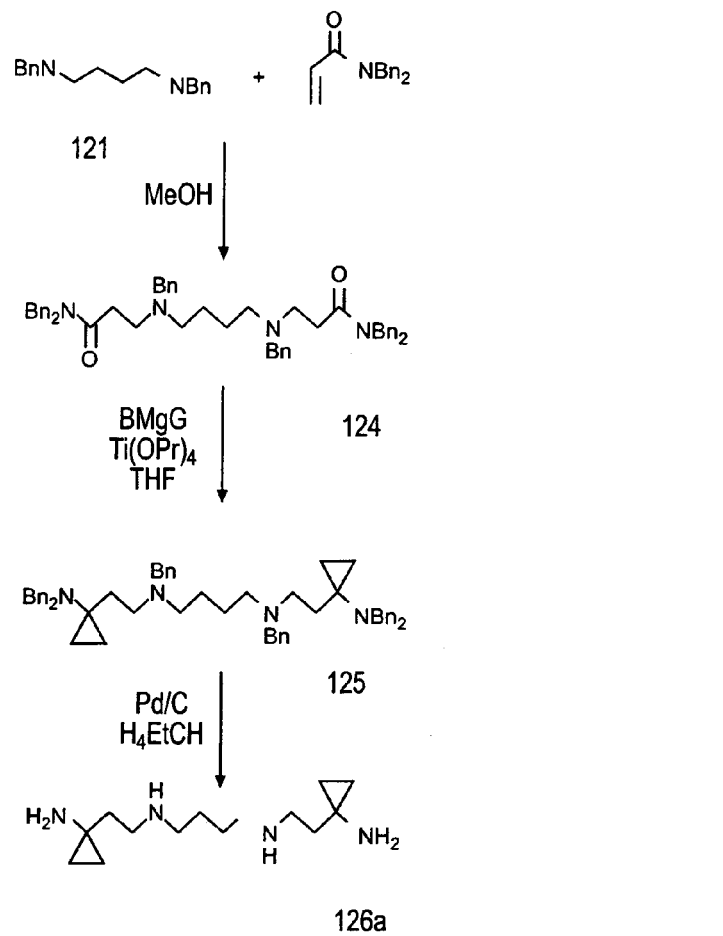
FIG. 13 is a synthetic scheme for internally substituted polyamine analogues containing cyclopropyl groups (122–126)
Figure 13:
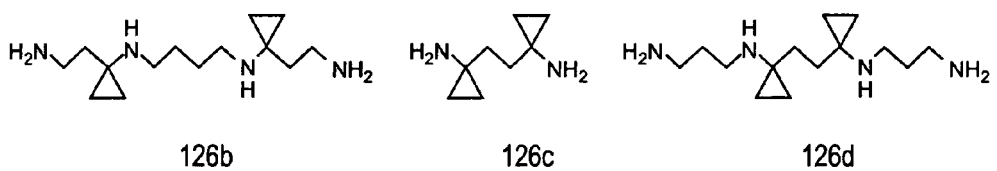

Alternatively, methyl groups can be introduced a to the terminal amino groups (121) of spermine (Lakanen, J. R. et al., *J. Med. Chem.* 35:724–734, 1992). The 1,12-dimethylspermine analogue 121 was very resistant to normal metabolic degradation. This compound is easily coupled to a linker and head group as shown in FIG. 12 (compounds 66, 18, 121). Ganem, B., *J. Org. Chem.* 1986, 51, 4856–4861, synthesized bis α-gem-dimethylpolyamine analogues. The present inventors have extended upon these two reports and synthesized the bis-cyclopropylamine analogues by the route described below. See FIG. 13. Reaction of the perbenzylated diamide with EtMgBr and Ti(O'Pr)$_4$ according to Chaplinski, V., *Angew. Chem. Int. Ed. Engl.* 1996, 35, 413–414 or Lee, J. *J. Org. Chem.* 1997, 62, 1584–1585 produced the fully protected bis-cyclopropylamino analogue of spermine. Catalytic hydrogenation yields a fully deprotected polyamine. Other internally, cyclopropyl-substituted polyamine analogues can be produced in an analogous manner to that shown in FIG. 13. Other analogues produced are shown at the bottom of FIG. 13. These cyclopropyl polyamine analogues are activated by cellular enzymes to become alkylating agents.

Polyamine analogues of 4 with acetyl (47), N-ethyl (35) and α-dimethyl (66) substitution have been synthesized and shown to have $K_i$'s (for the MDA-MB-231 cell PATr) of 2100, 41, 18 nM, respectively.

Detectably labeled polyamine derivatives can be synthesized using radiolabeled $^{14}$C-spermine or other radiolabeled polyamine as starting material.

4. Internally Substituted Polyamine Analogues

Figure 14:
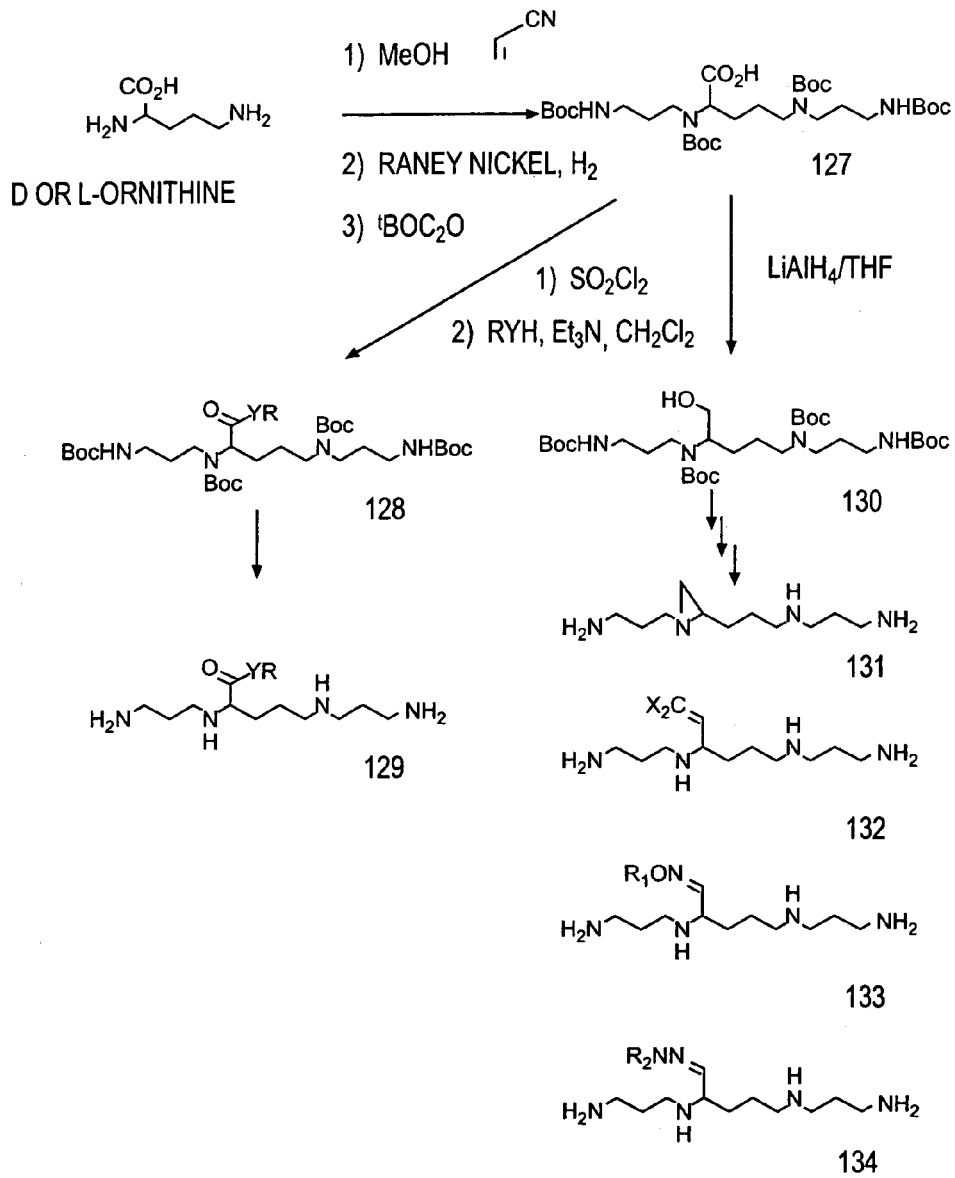
FIG. 14 is a synthetic scheme for internally substituted polyamine analogues containing a C—C branch (127–134)

Various polyamine analogues alkylated at internal carbons can also be synthesized. 5-carboxyspermine, tetra ,Boc-5-carboxyspermine and its acid chloride are synthesized according Huber, H. et al, *J. Biol. Chem.* 271: 27556–27563, 1994. The resulting acid chloride can then be reacted with various nucleophilic reagents to produce carboxy-substituted polyamine analogues following removal of the tBoc group. These analogues can then be coupled to the reagents that donate the linker and/or head group. Alternatively, the carboxy intermediate can be reduced to an intermediate that is used to synthesize numerous analogues. Such analogues are of interest in the present invention as alkylating agents (e.g, internal aziridine spermine derivatives) or as enzyme-activated irreversible inhibitors of enzymes involved in polyamine biosynthesis, utilization and degradation (e.g., spermine synthase, deoxyhypusine synthase, polyamine oxidase) as shown in FIG. 14 (compounds 130–134). Any enzyme that acts on the substituted carbon atom will generate a highly reactive intermediate that can alkylate the enzyme's active site residues.

5. Commercially Available Polyamine Analogues

Many polyamine derivatives are available commercially, and these can easily be derivatized further to make the polyamine analogues of the present invention.

Preferred Polyamine Analogues and Derivatives

Figure 46A:
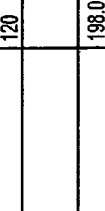
Figure 46F:

Preferred compounds include those presented in FIGS. 44–46 as well as derivatives thereof with pharmaceutical utility as an anti-cancer, anti-viral, antimicrobial, or anti-fungal chemotherapeutic. Particularly preferred compounds include those numbered 1090, 1157, 1202, 1224, 1242, and 1340, as well as derivatives thereof. Compound 1340 has structural features found in both 1202 and 1090, and has a potent IC$_{50}$ value falling in between that of these two compounds. Compound 1340 is also more soluble than 1090 and so is preferred for pharmaceutical applications. Compound 1242, and derivatives thereof, are of particular interest as an anti-fungal and/or anti-bacterial agent. Compounds 1157 and 1202, and derivatives thereof, are of particular interest as anti-cancer agents. The structures of compounds 1202, 1157 and 1224 are presented in FIG. 44a.

Figure 44B:
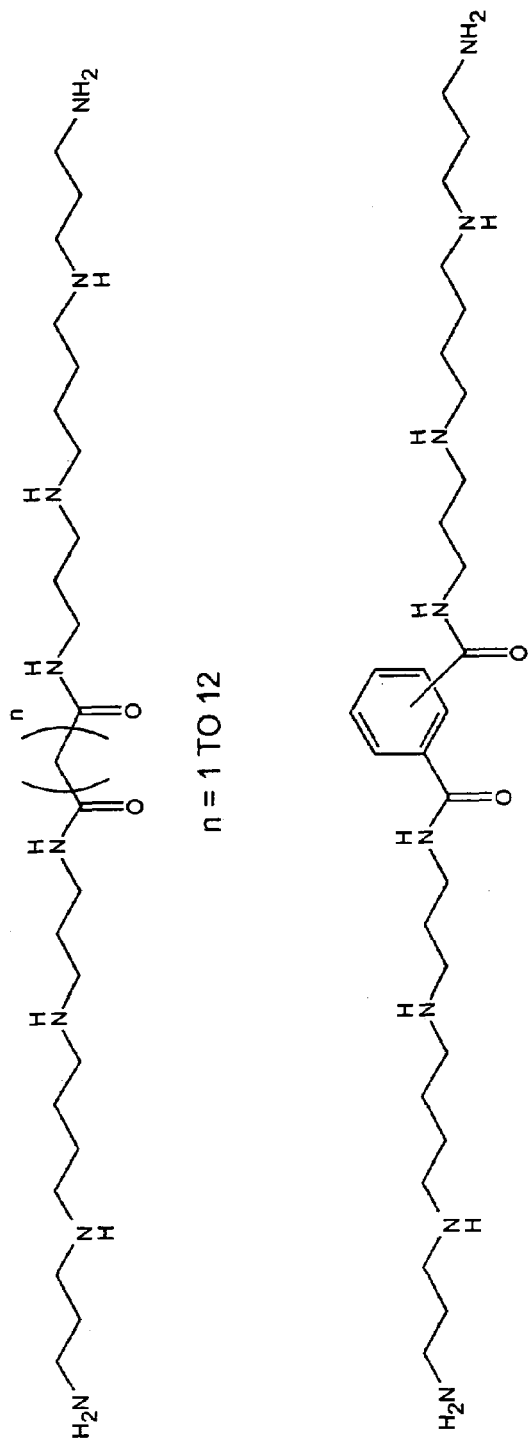
FIG. 44b shows the general structure of bis-amide dimers of spermine linked by an aliphatic or aromatic di-acid chain.
Figure 45C:
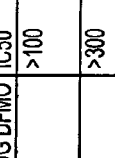
Figure 45C:
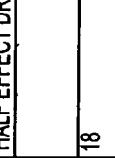
Figure 45C:
Figure 45C:
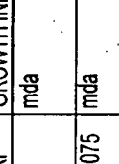
Figure 45C:
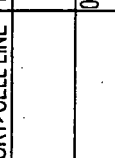
Figure 45C:
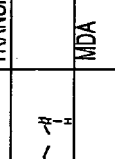
Figure 45C:
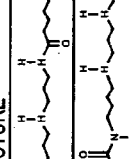
Figure 45C:
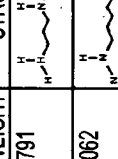
Figure 45C:
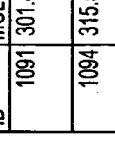

Additional preferred compounds that have the desired activity include bis-amid dimers of spermine linked by an aliphatic or aromatic di-acid chain. This series is defined in the general structure set forth in FIG. 44b. Several preferred specific compounds are shown in FIG. 44c.

The further derivatization or optimization of compounds having a desirable activity may be achieved by structural and functional comparisons with other polyamine analogues and derivatives of the invention to incorporate particular structural elements of other analogues into the compound being optimized. The structural elements will be selected based on the expectation of improving functionalities such as, but not limited to, inhibitory activity, metabolic stability, specificity, handling and administration, binding affinity, non-incorporation into cellular polyamine pools, and decreases in side effects.

The resultant compounds modified by the introduction of such structural elements may be of any structure, including those within the limits of the polyamine analogues and derivative structures defined herein. Stated differently, the resultant compounds may have one or more additional atoms or functional groups and/or removal of one or more atoms or functional groups after optimization, resulting in a compound either within or beyond the limits of the polyamine analogues and derivative structures defined herein.

Multiple iterations of optimizing compounds with preferred activity may be conducted to further improve the polyamine analogue.

$R_1$ or $R_3$ as presented above may be bonded at one or more sites to a reactive moiety that is capable of forming covalent bonds with a nucleophilic site on a target molecule, such as a protein or a nucleic acid, preferably a cellular receptor or other cell surface molecule. Such compounds permit essentially irreversible binding that is advantageous in both diagnostic and therapeutic uses.

The invention also describes the design, synthesis and biological evaluation of a series of amino acid/spermine conjugates that act as potent polyamine transport inhibitors in MDA breast cancer cells. An additional series of spermine amides were evaluated to extend the structure-activity relationship around this polyamine transport target. These compounds were evaluated based on their: 1) ability to inhibit the cellular uptake of radiolabeled spermidine; 2) their ability to increase the growth inhibitory effects of DFMO on MDA cells in culture in the presence of spermidine; 3) their ability to reduce the intracellular levels of polyamines after the combination treatment with DFMO and 4) their ability to rescue from the growth inhibitory effects of DFMO in the absence of polyamines.

The design of some polyamine analogues and derivatives of the invention was driven by several requirements of any compound that would act in concert with an ODC inhibitor in a combination therapy to deplete cellular polyamines through both the biosynthetic and transport pathways. Such compounds need to be good inhibitors extracellular uptake of polyamines (putrescine, spermidine, and spermine) while not being themselves substrates for the transporter or for maintenance of cellular polyamine levels. If such were substrates of the transporter and could function as the natural polyamines (or be metabolized to polyamines), the compounds would defeat their purpose of depleting cellular polyamine levels.

The invention also relates to the discovery that several polyamine amide spider toxins (1022 and 1085 in FIG. 44) inhibited the transport of $^3$H-spermidine in MDA cells. This led to the synthesis of a series of amino acid spermine amide conjugates with at least three cationic centers in their polyamine portion and thus satisfy Bergeron's criteria of recognition at the polyamine transporter (Porter, C. W. et al. *J. Cancer Res* 1984, 44, 126–128). The invention also proposes a hypothesis that the presence of the amide carbonyl's oxygen in these amides would displace the H$_2$O molecule shown to be present in the spermidine binding site in the PotD crystal structure, permitting these polyamine analogs to be considered multisubstrate analogs of the polyamine transporter.

The selective primary mono-substitution of polyamines is known (Krapcho, A. P. et al. Mono-protected diamines. N-tert-butoxylcarbonyl-α,ω-alkanediamines from α,ω-alkanediamines. *Syn. Comm* 1990, 20, 2559–2564; Blagbrough, I. S. et al. Practical Synthesis of unsymmetrical polyamine amides. *Tetrahedron Lett.* 1998, 39, 439–442). Typically, an excess of polyamine is treated over time with the acylating reagent. The higher nucleophilicity of the secondary amines may mask the greater steric congestion of these amines, thus giving a higher yield of the mono-substituted primary amide products. The variously protected (α-N-$^t$Boc or α-N-Cbz) activated amino esters were coupled directly to spermine (1.5 equivalents) to yield a mixture of mono- and di-substituted products together with unreacted spermine. These crude mixtures were effectively separated using chromatography over a cation-exchange resin (such as BioRex 70, NH$_4^+$ form) using a linear gradient of base (such as 0 to 2 N NH$_4$OH in H$_2$O). Some derivatives may require the inclusion of an organic solvent, such as MeOH, in the eluting buffer to ensure complete solution during chromatography. After this purification, the protecting groups may be removed under standard conditions and the desired conjugates were obtained as their hydrochloride salts. This synthesis method may be complemented by the use of commercially available polyamine analogues.

In addition to the use of amino acid groups, the polyamine analogues and derivatives of the invention may comprise a head group linked to a polyamine where coupler such as —C(=O)NH—, —S(=O)$_2$NH—, —NHC(=O)—, —HNS(=O)$_2$—, —HNC(=O)NH—, —HNC(=S)NH—, O—C(=O)NH—, —O—, —S—, —CH$_2$— or —NH— is used to combine the "head" group and the linker moiety.

Head Groups
1. General Description

The general construction of the lead compounds shown below indicates the connections between the head group, linker and polyamine:

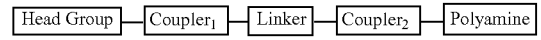

A number of coupling chemistries can be used to combine the "head" group and the linker moiety. Types of "head" groups are disclosed below as are additional groups that can be substituted onto these head groups.

The coupling between the polyamine and linker will be described below before description of the linkers. What follows is the definition of the head groups.

The structural diversity of preferred head groups is very large, and most organic groups that can be covalently attached to an amine are potential candidates. The following table provides guidance regarding the intended head groups but is by no means is intended to be limiting. Additional examples of head groups suitable for use in the polyamine analogues of the invention include those in column "R2" of Table 1 in Dhainaut et al. (1996) "New purines and purine analogs as modulators of multidrug resistance." J. Med. Chem. 39:4099–4108, which is incorporated herein in its entirety as if fully set forth. Mono and multi-substitutions on the ring structures of the head groups are also intended.

| LIST OF HEAD GROUP SUBSTITUENTS |
|---|
| halogen |
| methyl |
| ethyl |
| propyl |
| isopropyl |
| butyl |
| isobutyl |
| tert-butyl |
| pentyl |
| 2-pentyl |
| 3-pentyl |
| neopentyl |
| cyclopentyl |
| cyclopropyl |
| cyclobutyl |
| cyclohexyl |
| cycloheptyl |
| cyclooctyl |
| cyclononyl |
| cyclodecyl |
| hexyl |
| 2-hexyl |
| 3-hexyl |
| allyl |
| vinyl |
| acetylenic |
| propargylic |
| homopropargylic |
| hydroxyl |
| methoxyl |
| ethoxyl |
| propoxyl |
| thio |
| methylthio |
| ethythio |
| propylthio |
| butylthio |
| isopropylthio |
| nitro |
| amino |
| acetamide |
| formamide |
| carboxylic |
| methyl ester |
| ethyl ester |
| propyl ester |
| isopropyl ester |
| cyano |
| isocyanato |
| trifluoromethyl |
| trichloromethyl |
| tribromomethyl |
| azido |
| Acetoxy |
| Carboxamide |
| N-methylcarboxamide |
| N,N-dimethylcarboxamide |
| N-ethylcarboxamide |
| N,N-diethylcarboxamide |

2. Aromatic Groups

Aromatic groups include phenyl naphthyl, 1-, 2-, or 3-biphenyl, indenyl, acenaphthylenyl, anthracenyl, phenanthrenyl, phenalenyl, triphenylenyl pyrenyl, diphenylmethylenyl, etc.

3. Heterocyclic Groups

Heterocyclic groups include pyrrolidinyl, piperidinyl, piperazinyl, morpholinyl, biphenyl, furanyl, pyrrolyl, 1,2-diazolyl, imidazolyl, 1H,1,2,3-triazolyl, 1H-1,2,3,4-tetrazolyl, thiazolyl, oxazolyl, 1,3,4-thiadiazolyl, pyridinyl, pyrimidyl, 1,2-diazinyl, 1,4-diazinyl, 1,3,5-trizinyl, dibenzofuranyl, acridinyl, 2,1,3-benzothiadiazole, isoquinolinyl, quinolinyl, benzufuranyl, isobenzofuranyl, 1,3-benzodiazinyl, phenazinyl, phenoxazinyl, phenothiazinyl, pyran, chromenyl, xanthenyl, indolizinyl, isoindolyl, indolyl, purinyl, phthalazinyl, naphthyridinyl, quinoxalinyl, quinazolinyl, cinnolinyl, ptericinyl, carbazolyl, β-carbolinyl, phenanthridinyl, acridinyl, perimidinyl, phenanthrolinyl, isothiazoly, furazanyl, indolinyl, isoindolinyl, quinuclidinyl, and biotinyl.

4. Aliphatic Groups

This class includes straight-chain, branched and cyclic hydrocarbons attached to the linker. The group includes $C_2$-10 alkanes; $C_3$-10 alkenes containing 1 to 3 unsaturations; $C_3$-10 alkynes containing 1 to 3 unsaturations; branched $C_3$-10 alkanes, alkenes and alkynes; polycyclic aliphatic hydrocarbons and steroid-like ring systems that include $C_3$-8 cycloalkyl, adamantyl, camphoryl, cholesteryl, etc.

5. Miscellaneous—

DNA intercalators:

Coupling an intercalator to the polyamine will yield an agent with much higher affinity for nucleic acid targets. Examples of intercalating agents amenable to this use are acridine, 9-aminoacridine, proflavine, actinomycin D, daunorubicin, doxorubicin, nogalamycin, menogaril, ellipticine, BD-40, amsacrine, acodazole, 2-pheylquinoline carboxamide, crisnatol, nitracrine, pyrazoloacridine, mitonoafide, ametantrone, mitoxantrone, oxanthrazole, bisantrene, echinomycin. For a review of DNA intercalating agents see Baguley, B. C., *Anti-Cancer Drug Design* 1991, 6, 1–35.

b. Biochemical conjugates

Drug selectivity is achieved by targeting specific cells or enzymes/receptors on cells. The following biochemicals are candidates for coupling to polyamines for producing a selective pharmaceutical agent: steroids, prostaglandins, phospholipids; enzyme cofactors including nucleotide containing molecules such as NADH, AcetylCoA, AdoMet, flavin, tryptophantryptophyl quinone (TTQ), etc.

An additional series of head groups comprises polyamines conjugated to polyethylene glycol (PEG) or O-methylated PEG (abbreviated MeOPEG) polymers of various sizes.

6. Multiple Ring Head Groups

Figure 15:
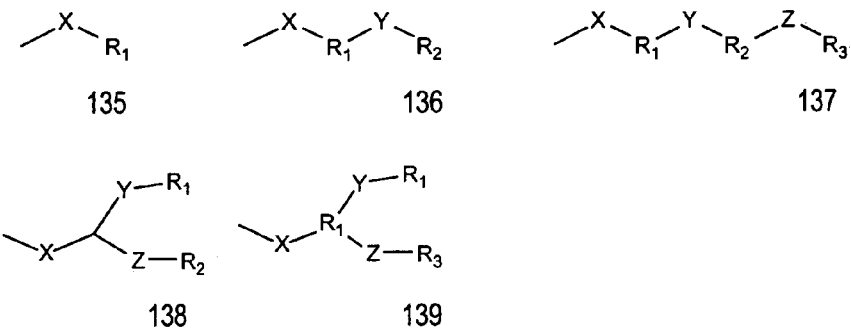
FIG. 15 shows examples of spacers or linkers for use with multi-ring head group (135–139).

Head groups can vary from simple alkyl substitutions to multi-ring and multisingle-ring substitutions. Some of the structural variations are schematically represented in FIG. 15.

Figure 16:
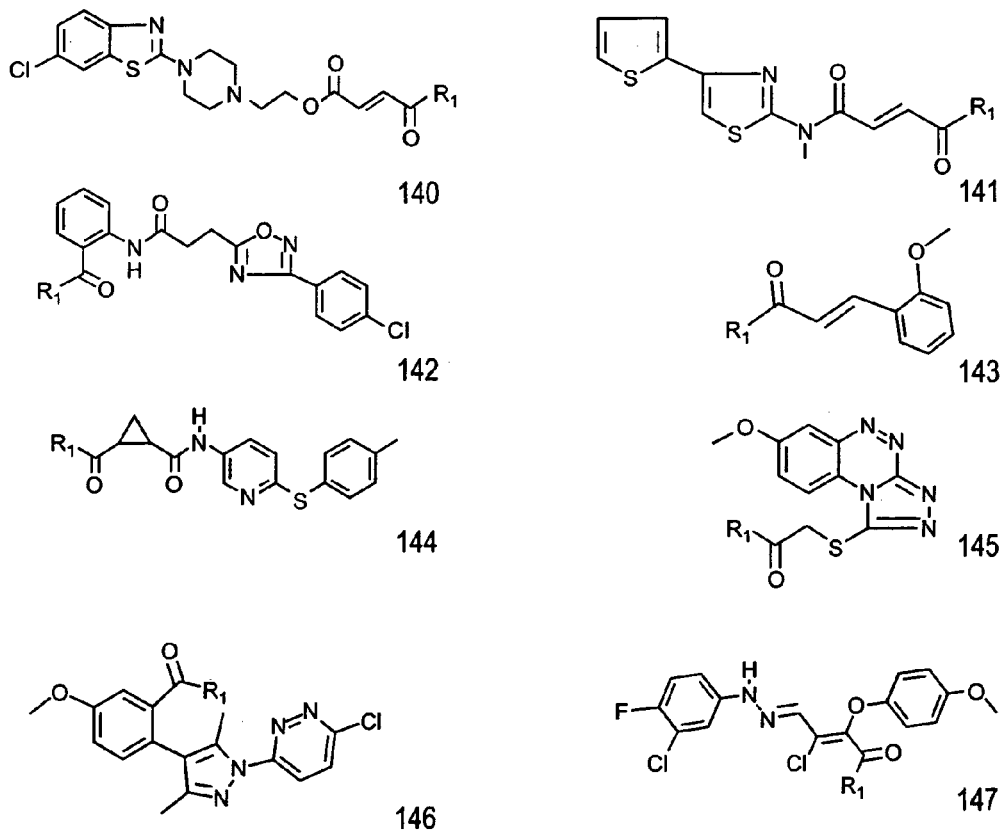
FIG. 16 shows a series of compounds (140–147) containing multiple ring head groups.
Figure 17:
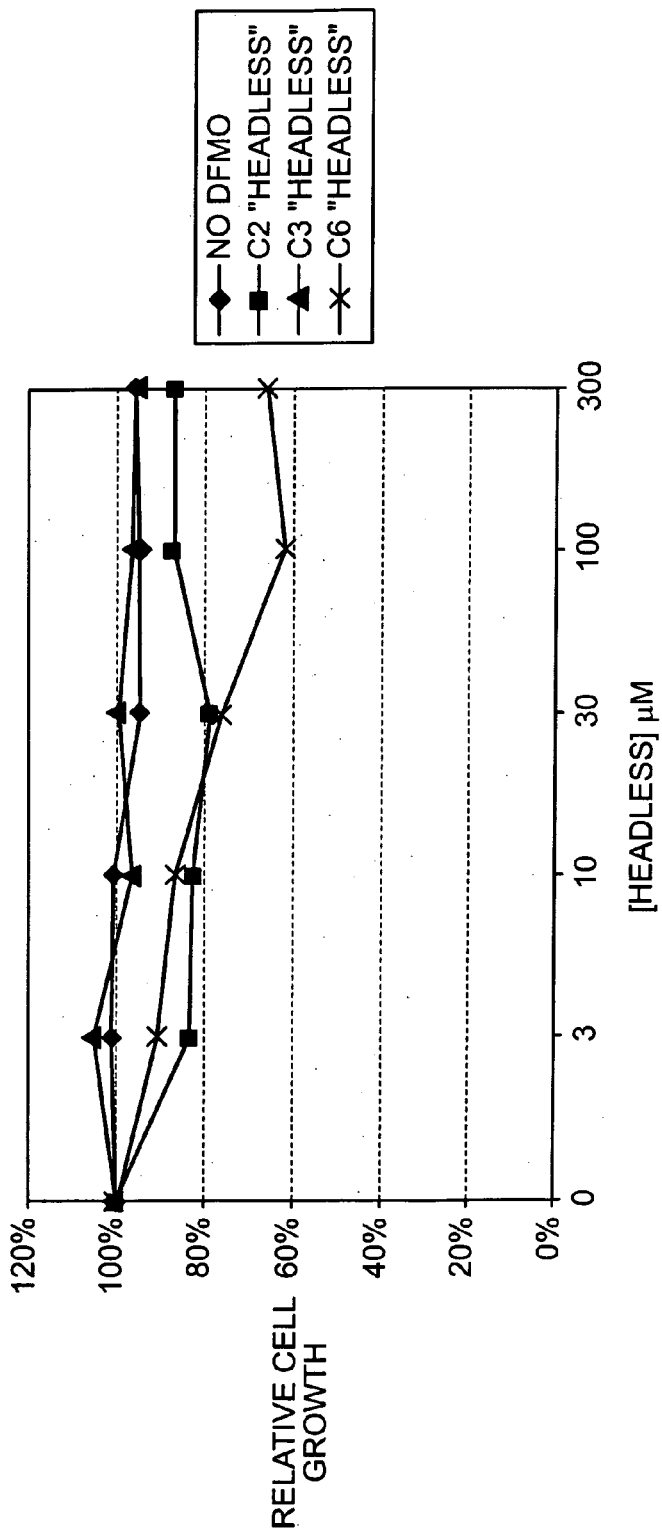
FIG. 17 is a graph showing the effects of DACS on growth of MDA breast cancer cells with and without DFMO.

Spacers X, Y and Z (for example FIG. 15, compounds 135–139) are defined as bonds or straight chain groups that attach different ring structures in a multiple ring head group. In some cases the spacers function as direct C—C or C—N attachments. Conventional spacers known in the art are similar to the linkers described herein. Known chemistries are used for covalent attachment of a ring structure in a head group with a spacer, for example, the formation of amide, sulfonamide, ether, thioether, ester, —C—C— and —C—N— and —N—N— bonds. $R_1$, $R_2$ and $R_3$ are typically alicyclic, aromatic, or heterocyclic rings when substituted in multi-ring head groups. These ring structures individually can also be substituted. Some of the multi-ring head group types described above are available from commercial sources, and examples are shown as structures 140 to 147 in FIG. 16. Alternatively, these or similar compounds are readily synthesized.

Linker Group

1. General Description

The linker portion of the compound can be represented by a general structure with an amino group at one end and an acid group on the other. One group of linkers contains diamino groups that are bonded via a urea linkage to the polyamine and via an amide, urea or sulfonamide linkage to the head group. The head group can also be bonded through other couplings such as ether, thioether and C—C bonds. The schematic structure shown above (in the section labeled "Head Groups, 1. General Description) shows the function of the linker moiety connecting the head group to the polyamine and possessing a desired length and combination of steric, conformational and hydrophobic properties. Also shown are the possible combination of coupling methods. Each coupling method can be used in combination with any of the three methods in FIG. 3 at the other position to result in a wide array of desired properties.

The linker group can have a range of properties that are reflected by the number of variations discussed below. Changes in the linker structure will be affect the properties of the whole polyamine analogue such as hydrophobicity, hydrophilicity, distance between head and polyamine portions, steric arrangement of head and polyamine portions, conformational properties, solubility and electronic properties.

2. Aliphatic Straight Chain Linkers

A series of linkers was been synthesized to test the effect of different distances between head group and polyamine. This series is most simply represented by the straight-chain aliphatic linkers having various carbon chain lengths shown below as compound 148).

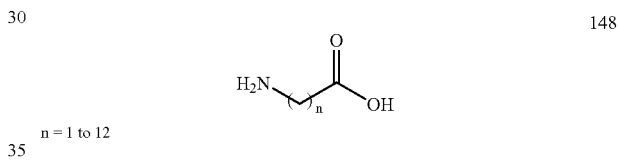

n = 1 to 12

148

Figure 18:
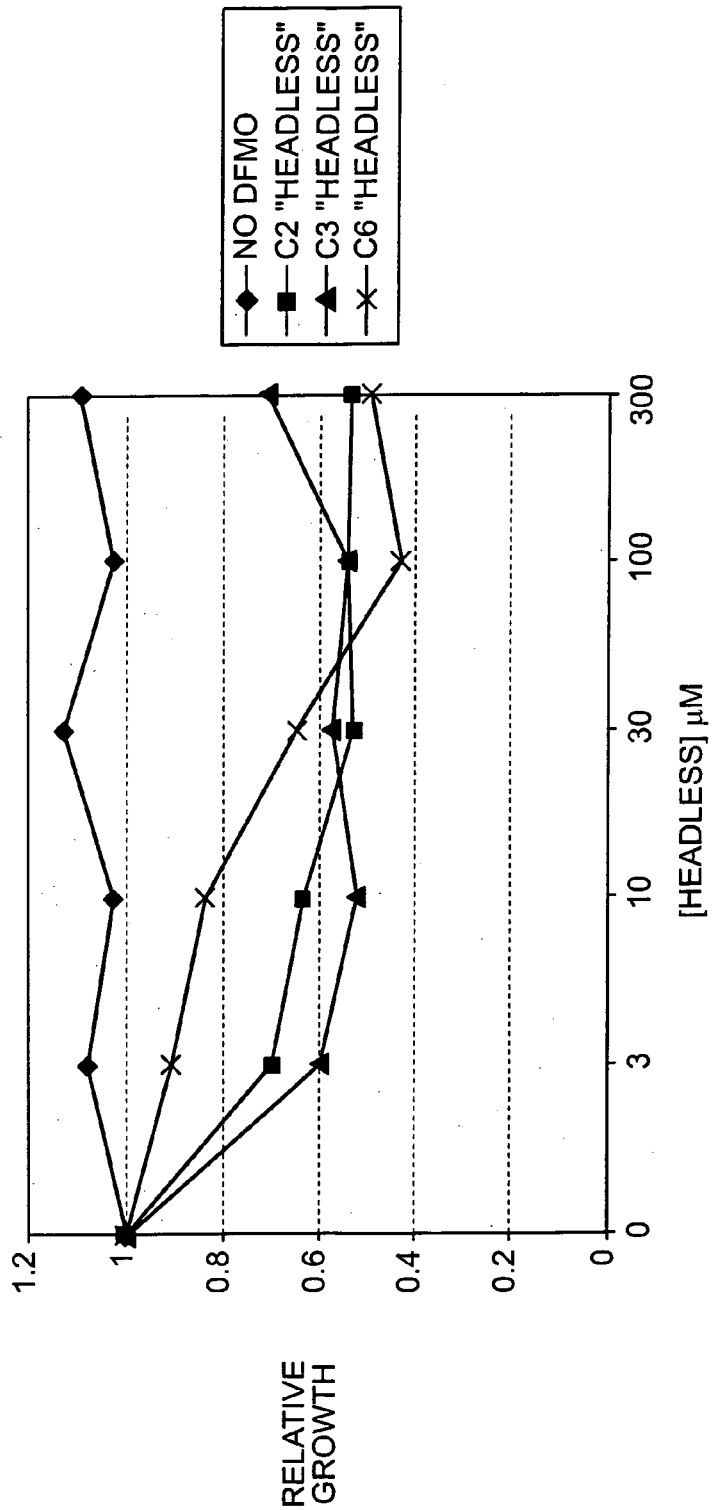
FIG. 18 is a graph showing the effects of headless polyamine analogues on growth of PC-3 prostate cancer cells with and without DFMO.

The present inventors discovered that linker length had dramatic effects on the PAT inhibitory activity and the cell growth inhibitory activity. A low $K_i$ is optimal for $C_6$ linkers in the presence of an aromatic head group. However, in the absence of a head group, differences in growth or transport inhibitory activities have not been dramatic. Thus, "headless" compounds have $K_i$s in the order of about 25 nM but have more attenuated inhibitory effects cell growth (breast cancer cell line) most likely due to their ability to actually be transported. The prostate cancer cell line is more powerfully inhibited by these "headless" inhibitors as shown in FIG. 18 and Example X. The C3-headless compound had dramatic effects on cell growth.

The synthetic route to this series of compounds, starting with various polyamines and head groups, is represented by the DACS 4 synthetic scheme depicted in FIG. 9 and discussed in more detail in Example VIII to XII). The amino group is protected by the N-tBoc group, and the carboxylic acid is then activated by forming the p-nitrophenyl ester. After acid deprotection of the N-tBoc group, the amino group can be reacted with an acid or sulfonamide chloride of the desired head group. After purification, direct reaction with the polyamine of choice in methanol gives the desired product. This can be purified by either (1) reverse-phase silica gel chromatography using 2:9 MeOH/0.5 N HCl or (2) cation-exchange chromatography over BioRex 70 resin ($NH_4$ form) using a linear gradient of from 0 to 2N $NH_4OH$.

3. Unsaturated Straight-Chain Aliphatic Linkers

Varying degrees of unsaturation (alkene and alkyne) together with the geometric isomers of the alkene derivatives can be introduced into the linker moiety as depicted below (149 and 150) These variations allow introduction of conformational restraint into the final product.

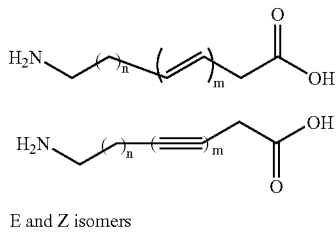

E and Z isomers where n=0 to 7 and m=1 to 4

4. Carbon-Substituted and Cyclic Aliphatic Linkers

Branched chain and cyclic saturated aliphatic linker groups impose conformational restraint on the desired polyamine analogue. Compounds 151 and 152 below illustrates this class of structure.

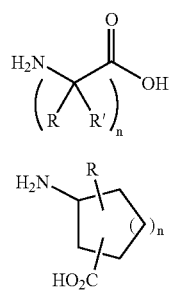

where n=1–10; R and R' vary independently and can be H or $CH_3(CH_2)_m$, and where m=1 to 10.

5. Chiral Carbon-Substituted Amino Acid Linkers

Figure 19:
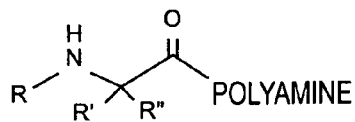
FIG. 19 lists amino acid-polyamine conjugates where the amino acid moiety may vary in chirality. These amino acids may also be used as "linkers" for attachment to other N-substituted "head groups".

Great structural diversity can be incorporated quickly into the polyamine analogues by using any of the large number of chiral amino acids that are available commercially. Many of the chiral amino acid intermediates to be used in the synthetic scheme shown in FIG. 9 are also available commercially, including some N-tBoc protected amino acids and some N-tBoc protected amino acid p-nitrophenyl esters. FIG. 19 (153) illustrates a variety of derivatives that have been produced by this method. These amino acid-polyamine conjugates contain variable chirality in the amino acid moiety. The amino acids can also be used as "linkers" to other N-substituted "head groups".

An additional thousand α-amino acid analogues known in the art can be used to form polyamine adducts. These are very easily incorporated into the present invention through the synthetic sequences described in FIGS. 8 and 9. Several key examples are; t-butylglycine, ornithine, α-aminoisobutyric acid, 2-aminobutyric acid, α-aminosuberic acid, 4-chlorophenylalanine, citrulline, β-cyclohexylalanine, 3, 4-dehydroproline, 3,5-diiodotyrosine, homocitrulline, homoserine, hydroxyproline, β-hydroxyaline, 4-nitrophenylalanine, norleucine, norvaline, phenylglycine, pyroglutamine, β-(2-thienyl)alanine, etc. Several important β-amino acids are easily incorporated into the present invention through the chemistry discussed above. A key example is β-alanine, etc.

Both stereoisomers of the natural L-amino acids (L=S) or D-amino acids (D=R) can be used in this invention. Because each isomer can be used individually, the structural diversity of the analogues is markedly enhanced.

6. "Headless" Linkers

The desired biological properties do not always depend upon the presence of a head group. Hence, a large series of so-called "headless" derivatives, containing a polyamine and linker without a head group were synthesized and tested. These derivatives are made by reacting the active ester (p-nitrophenyl or N-hydroxylsuccinimide) of the N-tBoc amino acid with the polyamine of interest. The resulting N-tBoc protected derivatives are then purified by cation-exchange chromatography over BioRex 70 ($NH_4$ form) resin using a linear gradient from 0 to 2N $NH_4OH$. The tBoc group can then be cleaved by acid treatment. Both the tBoc and acid deprotected derivatives can be tested for biological activity. The full series of amino acids discussed above, together with other derivatives have been synthesized. A more detailed discussion of the synthesis of $N^1$-[6-aminocaproylspermine] appears in Example XIII.

Figure 42:
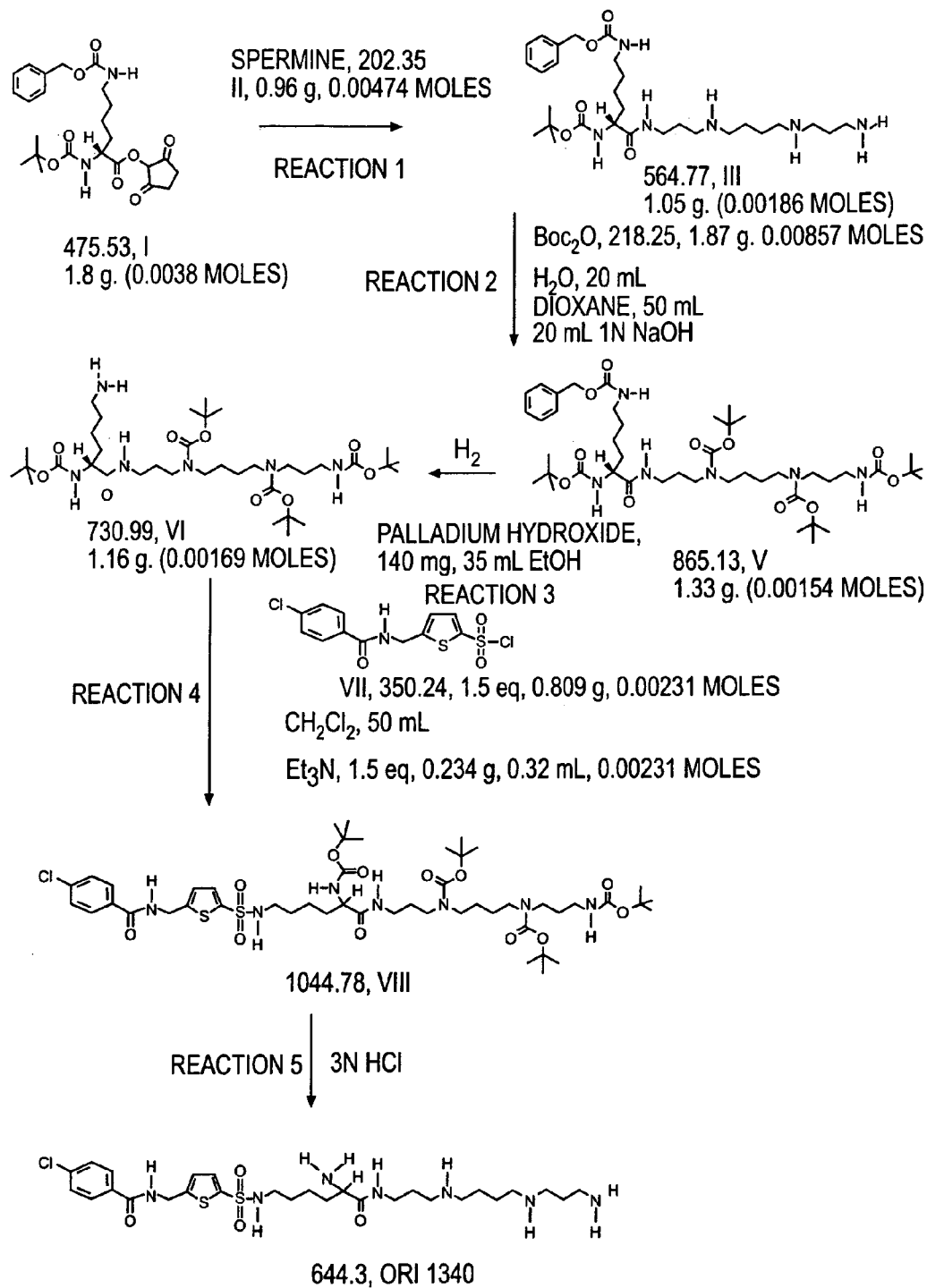
FIG. 42 shows a reaction pathway for the synthesis of analogue 1340.

Based on the above, a variety of polyamine analogues and derivatives have been produced and tested for the ability to function as polyamine transport inhibitors (see FIG. 42).

Reactive, Irreversible Polyamine Transport Inhibitors

A. Alkylating Reagents—

1. Aziridines

Polyamines substituted with fluorophores and other bulky end group were found to have the intrinsic property of high avidity binding to the PATr. This suggested that, in addition to utility as a diagnostic or research tool, they are useful as therapeutic agents for treating diseases or conditions wherein it is desirable to inhibit PAT. Their intrinsic affinity for other polyamine targets such as DNA broadens even further the scope of their therapeutic utility.

In a preferred embodiment the polyamine core is substituted with the aziridinyl group. The embodiment shown in FIG. 20 has a second substituent (a fluorophore such as dansyl or another bulky group). Aziridinyl-substituted polyamines react with nucleophilic groups in target binding complexes (receptors, transporters, enzymes and nucleic acids). In addition they can be exploited to bind other reactive moieties to polyamines. These mono- and di-substituted polyamine analogues are useful as drugs because of their inhibition of (a) the PATr, (b) polyamine synthesis and (c) reactions that use nucleic acids as substrates.

In one embodiment, a reactive group other than aziridine is introduced into a polyamine already substituted with a head group and a linker. This reactive group allows the labeled polyamine to bind covalently to an appropriate nucleophilic site on a polyamine-binding target molecule such as the PATr. Compounds of this type are used to covalently label receptors, enzymes or nucleic acids; thus, the modified polyamine serves as an affinity label that is useful in diagnostic assays and as a tool to isolate a polyamine binding target. Again, such compounds used as drugs will treat diseases or conditions which are ameliorated by blocking PAT or DNA-polyamine interactions. By virtue of the relative irreversibility of their binding, such compounds can be used at lower doses or at decreased frequency compared to compounds known in the art.

Disubstituted polyamines are synthesized by using the appropriate amine protecting groups on the polyamines. Reagents for the stepwise fuctionalization of spermine are known (Bergeron, R. J. et al., *J. Org. Chem.* 53: 3108–3111 (1988); Byk, G. et al., *Tetrahedron Lett.* 38: 3219–3222

(1997)). Bergeron et al. (supra) described the use of four independent amine-protecting groups: benzyl, t-butoxycarbonyl, trifluoroacetyl, and 2,2,2-trichloro-t-butoxycarbonyl. Conditions that allow the selective removal of each protecting group were also described. These reaction conditions allow independent and selective derivatization of each nitrogen of spermine. Thus this invention includes derivatization of monofunctionalized spermine with a linker/head group on any one of the four nitrogens and the synthesis of polyamine analogues with more than one functionalized nitrogen.

Methods to introduce an aziridine group into spermine (Li et al, *J. Med. Chem.,* 39:339–341 (1996) and into derivatives of spermidine (Yuan et al, *Proc. Am. Assoc. Cancer Res.,* 34: 380 (1993) are available. A synthetic scheme for $N^1$-(aziridinyl)-$N^{12}$-[($N^6$-dansyl)-6-aminocaproyl]spermine is shown in FIG. 20 (154–157).

Figure 20:
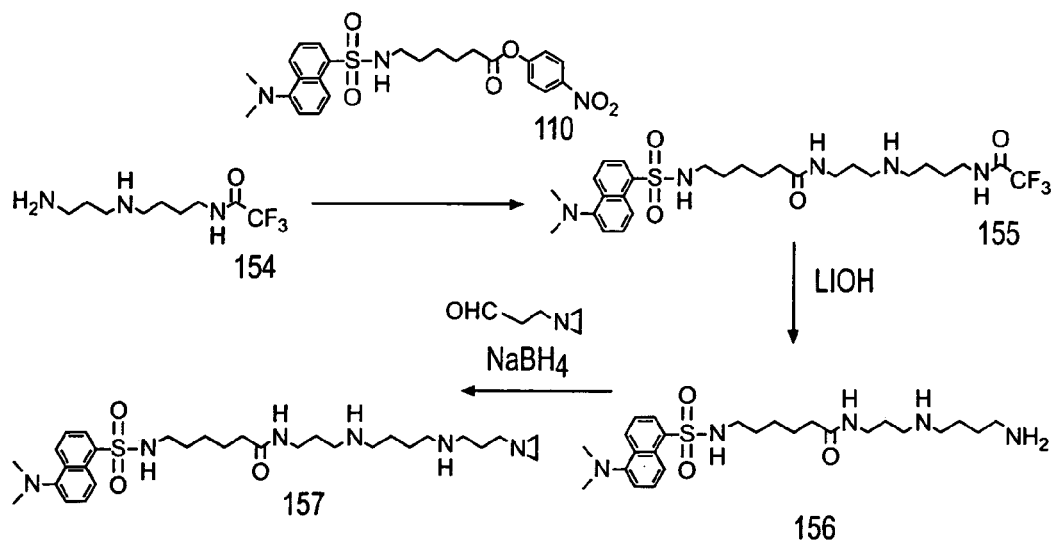
FIG. 20 is a scheme of the synthesis of $N^1$-(aziridinyl)-$N^{12}$-[($N^6$-dansyl)-6-aminocaproyl]spermine 157.
Figure 21:
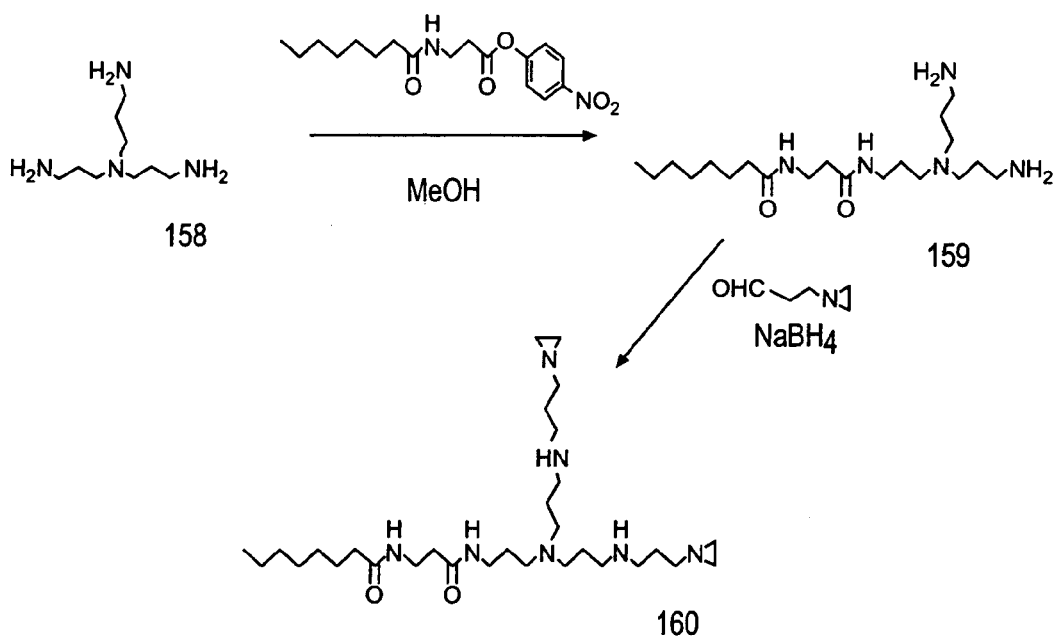
FIG. 21 is a scheme of the synthesis of a di-substituted aziridinyl polyamine analogue 160.

Whereas FIG. 20 shows the synthesis of the spermine derivative, any other polyamine derivative can be produced using an appropriately protected polyamine precursor, coupling to the linker/head group moiety and reductive amination with 3-aziridinepropanal. Removal of the protecting group(s) then gives the desired, reactive polyamine derivative. An additional example of this approach, illustrating the chemical flexibility it permits, is shown in the FIG. 21 (158–160).

3. Other Reactive Groups

Other useful moieties that can be added instead of the aziridine group and that react with nucleophiles to form covalent bonds include chloro-, bromo- and iodoacetamides, sulfonylfluorides, esters, nitrogen mustards, etc.

The chemically reactive 2-haloacetamide group can easily be introduced into any of the polyamine analogues by reaction with the appropriate 2-haloacetic acid halide. Other chemically reactive groups are described below.

B. Photochemically Activated Reagents

The use of photochemically activated functionalities on biologically active molecules is a well known (Fleming, S. A., *Tetrahedron* 51:12479–12520, 1995). In the polyamine field, Felschow et al attached an azidobenzoic acid moiety to spermine and examined the interaction of the resulting adduct with cell surface proteins (Felschow, DM et al. *Biochem. J.* 328, 889–895, 1997; Felschow, DM et al., *J. Biol. Chem.* 270:28705–28711, 1995). Since their photoprobe had an apparent $K_i$ of 1 μM versus spermidine for the PATr, the photolabeled proteins described were a mixture of polyamine binding proteins. One of the most potent PAT inhibitors of the present invention, DACS, has a Ki of <10 nM, which indicates an affinity 100 times higher than the compound reported by Felschow et al. Therefore introduction of a photoactivatable group to this molecule holds great promise in the isolation of the PATr protein(s).

1. Azide

Substitution of the dimethylamino group in dansyl chloride by azide produces a photochemically reactive chemical group. The preparation of 1-azido-5-naphthalene sulfonyl chloride has been described (Muramoto, K., *Agric. Biol. Chem.,* 1984, 48 (11), 2695–2699), and it is also available commercially from Molecular Probes Inc. (Eugene, Oreg.). Introduction of this compound into the synthetic scheme for DACS is straightforward and merely requires substitution for dansyl chloride.

This azido derivative, would enable isolation and characterization of the PATr protein(s), and would also find use as an irreversible, photoactivatable drug molecule.

2. Diaziridines

Substitution of a diaziridine group on the head group would accomplish many of the same goals as noted above.

3. Diazo Groups

Polyamine analogues with photoactivatible head groups are made using p-nitrophenyl 3-diazopyruvate, a reagent for introduction of a photoactivatable 3-diazopyruvate group to an aliphatic amine. This agent is also available from Molecular Probes, Inc. The desired derivative is made by reacting this reagent with the free amino, p-nitrophenyl activated linker precursor, purifying the linker/head group intermediate, and reacting it with the polyamine.

Analytical and Diagnostic Uses

The polyamine analogues and derivatives of the invention may also be used as reporter molecules and probes to assay other pharmacological targets, including soluble proteins, as described in PCT/US98/14896, which also describes the use of reporter head groups and polyamine transport assays.

Testing Inhibitors of Polyamine Transport

Through screening compounds made by the various synthetic routes described above, several compounds were found to effectively inhibit polyamine transport. DACS 4 is one such compound, with a $K_i$ 10 nM. To reinforce its effectiveness as a PAT inhibitor, DACS was tested as an inhibitor of cell growth (FIGS. 22–24; Example XX) in the presence and absence of polyamines or an ODC inhibitor, DFMO. "R" values were calculated as the ratio of the $IC_{50}$ in the absence of DFMO, or other polyamine synthesis inhibitor, over the $IC_{50}$ in the presence of DFMO, or other polyamine synthesis inhibitor (Example XIX). An "R" value of 1 reflects a polyamine transport inhibitor that shows no change in the presence of a polyamine synthesis inhibitor, suggesting that the transport inhibitor fails to inhibit the transporter or is not specific for the transporter.

Figure 43:
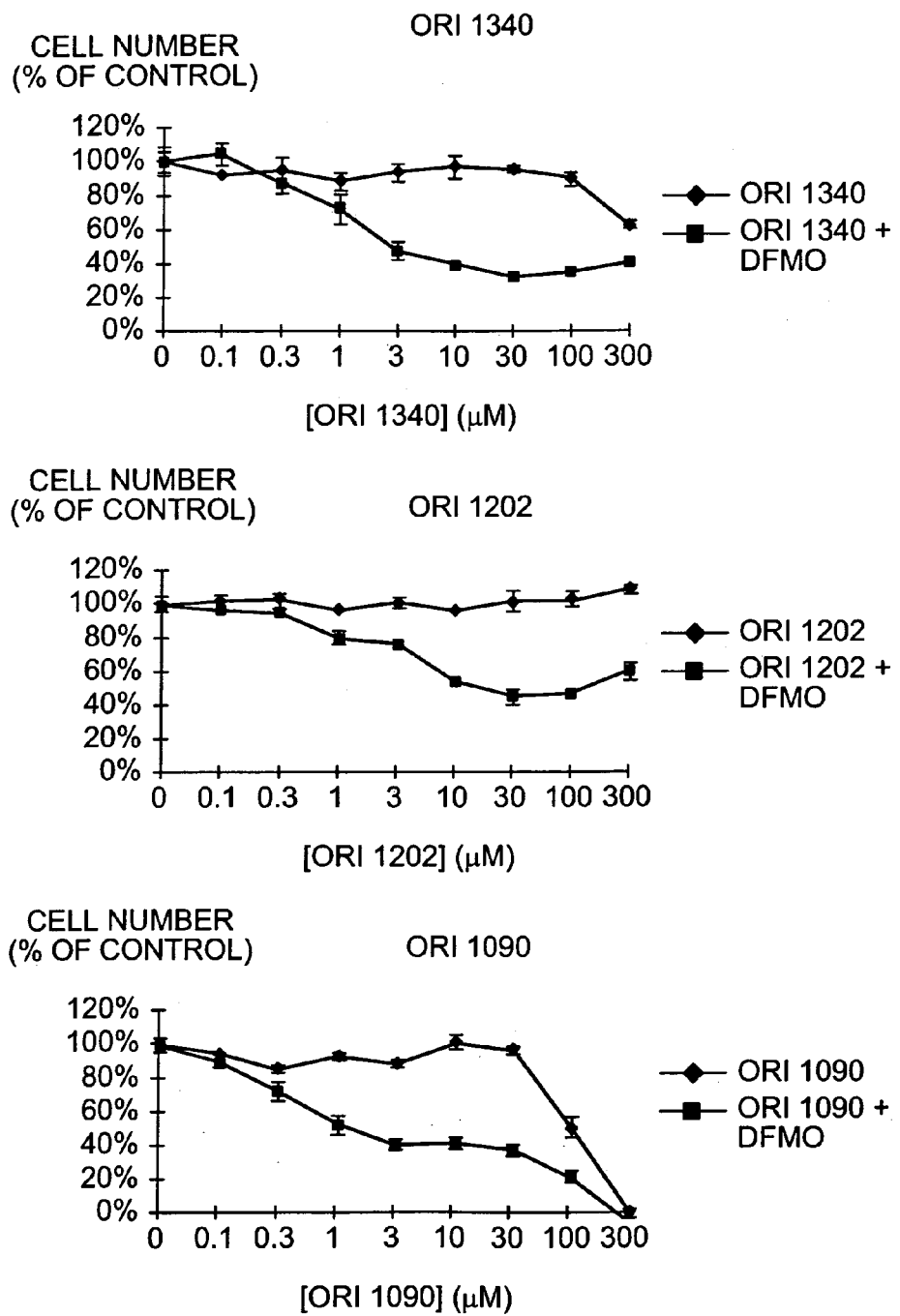
FIG. 43, panels A to C, shows the result of treating MDA-MB-231 cells with preferred polyamine analogues in the presence or absence of the polyamine synthesis inhibitor DFMO.

As expected, the presence of a polyamine synthesis inhibitor enhances the inhibition of cell growth by the polyamine transport inhibitors of the invention when used alone (see FIG. 43 for representative examples). A large enhancement reflects a good transport inhibitor that is specific for the polyamine transporter because it suggests that the transport inhibitor does not interact significantly with other cellular components. Preferred transport inhibitors of the invention will have "R" values of above about 2, but more preferably above about each of the following: 5, 10, 50, 100, 200, 300, and 400. Most preferred are compounds with "R" values of above about 500, above about 1000, or above about 10,000. Since significant "R" values may reflect conditions where neither the transport inhibitor nor the polyamine synthesis inhibitor alone are able to result in growth inhibition, the combination of the two may be considered to result in a synergistic effect, which varies according to the specificity of the transport inhibitor in combination with the specific synthesis inhibitor used. Such effects are not readily predictable in advance because the magnituide of inhibitory activity and degree of specificity are individual to each transport inhibitor.

The "R" values of the invention may also be considered in relation to the $IC_{50}$ values of this invention's polyamine transport inhibitors in the presence or absence of a polyamine synthesis inhibitor. Such a consideration provides useful information regarding the potential usefulness of the transport inhibitor as an active ingredient. Preferred is a review of the "R" value versus the $IC_{50}$ value in the presence of a polyamine synthesis inhibitor. This is useful because if that $IC_{50}$ value is too high, the transport inhibitor is unlikely to be a viable active agent because of the necessary high concentrations needed for inhibitory activity. This requirement for a high concentration would not necessarily be negated even by very high "R" values. Thus inhibitors of the invention are preferrably those that exhibit a $IC_{50}$ value of about 100 μM or less when used in combination with a polyamine synthesis inhibitor. More preferable are inhibitors that exhibit $IC_{50}$ values, in the presence of a polyamine synthesis inhibitor, of less than about each of the following: 75, 50, and 25 μM. Most preferred are compounds that exhibit $IC_{50}$ values, in the presence of a polyamine synthesis inhibitor, of less than about 10, less than about 5, less than about 1, less than about 0.5, less than about 0.1, less than about 0.05, and less than about 0.01 μM.

Using both a kinetic measure and a biological assay, the present inventors observed high correlation between the inhibition of PAT and growth. The three compounds 6, 4 and 5 in FIG. 2 (Example XIX) had the best combination of $K_i$'s (5, 10 and 10 μM, respectively) and R values (220, 400 and 210, respectively) as summarized below:

| Inhibitor | Ki (μM) | R |
|---|---|---|
| 6 | 5 | 220 |
| 4 | 10 | 400 |
| 5 | 10 | 210 |

Several other compounds unrelated to polyamines were shown to inhibit PAT by a non-competitive mechanism. These compounds (FIG. 25) include several antipsychotic drugs (trifluoperazine and thorazine). Compounds 161 and 162 had PAT inhibitory activity (see Example XXI). Compound 163, previously shown to be a PAT inhibitor, is also an antipsychotic drug.

Figure 26:
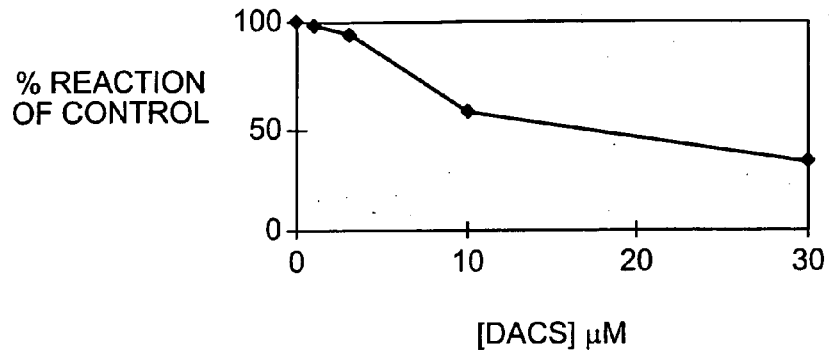
FIG. 26 is a graph showing the inhibition of spermidine/spermine acetyltransferase (SSAT) enzymatic activity by DACS.

Example XX describes the inhibition of spermidine/spermine acetyltransferase enzymatic activity by DACS (FIG. 26). Based on this, some of these compounds, if internalized, may serve a dual purpose.

The effect of various "headless" polyamine analogues were also evaluated and are described in Example XXII.

Pharmaceutical and Therapeutic Compositions

The polyamine analogues and derivatives of the invention, as well as the pharmaceutically acceptable salts thereof, may be formulated into pharmaceutical compositions. Pharmaceutically acceptable acid addition salts of the compounds of the invention which contain basic groups are formed where appropriate with strong or moderately strong, non-toxic, organic or inorganic acids in the presence of the basic amine by methods known in the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

As stated above, the compounds of the invention possess the ability to inhibit PAT or polyamine synthesis, properties that are exploited in the treatment of any of a number of diseases or conditions, most notably cancer. A composition of this invention may be active per se, or may act as a "pro-drug" that is converted in vivo to active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed. Pharmaceutical compositions designed for timed release may also be formulated.

Preferably, the compounds of the invention are administered systemically, e.g., by injection. When used, injection may be by any known route, preferably intravenous, sub-cutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, liquid containing capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral, including, topical, transdermal, intravaginal, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

Although the preferred routes of administration are systemic, the pharmaceutical composition may be administered topically or transdermally, e.g., as an ointment, cream or gel; orally; rectally; e.g., as a suppository, parenterally, by injection or continuously by infusion; intravaginally; intranasally; intrabronchially; intracranially intra-aurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topical application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to a target area, e.g., skin surface, mucous membrane, eyes, etc. This amount will generally range from about 0.001 mg to about 1 g per application, depending upon the area to be treated, the severity of the symptoms, and the nature of the topical vehicle employed.

The compositions of the invention be given in combination with one or more additional compounds that are used to treat the disease or condition. For treating cancer, the polyamine analogues and derivatives are given in combination with anti-tumor agents, such as mitotic inhibitors, e.g., vinblastine; alkylating agents, e.g., cyclophosphamide; folate inhibitors, e.g., methotrexate, pritrexim or trimetrexate; antimetabolites, e.g, 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical compositions comprising any known cancer therapeutic in combination with the polyamine analogues and derivatives disclosed herein are within the scope of this invention. Most preferably, the present compounds are administered in combination with a polyamine synthesis inhibitor such as DFMO.

The pharmaceutical compositions of the invention may also comprise one or more other medicaments such as anti-infectives including antibacterial, anti-fungal, anti-parasitic, anti-viral, and anti-coccidial agents.

Typical single dosages of the compounds of this invention are between about 1 ng and about 10 g/kg body weight. The dose is preferably between about 0.01 mg and about 1 g/kg body wt. and, most preferably, between about 0.1 mg and about 100 mg/kg body wt. For topical administration, dosages in the range of about 0.01–20% concentration of the compound, preferably 1–5%, are suggested. A total daily dosage in the range of about 1–500 mg is preferred for oral administration. The foregoing ranges are, however, suggestive, as the number of variables in regard to an individual treatment regime is large, and considerable excursions from these recommended values are expected and may be routinely made by those skilled in the art.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al, "Protocols for Screening Chemical Agents and Natural Products Against Animal Tumors and Other Biological Systems (Third Edition)", *Canc. Chemother. Reports*, Part 3, 3:1–112.

Synthetic Methods

The synthetic methods necessary to produce the polyamine analogues and derivatives of the invention, including parallel library synthesis and combinatorial approaches, have been described in PCT/US98/14896 and in FIG. 42. Additionally, this invention provides a new synthetic method whereby large quantities of an inhibitor may be readily produced (see FIG. 47 and Example XXXIII below). Briefly, the method uses tBoc protected polyamine derivatives as crude reaction intermediates that are sufficiently lipophilic to be purified by silica gel chromatography rather than ion exchange chromatography. Step-wise elution of the intermediates permits recovery of the various reaction products for subsequent deprotection.

Having now generally described the invention, the same will be more readily understood through reference to the following examples which are provided by way of illustration, and are not intended to be limiting of the present invention, unless specified.

EXAMPLE I

Synthesis of $N^1$-dansylspermine 3

Figure 7:
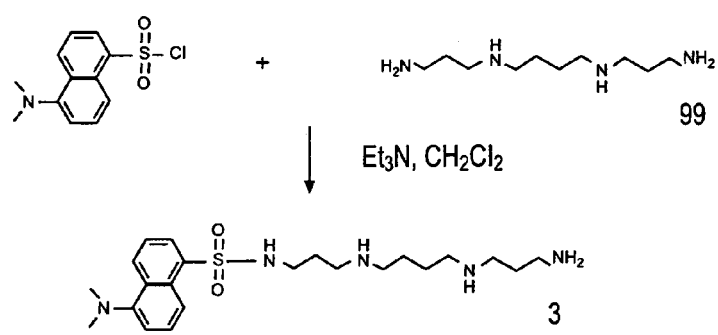
FIG. 7 shows a scheme of the synthesis of the synthesis of $N^1$-dansyl-spermine 3 (MDS).

Synthesis of $N^1$-dansylspermine is illustrated in FIG. 7. To 0.81 g (4 mmole) of spermine and 0.1 g (mmole) of triethylamine in 30 ml dry $CH_2Cl_2$ cooled down to 4C, was added dropwise 0.27 g (1 mmole) dansyl chloride dissolved in 20 ml dry $CH_2Cl_2$ over 90 minutes. The temperature was allowed to rise to ambient temperature and was stirred for 16 hours when it was filtered to remove triethylamine hydrochloride. The precipitate was washed with 25 ml $CH_2Cl_2$ and the combined $CH_2Cl_2$ extracts was extracted with 2×25 ml 5% $Na_2CO_3$ and 1×25 ml water. The $CH_2Cl_2$ was filtered through Whatman no 1 filter paper and evaporated to dryness to yield 0.45 g. Thin layer chromatography on silica gel in isopropanol: pyridine: acetic acid: water (4:1:1:2) showed no starting spermine and mainly two spots, when sprayed with 0.2% ninhydrin/ethanol. The material was dissolved in 8 ml 1.0 M ammonium acetate pH 7.4 and was chromatographed on a Biorad 70 weak cation exchanger (1.5×48 cm) using a pH gradient between 1.0 M ammonium acetate and 1.25 M hydrochloric acid over 500 ml with a flow rate of 0.5 ml per minute, collecting 8 ml fractions. Fractions containing a single spot were collected, adjusted to pH 10.5 and extracted with 2×25 ml $CH_2Cl_2$. This $CH_2Cl_2$ fraction was filtered through Whatman filter paper and evaporated to dryness. The solid product was dissolved in ethanol acidified with hydrochloric acid and recrystallized from ethanol to yield 0.14 g of $N^1$-dansylspermine (also termed monodansylspermine or "MDS"). The NMR spectrum confirmed the structure. The products can be purified by recrystallization with out any ion exchange chromatography.

EXAMPLE II

Synthesis of $N^1$-(1-pyrenylsulfonyl)spermine 15

Synthesis of $N^1$-(1-pyrenylsulfonyl)spermine) is illustrated in FIG. 5. To 0.56 g (2.8 mmole) of spermine and 0.069 g (0.69 mmole) of triethylamine in 25 ml dry $CH_2Cl_2$ cooled down to 4° C., was added drop-wise 0.20 g (0.69 mmole) dansyl chloride 1-pyrenesulfonyl chloride dissolved in 20 ml dry $CH_2Cl_2$ over 30 minutes. The temperature was allowed to rise to ambient temperature and was stirred for 16 hours when it was filtered to remove triethylamine hydrochloride.

The precipitate was washed with 25 ml $CH_2Cl_2$ and the combined $CH_2Cl_2$ extracts were evaporated to dryness and dissolved in ethyl acetate which was extracted with twice with 25 ml 5% $Na_2CO_3$ and once with 25 ml water. The ethyl acetate was filtered through Whatman no 1 filter paper and evaporated to dryness to yield 0.26 g.

Thin layer chromatography on silica gel in isopropanol: pyridine: acetic-acid:water (4:1:1:2) showed no starting spermine and mainly two spots, when sprayed with 0.2% ninhydrin/ethanol.

The material was dissolved in 8 ml 1.0 M ammonium acetate pH 7.4/MeOH 1:1 and was chromatographed on a Biorad 70 weak cation exchanger (1.5×48 cm) using a pH gradient between 1.0 M ammonium acetate pH 7.4 and 1.25

M hydrochloric acid/methanol (1:1) over 500 ml with a flow rate of 0.5 ml per minute, collecting 8 ml fractions. Fractions containing a single spot were collected, adjusted to pH 10.5 and extracted with 2×25 ml ethyl acetate. This ethyl acetate fraction was filtered through Whatman filter paper and evaporated to dryness. The solid product was dissolved in ethanol acidified with hydrochloric acid and recrystallized from ethanol to yield 0.10 g of N'-(1-pyrenylsulfonyl) spermine 3HCl. TLC indicated a single component and NMR spectrum confirmed the structure.

EXAMPLE III

Synthesis of $N^1$-((1-carbonyl)-4-(1-pyrenyl)butane) spermine 37

Figure 6:
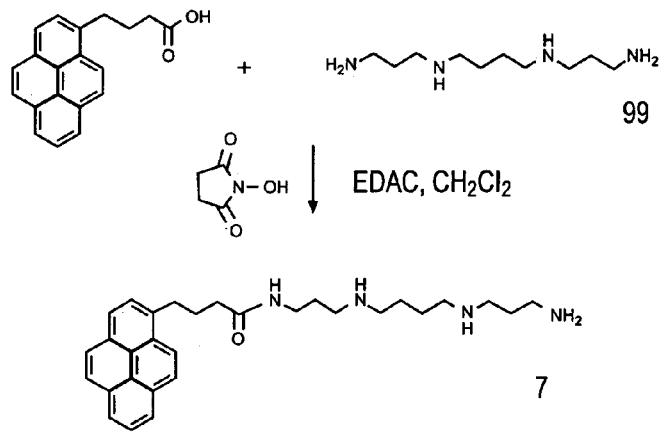
FIG. 6 shows a scheme of the synthesis of $N^1$-((1-carbonyl)-4-(1-pyrenyl)butane)spermine 7

Synthesis of $N^1$-((1-carbonyl)-4-(1-pyrenyl)butane)spermine is illustrated in FIG. 6. To 0.29 g (1 mmole) of 1-pyrenebutyric acid dissolved in $CHCl_3$ with heating were added 0.19 g (1 mmole) of EDC 0.12 g (1 mmole) of N-hydroxysuccinamide and was stirred at room temperature for 30 minutes when this solution was added drop-wise to 0.82 g (4 mmole) spermine dissolved in 20 ml $CHCl_3$. The reaction was allowed to proceed for another 4 hours when it was diluted with an equal volume of ethylacetate. This solution was extracted with 25 ml 5% $Na_2CO_3$ and once with 25 ml water. The organic solution was filtered through Whatman no 1 filter paper and evaporated to dryness to yield 0.25 g.

Thin layer chromatography on silica gel in isopropanol: pyridine:acetic acid:water (4:1:1:2) showed no starting spermine and mainly two spots, when sprayed with 0.2% ninhydrin/ethanol.

The material was dissolved in 8 ml 1.0 M ammonium acetate pH 7.4/methanol 1:1 and was chromatographed on a Biorad 70 weak cation exchanger (1.5×48 cm) using a pH gradient between 1.0 M ammonium acetate and 1.25 M hydrochloric acid/methanol (1:1) over 500 ml with a flow rate of 0.5 ml per minute, collecting 8 ml fractions. Fractions containing a single spot were collected, adjusted to pH 10.5 and extracted with 2×25 ml ethyl acetate. This ethyl acetate fraction was filtered through Whatman filter paper and evaporated to dryness. The solid product was dissolved in ethanol acidified with hydrochloric acid and recrystallized from ethanol to yield 0.13 g of $N^1$-((1-carbonyl)-4-(1-pyrenyl)butane)spermine. TLC indicated a single component and NMR spectrum confirmed the structure.

EXAMPLE IV

N-(1-anthracenyl)-N'-(N1-spermidyl)urea (9)

Synthesis of N-(1-anthracenyl)-N'-(N1-spermidyl)urea is illustrated in FIG. 4. A solution of 1 g of 1-aminoanthracene (5.2 mmole) and 1.04 g p-nitrophenyl chloroformate (5.2 mmole) in 100 ml benzene was refluxed using an air condenser until no more HCl gas escaped as measured with pH paper (3 hours). The desired product, N-(1-anthracenyl)-O-(p-nitrophenyl)urea (1.6 g; 86% yield) was filtered from the cooled reaction and washed with benzene. This product was used without further purification.

To 0.5 g (2.5 mmole) spermine in 30 ml dichloromethane was added drop-wise 0.18 g (0.5 mmole) of the urethane in 20 ml dichloromethane. The reaction was allowed to proceed for 16 hours when it was extracted 2×50 ml 5% $Na_2CO_3$ solution followed by 1×50 ml water. The filtered solution was evaporated to dryness on a high vacuum. The residue was dissolved in MeOH and acidified with 4 equivalents of 6N HCl acid solution. This solution was evaporated to dryness and was then recrystallized from EtOH/MeOH to yield 27.5 mg of compound that showed mainly one spot on silica gel TLC (isopropanol:pyridine:acetic acid:water; 4:1: 1:2).

EXAMPLE V

N-($N^1$-spermidyl)-2-(naphthoxy)acetamide (104)

The same synthetic is carried out using as starting material (2-naphthoxy)acetic acid, N-hydroxysuccinimide ester, so that the product is N-($N^1$-spermidyl)-2-(naphthoxy)acetamide as shown below:

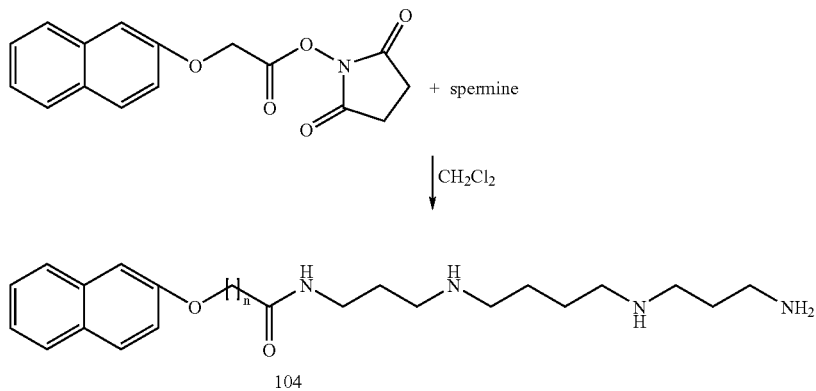

104

Using known chemistries the chain length can be increased as desired. A preferred length is n=1 to 10.

EXAMPLE VI

Synthesis of O-(Fluorenylmethyl)-N-(N-1-spermidyl)urethane

A synthetic scheme as described in Example II is carried out using starting compound 9, fluorenylmethyl chloroformate instead of 1-pyrenylsulfonyl chloride as shown below.

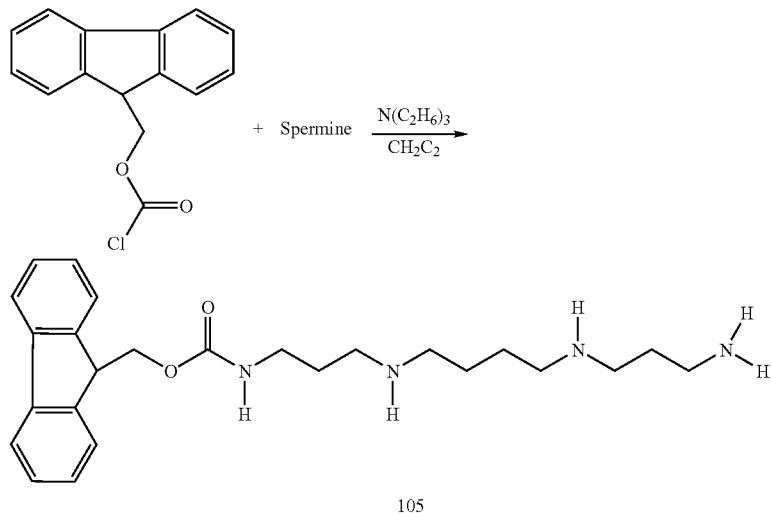

105

EXAMPLE VII

Disubstituted functionalizable compounds are well known in the art, for example sulfonyl chlorides, benzoyl chlorides, cyanates, thiocyanates, etc. The reaction of 2,6-naphthalene disulfonyl chloride with spermine is shown below.

diluted with 30 ml $CHCl_3$ and was extracted 2×50 ml 5% $Na_2CO_3$ solution followed by 1×50 ml distilled water. The organic phase was filtered and evaporated to dryness. The residue (0.20 g) was dissolved in 7 ml methanol and acidified with 5 equivalents of 6N HCl. The solvent was evaporated and the solid was recrystallized from ethanol/methanol gave 0.073 g (39% yield) of the desired product.

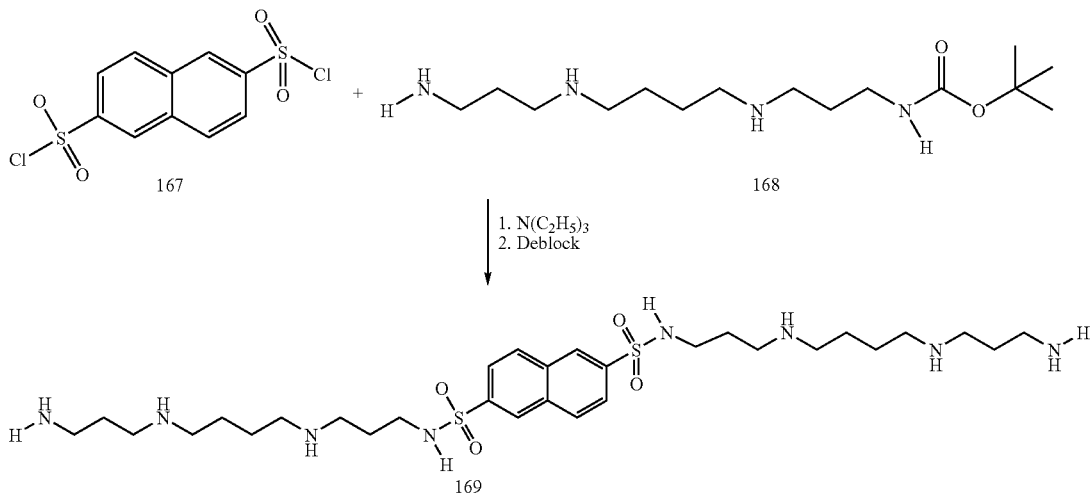

EXAMPLE VIII $N^1$-[($N^6$-dansyl)-6-aminocaproyl]spermine (DACS 4) by Method 1

Synthesis of DACS by method 1 is illustrated in FIG. 8. The reactants and product are shown below. To 0.55 g spermine (2.7 mmole) in 20 ml dichloromethane cooled in an ice bath was added drop-wise 0.125 g of N6-(dansyl)-6-aminocaproyl-N-hydroxysuccinimide ester (0.27 mmole) dissolved in 10 ml dichloromethane over 30 minutes. The reaction was stirred for 16 hours at ambient temperature when it was filtered to remove precipitate. The filtrate was Silica gel TLC in isopropanol:pyridine:acetic acid:water (4:1:1:2) showed a single fluorescent spot which also gave a ninhydrin positive spot. Nominal mass spectrometry, ion pair reversed phase chromatography and NMR confirmed the identity and purity of the compound.

EXAMPLE IX

4-Nitrophenyl 6-(N-(t-butoxycarbonyl)amino)hexonate 108

This compound, illustrated as an intermediate to DACS is shown in FIG. 9. To a dry round-bottom flask was added 11.55 g (50 mmol) of 6-(N-(t-butoxycarbonyl)amino)hexanoic acid 1 (available from NovoCalbiochem), 12.4 g (60 mmol) of dicyclclohexylcarbodiimide and 8.35 g (60 mmol) of 4-nitrophenol. To these solids was added 150 mL of dry EtOAc under argon at r.t. to produce an off-white heterogeneous suspension. After 3 h at r.t. the solid DCU was filtered off through a pad of Celite and this pad was washed 3× with 50 mL of EtOAc. The combined filtrates were evaporated to give 27 g yellow solid. This was crystallized from 200 mL of abs. EtOH to give 13.54 g (77%) white solid as first crop. TLC (silica gel, $CHCl_3$) Rf 0.7. NMR confirmed the identity of the compound.

EXAMPLE X

4-Nitrophenyl 6-aminohexonate trifluoroacetate salt 109

This compound, illustrated as an intermediate to DACS is shown in FIG. 9. To a solution of 5.0 g (14.2 mmol) of 108 in 30 mL of $CH_2Cl_2$ was added 15 mL of trifluoroacetic acid at r.t. Many bubbles formed in the clear reaction solution. After 1 h the solvents were removed under reduced pressure to give a clear oil. This oil was triturated with diethyl ether to form a white waxy solid which was dried under high vacuum. TLC (Rf 0.05 in 10% MeOH in $CHCl_3$) showed the product was pure enough for the next step. Yield 5.25 g white solid (100%).

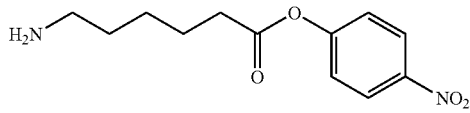

EXAMPLE XI

4-Nitrophenyl 6-(N-(dansyl)amino)hexonate 110

This compound, illustrated as an intermediate to DACS is shown in FIG. 9. To the suspension of 4.2 g (11.5 mmol) of 109 in 50 mL of dry $CH_2Cl_2$ was added 3.71 g (13.8 mmol) of dansyl chloride as a solid, followed by 4.8 mL (34.5 mmol) of dry Et3N dropwise through a syringe under argon at r.t. The resulting yellow solution was stirred at r.t. for 18 hr. when the solvents were evaporated to give a green oily solid. This material was dissolved in 250 mL of $CHCl_3$ and washed with 100 mL of 0.1 N HCl, $H_2O$ then brine. The organic layer was dried and evaporated to give 5.85 g green oily solid. This was crystallized from 100 mL of abs. EtOH to give 2.136 g (38%) yellow solid from the first crop. The mother liquor can be crystallized for a second crop or purified by column chromatography on silica gel using $CHCl_3$ then 10% EtOAc in $CHCl_3$ for additional pure product. M.p. 84–86C. NMR confirmed the identity of the compound.

EXAMPLE XII

$N^1$-[($N^6$-dansyl)-6-aminocaproyl]spermine (DACS 4) by Method 2

This synthetic method is illustrated in FIG. 9. To a clear solution of 72.8 mg (0.36 mmole) of spermine in 2 mL of MeOH is added 2.0 mL of 0.15 M MeOH solution (0.30 mmol) of 110 dropwise at r.t. After 1 drop was added a very bright yellow color appeared. This yellow solution was stirred for 15 min. when the solvent was evaporated to give 220 mg of a yellow, oily solid. The crude product was dissolved in 1.0 mL of 0.5 M HCl and applied to a 1×36 cm column of C-18 RP silica gel (Bakerbond #7025–01) in 20/80 MeOH:0.5 M HCl. Elution with the same solvent gave 79 mg (38%) pure hydrochloride salt as a white solid. TLC using 4/1/1/2 isopropanol:acetic acid:pyridine:$H_2O$ gives an Rf of 0.70 for DACS, 0.90 for diacyl side product and 0.18 for spermine. NMR confirmed the identity of the compound.

EXAMPLE XIII

$N^1$-[6-aminocaproylspermine] 171

This reaction scheme is carried out as described in detail below.

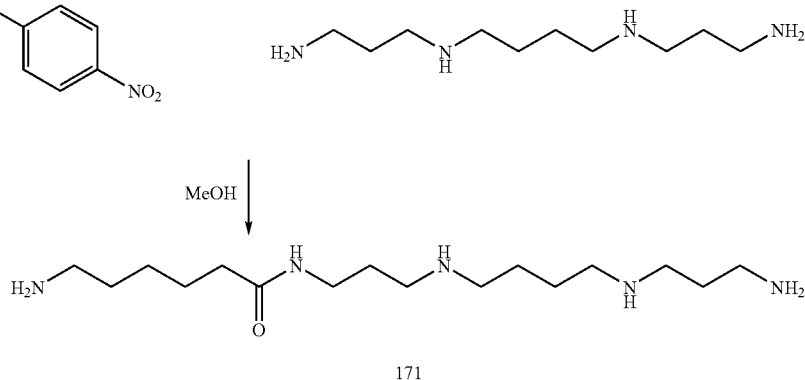

171

To a clear solution of 125 mg (0.62 mmol) of spermine in 5.0 mL of MeOH was added a suspension of 181 mg (0.52 mmol) of 3 in 5.0 mL of MeOH. The resulting bright yellow solution was stirred at r.t. for 15 min. when the solvents were evaporated. The resulting yellow solid was dissolved in 10 mL of $H_2O$ and applied to 1×30 cm column of BioRex 70 ($NH_4^+$ form) resin. Elution was performed by a linear gradient of 0 to 1 N NH4OH. The product containing fractions were evaporated to give 181 mg of N-t-Boc intermediate that was contaminated with 4-nitrophenol. This material was dissolved in 3.0 mL of $H_2O$ and 3.0 mL of 6 N HCl was added at r.t. After 2 h at r.t. the clear solution was extracted 3× with 5 mL of $CHCl_3$, 1× with EtOAc then 1× with $CHCl_3$ again. The aqueous layer was then evaporated to give 220 mg (92%) white solid. NMR confirmed the identity of the compound.

EXAMPLE XIV

Parallel Combinatorial Library Synthesis

The general reaction involved in the parallel synthesis is shown in the reaction below:

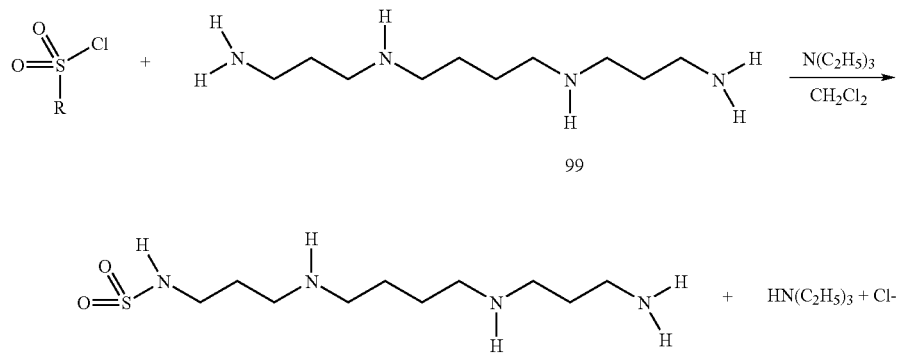

99

In each of three 10 ml reaction vials (React-Vial™ Pierce, Rockford, Ill.) were placed 0.74 mmol of spermine and 0.15 mmol of triethylamine. Similarly in three additional reaction vials were placed 0.74 mmol of spermine and 0.15 mmol of triethylamine. Similarly in three additional reaction vials were also placed 0.74 mmol of putrescine and 0.15 mmol triethylamine. To each of these flask were added 2.5 ml dry $CH_2Cl_2$ and the flasks were closed with a septum and cooled down to −20° C. in a React-block™ aluminum block for 45 minutes, when it was placed in a Reacti-Therm™ Heating/Stirring Module, with heating switched off. Three acid chlorides (1-naphthylsulfonyl chloride, 2-naphthylsulfonyl chloride and 10-camphorsulfonyl chloride) in 2.5 ml $CH_2Cl_2$ were added dropwise over 15 minutes via a 2.5 ml syringe (All-PP/PE, Aldrich, Milwaukee, Wis.) through the septum to each of spermine and putrescine. Each vial contained also an exhaust consisting of a 2.5 ml syringe filled with anhydrous $CaCl_2$ with out the plunger. The reactions were allowed to proceed for 16 hours at ambient temperature when it was extracted 2×2.5 ml 5% sodium carbonate solution followed by 2×2.5 ml water. To the organic solvents were added 2.5 ml methanol and 5 equivalents of a 6N HCl solution. The solvent was evaporated with argon and dried on a high vacuum. Silica gel TLC with isopropanol:acetic acid:pyridine:water 4:1:1:2 showed mainly one component with either UV/fluorescence or 0.2% ninhydrin in ethanol staining. Purity was estimated as to be greater than 80%. The structures, yield and inhibition of the polyamine transporter is shown in Table 1, below.

EXAMPLE XV

Parallel Library Synthesis (a)

Using the Reacti-Therm™Heating/Stirring Module triple module, twenty four 10 ml vials are used at the same time, thereby increasing substantially the number of compounds that can be synthesized in parallel. In addition more than one of these modules can be used at the same time. Using this approach with the commercially available amines listed below and other amines synthesized as described above, libraries of compounds are synthesized with commercially available sulfonyl chlorides (from Aldrich Chemical Company, Maybridge Chemical Company, Ryan Scientific Inc., to name a few) in a manner as described in Example I.

| List of Polyamines: |
| --- |
| N-(3-aminopropyl)-1,3-propanediamine, |
| N,N'-bis(3-aminopropyl)piperazine |
| N,N'-bis(2-aminoethyl)-1,3-propanediamine |
| Tris(2-aminoethyl)amine |
| N,N'-bis-(3-aminopropyl)ethylenediamine |
| N,N'-bis(3-aminopropyl)-1,3-propanediamine |
| Tris(3-aminopropyl)amine |

TABLE 1

Structures, Yield and Inhibition of the Polyamine Transporter in MDA-MB-231 Cell Line

| Compound | % Yield | Ki μM |
| --- | --- | --- |
|  | 94.6 | 0.19 |

TABLE 1-continued

Structures, Yield and Inhibition of the Polyamine Transporter in MDA-MB-231 Cell Line

| Compound | % Yield | Ki μM |
|---|---|---|
| (naphthalene-1-sulfonamide with butylamine linker) | 84.8 | >30 |
| (naphthalene-2-sulfonamide with spermine-like polyamine) | 82.6 | 0.15 |
| (naphthalene-2-sulfonamide with butylamine linker) | 88.8 | 5 |
| (camphorsulfonamide with spermine-like polyamine) | 59.6 | >10 |
| (camphorsulfonamide with butylamine linker) | 79.9 | >30 |

EXAMPLE XVI

Parallel Library Synthesis (b)

A library is synthesized as in Example I, with carboxylic halides in the place of the sulfonyl chlorides, as indicated below. Useful carboxylic halides are commercially available from varies source.

EXAMPLE XVII

Synthesis of Library of N'-"head group"-N"-(N1-spermidyl)urea

A synthesis of the type shown in Example IV is carried out, with the difference that the starting urethanes are first synthesized in parallel using different aromatic amines as processors.

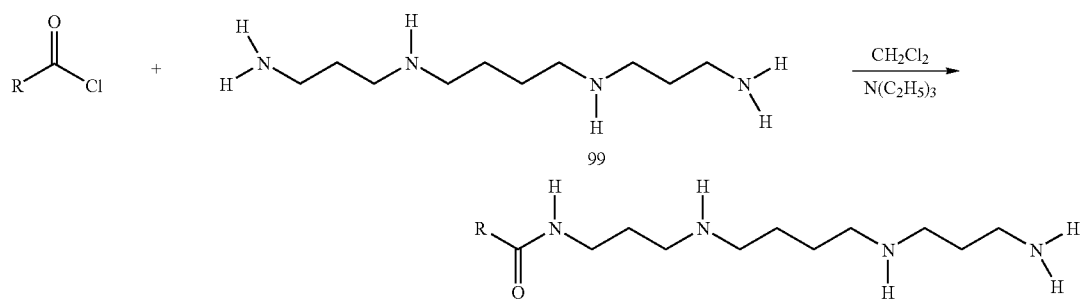

EXAMPLE XVIII

Cell Growth and its Inhibition by Polyamine Analogues

The present investors have developed a growth assay to use in screening for transport inhibitors that are synergistic with ODC inhibitors. The estrogen insensitive human breast carcinoma MDA-MB-231 cell line as the primary cell line in the screen. This cell line, as with many breast cancers, has a high rate of polyamine transport (*Anticancer Res* (1991) 11:1807–1814). In order to optimize the screen for polyamine transport inhibition, 1.0 µM spermidine was added to media to reverse the effects of ODC inhibitors. The assay was also performed over seven days because this allows for the greatest dynamic range in cell growth due to the mechanism of ODC inhibitors. Cells need to divide several times before the intracellular level of polyamines begin to decrease to growth inhibitory levels. Therefore, growth does not significantly cease until the third to fourth day.

When used to screen for polyamine transport inhibitors, the growth assay alone does not verify a reduction of polyamine uptake. Therefore, the growth assay and a kinetic transport assay have been used to validate transport inhibition.

Figure 22:
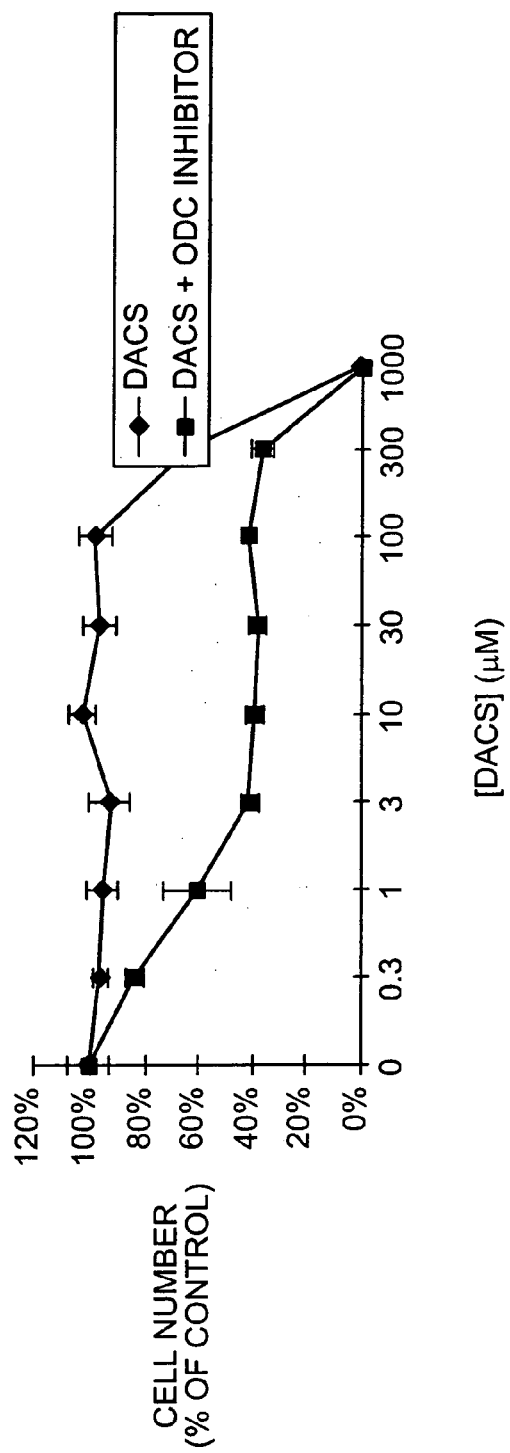
FIG. 22 is a graph showing inhibition of the growth of MDA-MB-231 cells, by DACS in the presence (■) or absence (♦) of the polyamine synthesis inhibitor DFMO. See also, FIGS. 2/1–2/10 for the effects of a large number of polyamine analogues on PAT and tumor cell growth. Cells were plated in the presence of varying concentration of DACS with and without 1 mM DFMO. Cells numbers (expressed as % of controls) were determined after 6 days as above.

A. DACS Inhibits Polyamine Transport and Acts Synergistically with ODC Inhibitors Screening of thousands of compounds has permitted the present inventors and their colleagues to identify a transport inhibitor that inhibits spermidine uptake with a $K_i$ of 8 nM, putrescine uptake with a $K_i$ of 5.4 nM and has an $IC_{50}$ of 0.6 µM for growth in combination with an ODC inhibitor (FIG. 22). Over 100 analogues of this compound have been synthesized and SAR data has been accumulating around the structural features necessary to inhibit polyamine uptake. Additional compounds have been discovered with even greater potency than DACS, but not as exhaustively studied as described below. Under the assay conditions described above, with 1.0 µM supplemented polyamines, there is no growth reduction due to ODC inhibition alone. In addition, DACS is not growth inhibitory alone until very high concentrations (300 µM) are reached. DACS makes the previously ineffective ODC inhibitors very effective as growth inhibitors in the presence of polyamines.

Growth inhibition by the combination of DACS and an ODC inhibitor in the presence of polyamines (FIG. 23) mimics the effects of the ODC inhibitor in the absence of significant extracellular polyamines. Growth inhibition began to appear at day 2 and cell growth was reduced 69% by day 3. Growth eventually reached a plateau with the ODC inhibitor combined with DACS but continued in the absence of DACS. This effect appears to be cytostatic in this cell line but, for prolonged periods of time, may be cytotoxic.

B. DACS is Effective in the Presence of Natural Polyamines

Extracellular spermidine, spermine and putrescine can reverse the effects of ODC inhibitors through increased uptake into the cell. The major excreted forms of polyamines ($N^1$-acetylspermine and $N^1$-acetylspermidine) can also reverse the effect of ODC inhibitors. DACS prevents the natural polyamines, putrescine, spermidine, $N^1$-acetylspermine and $N^1$-acetylspermidine, from rescuing the cells from ODC inhibition. This is significant for several reasons. Reports in the literature suggest that there are more than one transporter. If this is true, DACS is effective at blocking the uptake of all of the polyamines at low concentrations.

C. DACS is Effective Against Several Types of Cancers

Figure 24:
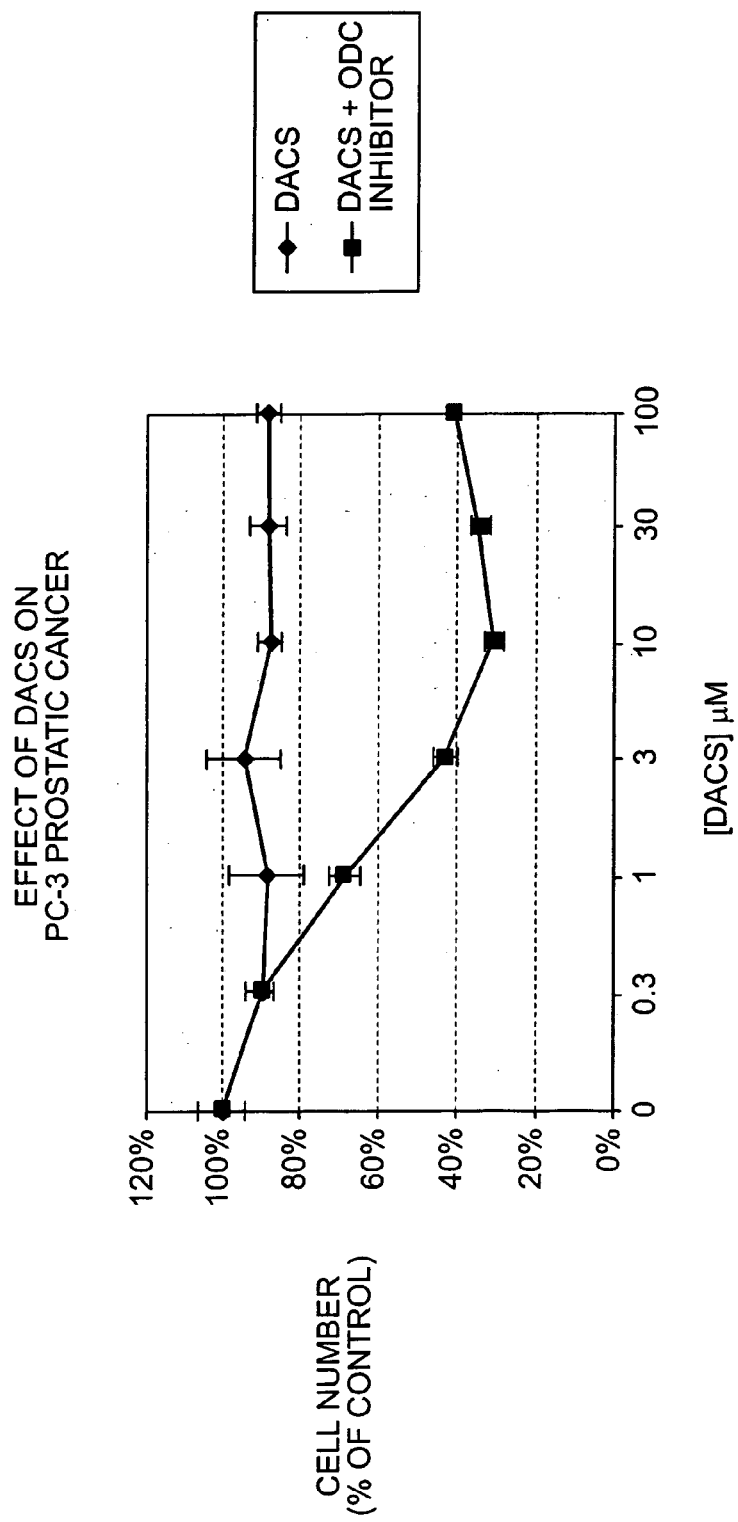
FIG. 24 is a graph showing the inhibition of growth of PC-3 prostate cancer cells by the combination of DACS and DFMO. See description of FIG. 22 for conditions and details.

DACS was tested in vitro in combination with ODC inhibitors against several human cancer cell lines. These include T-cell acute lymphoblastic leukemias (ALL), glioblastomas, prostate, and colon cell lines. DACS is effective against all these tumor cell lines in vitro FIG. 24 shows the effects of DACS on PC-3 prostate cancer cells.

EXAMPLE XIX

Screening of Polyamine Analogues in Transport and Growth Assays

The effect of a number of potential PAT transport inhibitors on PAT and growth of MDA cells is summarized in FIG. 2 (3–98). The ratio "R" is the $IC_{50}$ for polyamine alone relative to the $IC_{50}$ for the polyamine analogue combined with an ODC inhibitor. This value of "R", indicates the relative level of "synergism" between the polyamine analogue and ODC inhibitor. Under the growth assay conditions, the ODC inhibitor alone shows no inhibition.

EXAMPLE XX

Transport Inhibitors Inhibit Polyamine-Utilizing Enzymes

A study was conducted to determine whether the compositions of the present invention, designed as PAT inhibitors, had other activities on the PA system. Specifically, the ability of DACS to inhibit an enzyme involved in PA recycling was evaluated. The method used was as described in Casero, R. A. et al., *Biochem. J.* 270:615–620 (1990) hereby incorporated by reference in its entirety. This assay measures the incorporation of $^{14}C$-labeled acetyl CoA into spermidine to form acetylspermidine. Varying concentrations of DACS were added to a reaction mixture containing HEPES buffer, pH 7.8, 1 mM spermidine, and 1 mM $^{14}C$-Acetyl CoA. The product is isolated by binding to phosphocellulose filter paper and the extent of reaction is determined by scintillation counting.

As shown in FIG. 26, DACS inhibited spermidine/spermine acetyltransferase (SSAT) in a dose-related manner.

EXAMPLE XXI

Tricyclic and other Heterocyclic Compounds Can Inhibit Polyamine Transport

Employing the polyamine transport assay described in Example XX, several heterocyclic ring compounds were tested for their activity as inhibitors of transport. The unexpected discovery was made that that several compounds strongly resembling tricyclic antidepressants and antipsychotic agents inhibited polyamine transport. Of the compounds shown in FIG. 25 compounds 161, 162 and 165 inhibited the PAT assay in both A172 and MDA cell lines. Compound 165 acted as a non-competitive inhibitor of PAT with a $K_i$ of 41 nM (for A172 cells) and 500 nM (for MDA cells).

Figure 25:
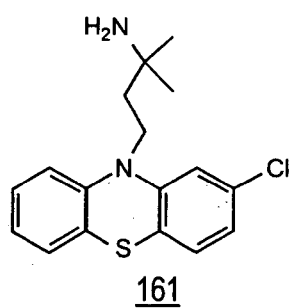
FIG. 25 shows a group of chemical structures (161–165) including three known psychoactive compounds trifluoperazine 163, thorazine 164 and imipramine 165. Compounds 161, 162 and 165 inhibited polyamine transport.
Figure 25:
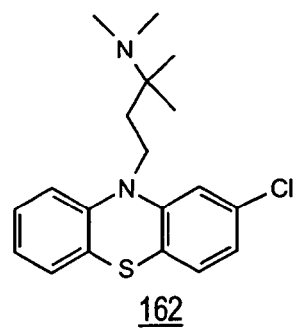
Figure 25:
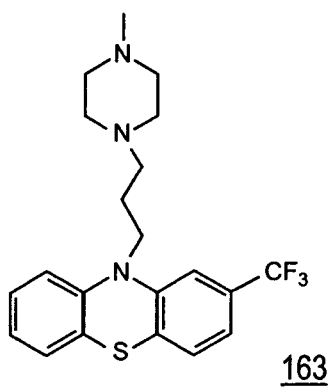
Figure 25:
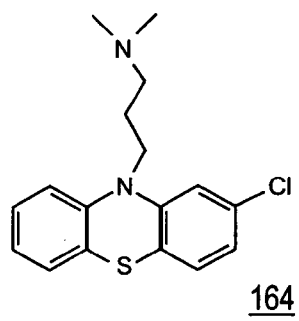
Figure 25:
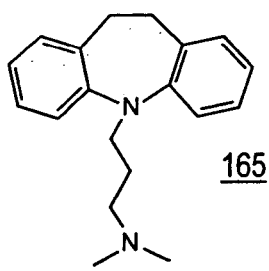
Figure 25:
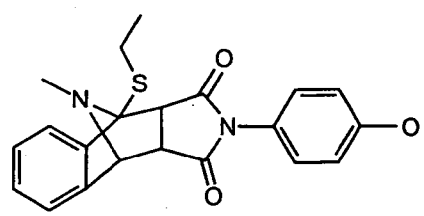

These compounds resembled compounds 163–164 in FIG. 25 which are known antipsychotic and antidepressant drugs. These observations indicate that that compounds of this type modulate polyamine uptake.

EXAMPLE XXII

Figure 23:
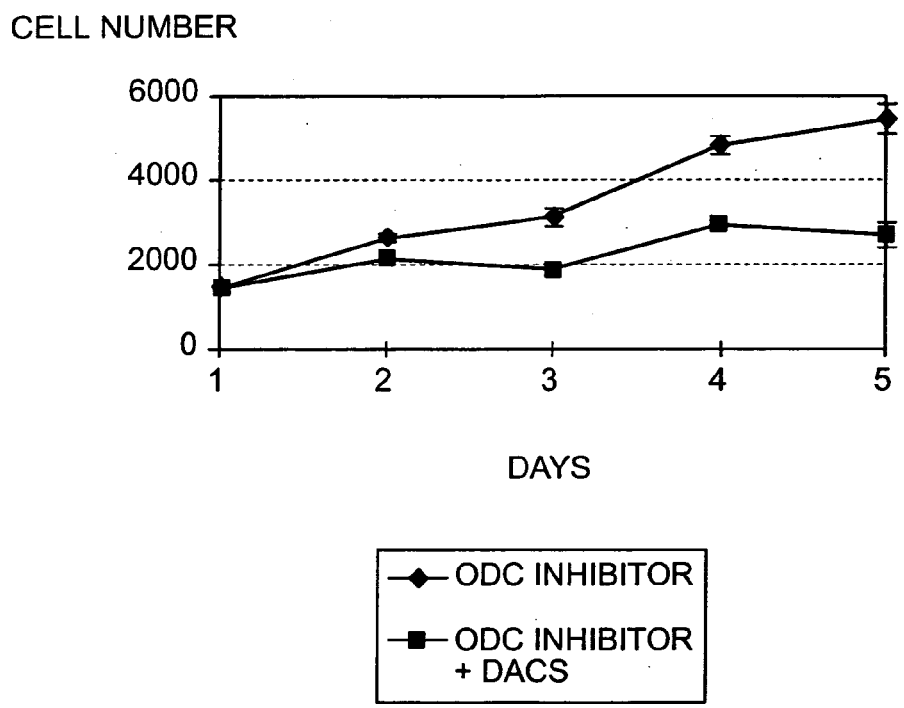
FIG. 23 is graph showing inhibition of cell growth in the presence of 1 µM spermidine.

Effect of Linker Length or "Headless" Status on Growth Inhibition by Polyamine Analogues Compounds were tested for their ability to inhibit cell growth in the presence of 1 μM spermidine and 230 μM ODC inhibitor for the MDA-MB-231 cells or 1 mM ODC inhibitor for the PC3 cells. Cells were plated and drugs were added as described in Example XIX. "Headless" linkers with carbons of 2 or 3 chain length were ineffective on the MDA-MB-231 breast carcinoma but inhibited growth in the PC3 prostatic carcinoma cells as shown in FIGS. 23 and 24.

EXAMPLE XXIII

Evaluation of MDS as a Fluorescent Probe in a PAT Assay

The goal of this experiment was to show that MDS competes with $^3$H-spermidine in a transport assay.

Figure 27:
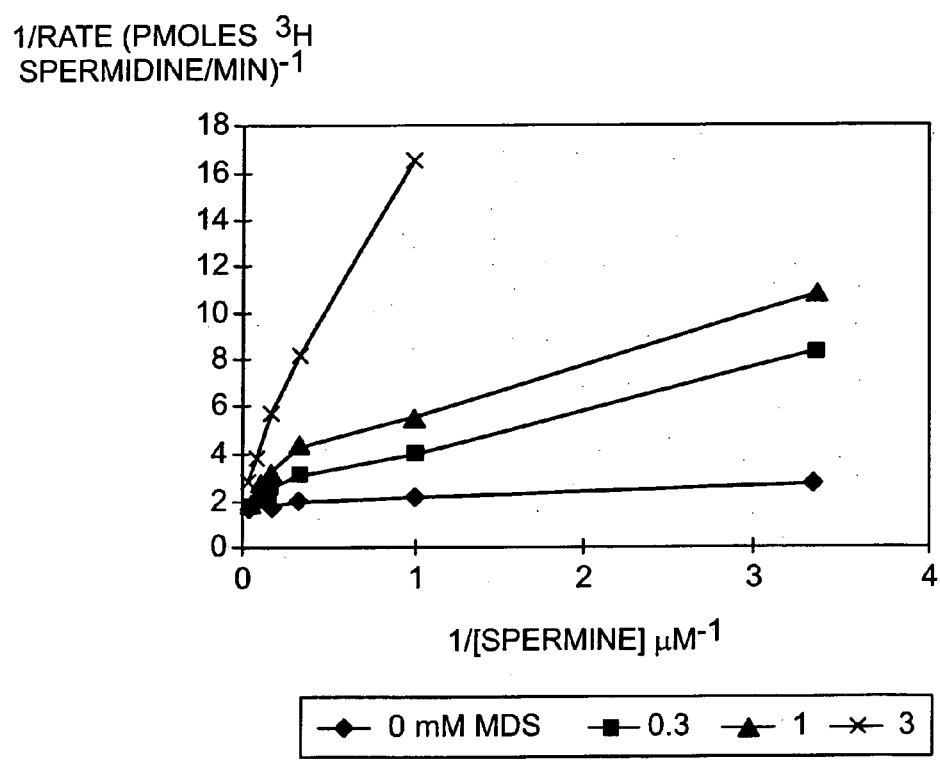
FIG. 27 is a graph showing a comparison of the kinetics of uptake of $N^1$-monodansyl spermine (MDS) with the uptake of radiolabeled spermidine. MDS concentrations were as follows: ♦ 0 ▲ 1 µM ■ 0.3 µM ✱3 µM
Figure 28:
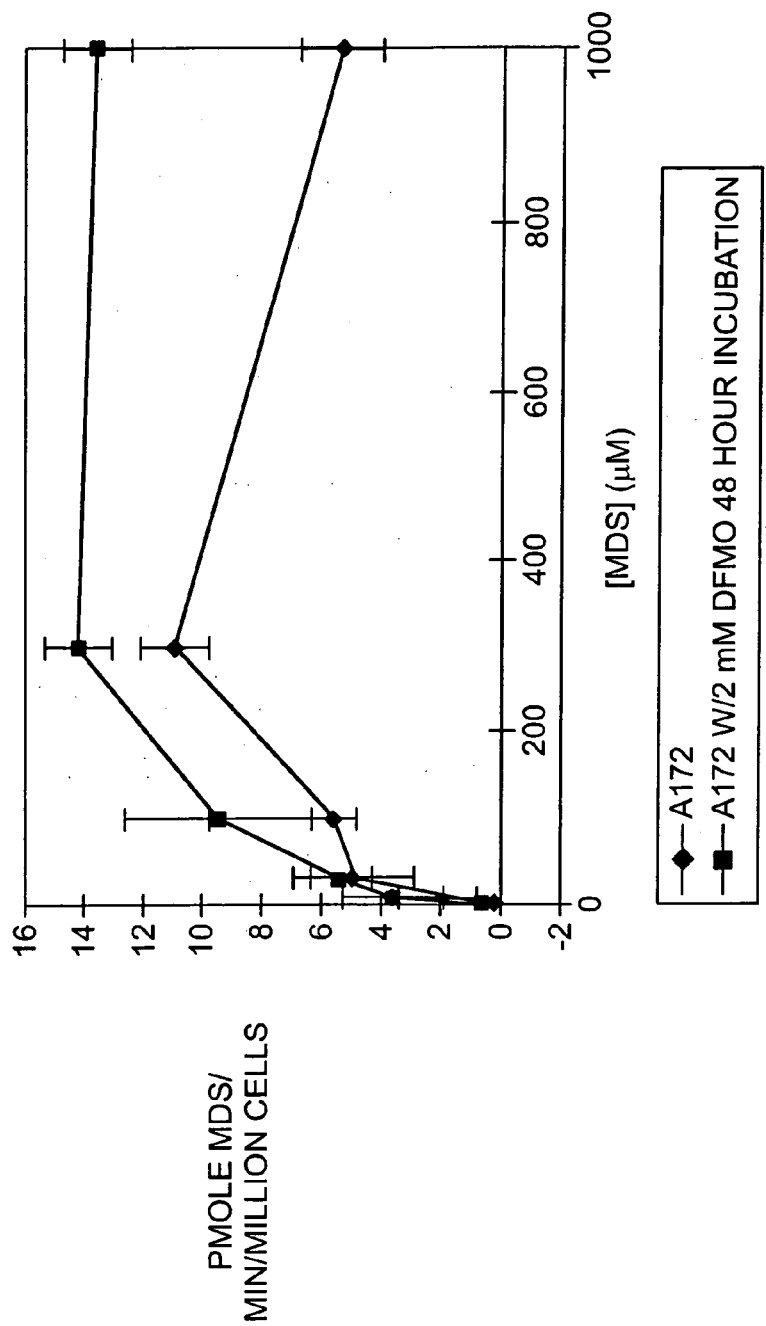
FIG. 28 is a graph showing detection of MDS in the absence of DFMO by fluorescence in A172 glioblastoma cells.
Figure 29:
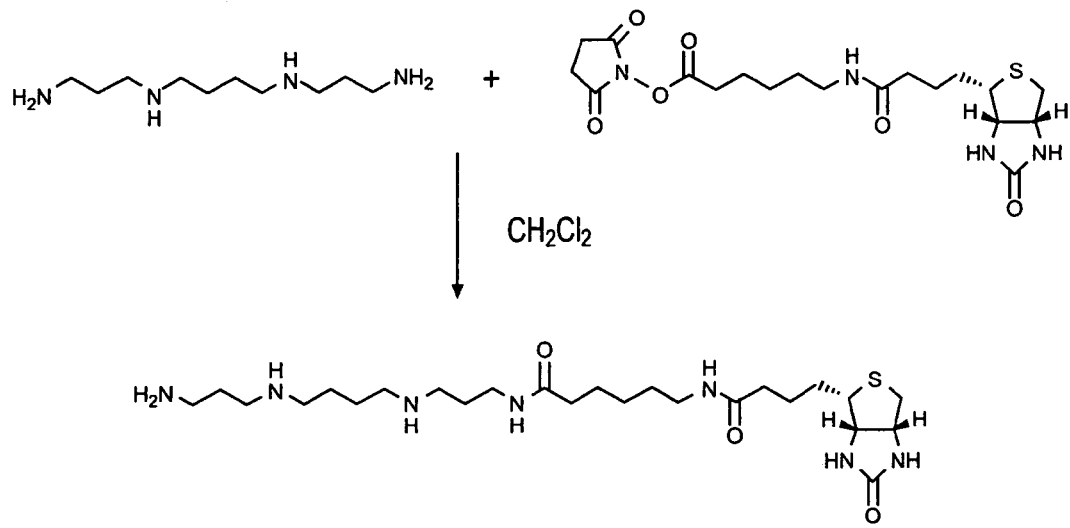
FIGS. 29 and 30 describe the synthesis of a biotin modified polyamines $N^1$-[($N^6$-(biotinyl)-6-aminocaproyl)] spermine and $N^1$-(biotinyl)spermine.
Figure 30:
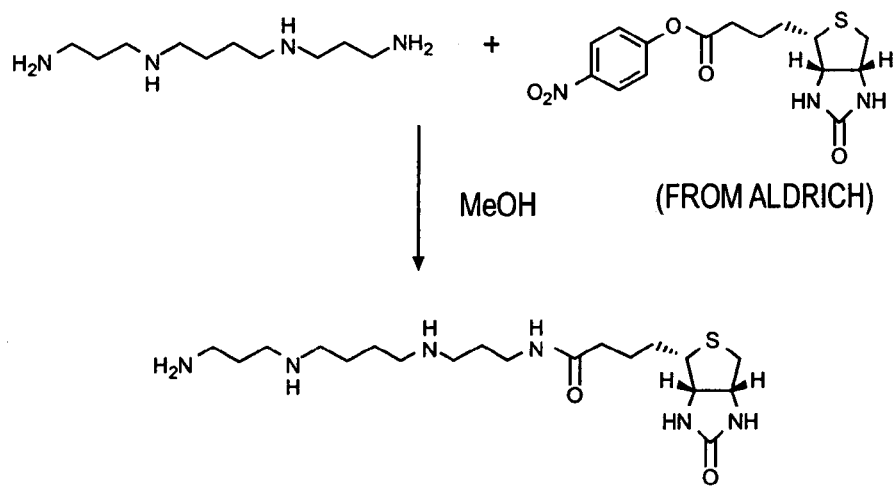
Figure 31:
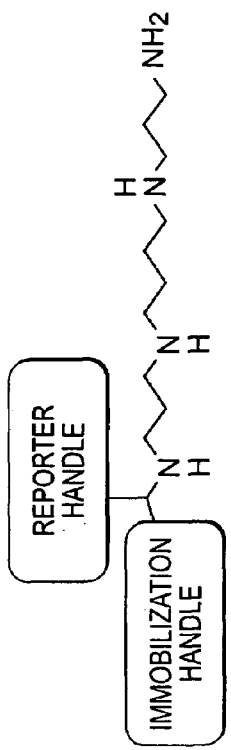
FIG. 31 is a schematic illustration showing the possible sites for modifying a polyamine to create an "immobilization handle" and a "reporter handle" combination.
Figure 31:
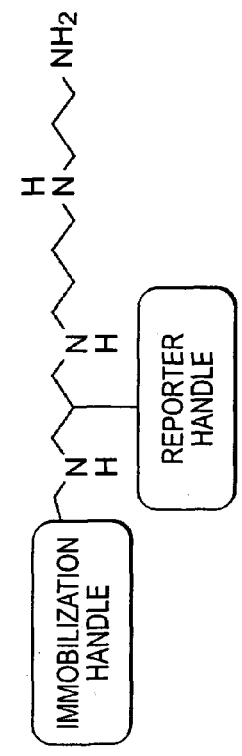
Figure 31:
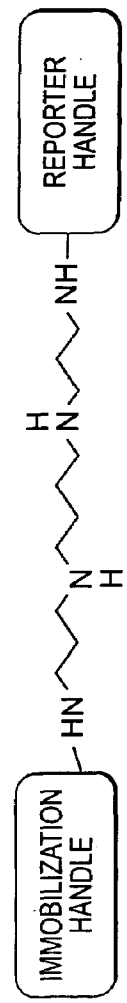

Using the general radiometric PAT assay and A172 cells as described above, MDS was found to competitively displace $^3$H-spermidine in the transport assay (FIGS. 27 and 28).

EXAMPLE XXIV

Fluorescent Microscopic Analysis of Monodansylspermine Uptake

Cells were plated in a sterile chambered slide and grown for 15–48 hours to assure adherence of cells to the slide. The medium was removed and replaced with fresh medium containing 1 μM MDS for a 10 minute incubation period at 37° C. The medium was then removed and the cells washed 3 times with phosphate buffered saline. Glycerol (50% v/v) in a volume of 50 μl was added to the chamber, and the slide was removed and covered with a cover slip.

Using a fluorescence microscope with filters set for excitation at 340 nm and emission at 530 nm, the slide was observed under normal light and with fluorescence. Uptake of the dansylated spermine was observed microscopically and recorded on photograph.

Although a photomicrograph is not included here, cultured cells incubated with MDS took up the labeled material as indicated by the fluorescence which was visualized microscopically. Nucleoli, which contain large amounts of RNA to which the probe could bind, showed particularly strong staining. As expected, the probe was seen lining the membranous structures.

EXAMPLE XXV

Enzymatic Detection of $N^1$-dansylspermine

Polylysine plates were prepared by addition of 200 μl of polylysine (5 μg/ml) in 10 mM Tris-HCl buffer, pH 8.5, containing 10 mM NaCl and 10 mM NaN$_3$ The plates were incubated for 20 min at 37° C. when the wells were washed 3× with 200 μl water. The plates were then treated with μl of 2.5% glutaraldehyde in 50 mM borate buffer pH 10.0 for 1 hr at 25° C., when the wells were washed with 200 μl of 50 mM borate buffer pH 10.0 twice and once with water. Various concentrations of either N 1-dansylspermine or DACS were added to the wells ranging between 0.1 and 10 pmoles/well and incubated for 1 hr at room temperature. The plates were then washed with twice with 200 μl or PBS. The wells were then treated with 200 μl of a 0.3% NH$_4$OH in PBS and was incubated for 1 hr at room temperature when it was washed twice with 200 μl of PBS-0.5% Tween (PBST). The wells were then treated with 200 μl of 0.5% NaBH$_4$ in PBS for 10 minutes when they were washed twice with 200 μl PBST. The wells were then blocked with 200 μl 1% BSA for 1 hour when they were washed once with PBST. Dansyl anti-body (Molecular Probes, Eugene, Oreg.) was added at a 1/200 dilution to each well in 100 μl PBST and incubated overnight at 4° C. when it was washed four times with PBST. To each well was now added 100 μl of anti-HRP antibody at a 1/5000 dilution and incubated for 2 hours at 4° C. when each well was washed four times with PBST. Enzyme activity was determined using either 100 μl of NBT or OPD (5 mg OPD/10 ml of 0.1 M citrate buffer, pH 5.0) and an incubation period of 10 minutes at room temperature. The color was measured at 630 nm in a plate reader.

Figure 32:
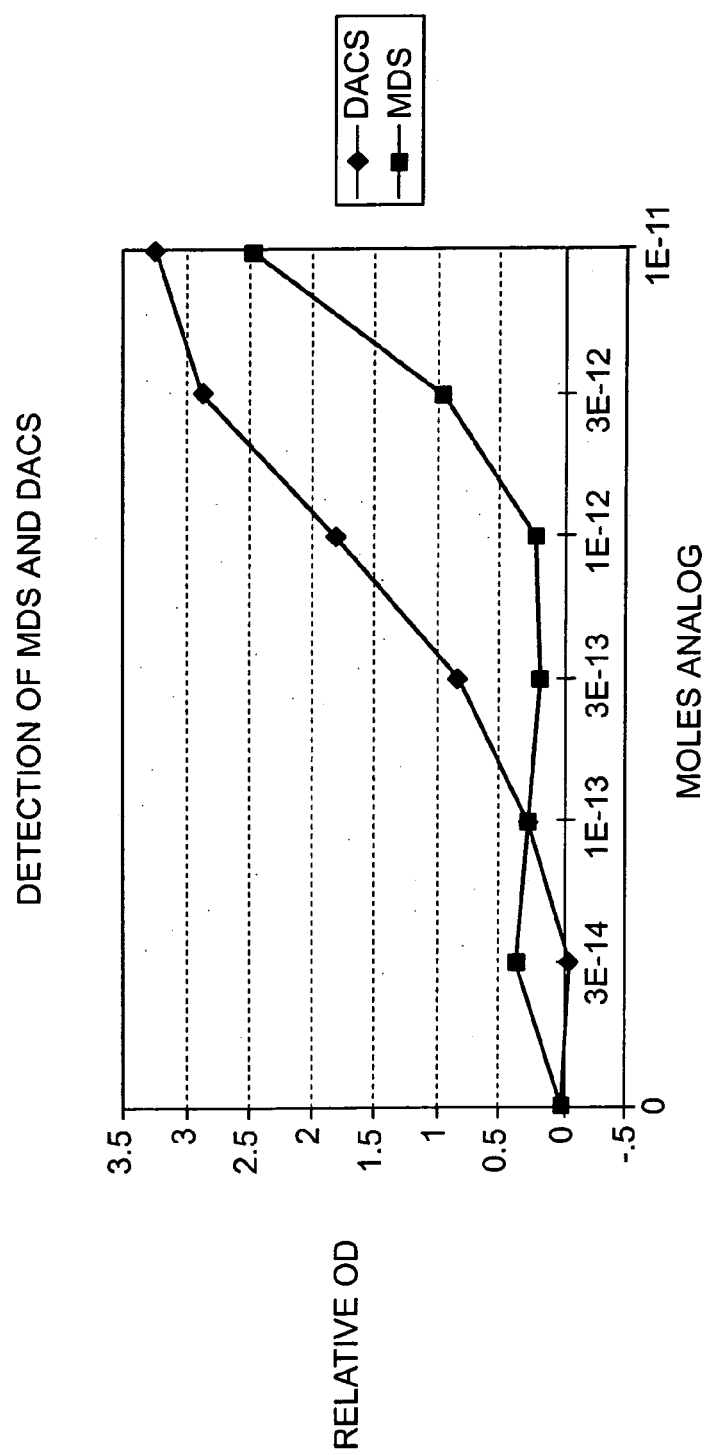
FIG. 32 is a graph showing the detection of N1-dansyl-spermine and DACS using the enzymatic detection system
Figure 33:
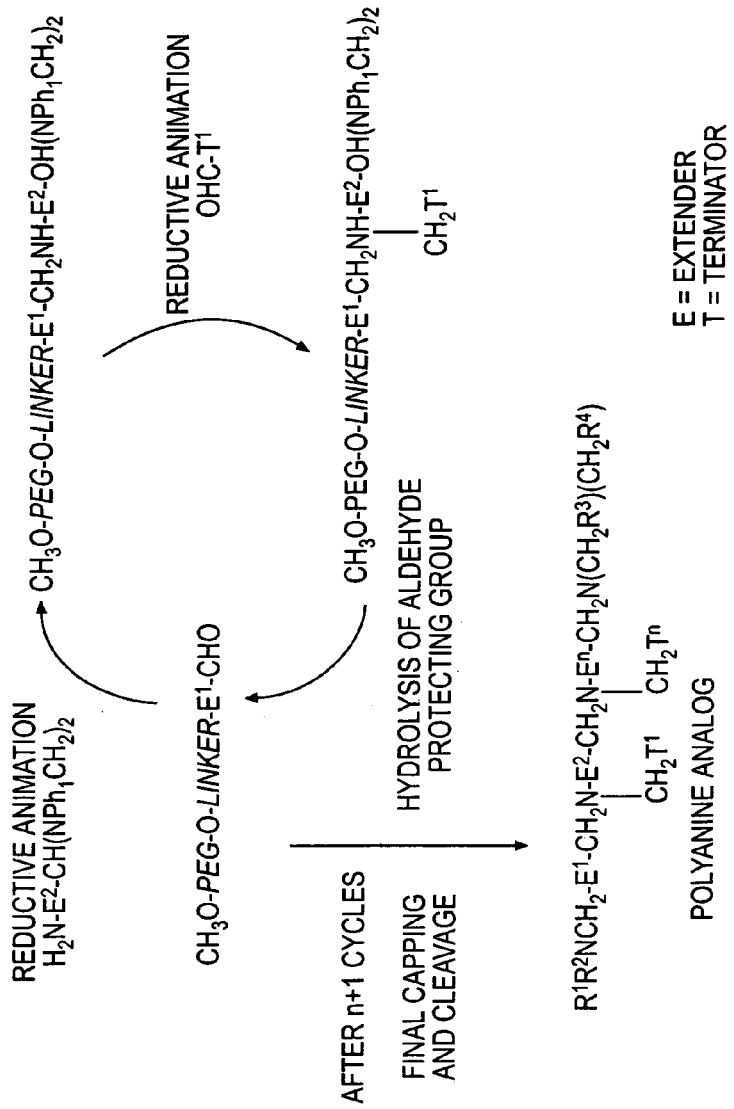
FIG. 33 is a general scheme that brings together the three major components of the present compositions in a synthetic cycle for generating polyamine derivatives.
Figure 34:
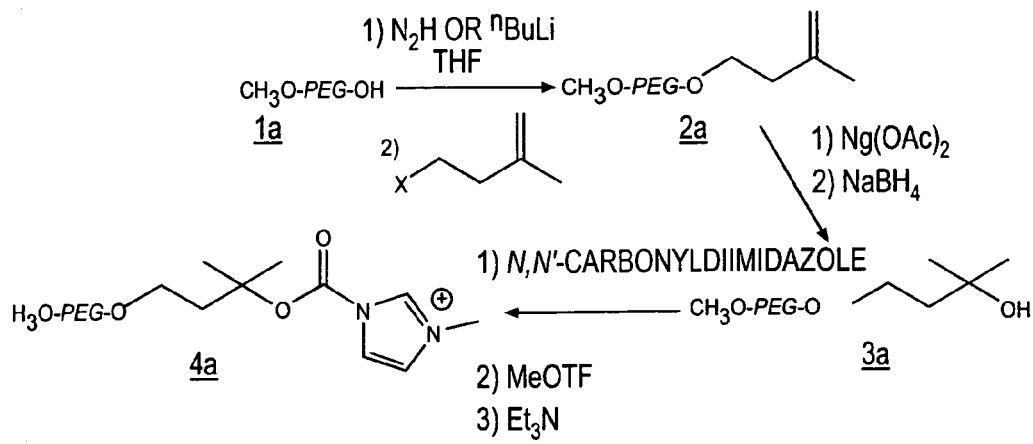
FIG. 34 outlines synthesis of an activated tert-alkoxycarbonyl MeO-PEG polymer which is reacted with a free amino/protected aldehyde extender synthon.
Figure 35:
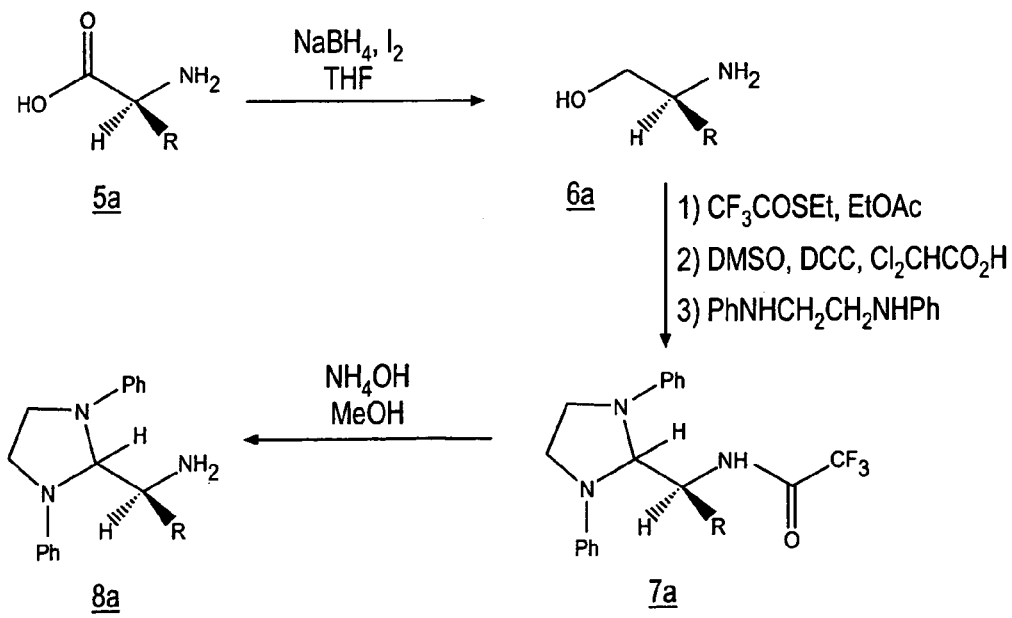
FIG. 35 shows the production of these extenders from either commercially available amino alcohols or the chiral amino acid precursor pool.

This method is an alternate embodiment of the of the PAT assay using indirect detection to enhance the signal and lower the detection limits. This method allows for the detection of extremely low concentrations of probe. The results, shown in FIG. 32, indicated that DACS levels as low as 0.1 pmoles could be detected.

EXAMPLE XXVI

Modifications of Polyamine Analogues

Figure 38:
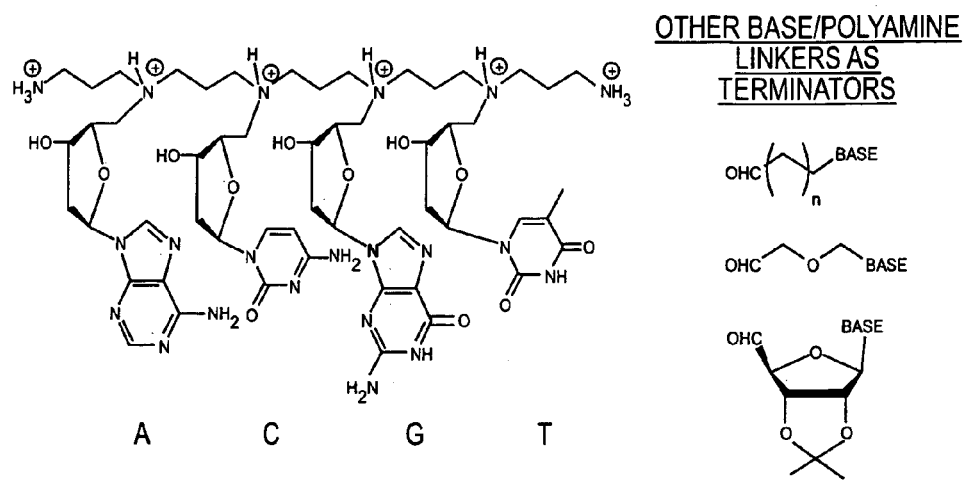
FIG. 38 shows "modifications" of polyamine analogues as they are extended with aldehydic nucleoside terminators. Each amino group can be dressed individually and specifically with any of the four ribonucleosides or 2'-deoxyribonucleosides.

By "modifying" the extending polyamine analogues with aldehydic nucleoside terminators, it is possible to produce sequence specific hybrid oligomers. Each amino group is "modified" individually and specifically with any of the four ribonucleosides (or 2'-deoxyribonucleosides) as shown in FIG. 38.

This technology provides an approach for solving the problem of triple-helix forming antisense oligonucleotides (Chan, P—P. et al., *J. Mol. Med.* 75: 267–282 (1997) by combining the transportability of polyamines into cells with structural features of nucleotide sequence specificity. The transport overcomes the limitations of bioavailability while also enhancing the bio-stability of such an oligomer.

EXAMPLE XXVII

Figure 36:
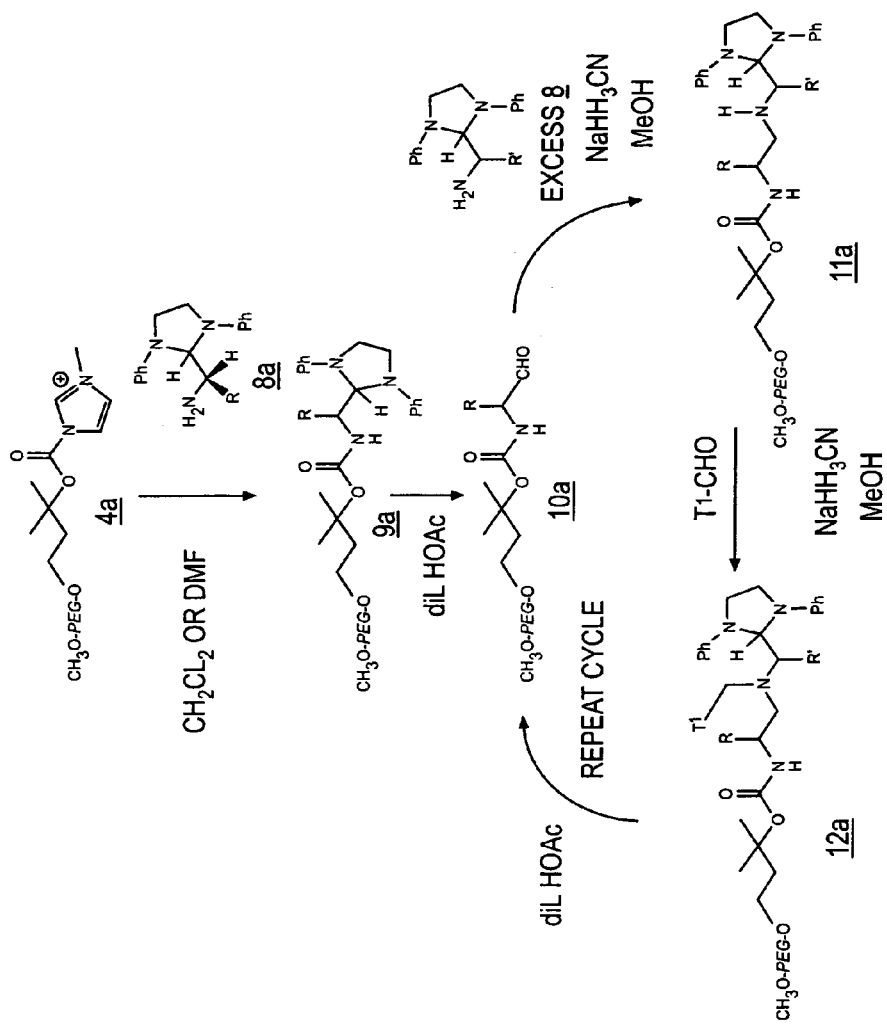
FIG. 36 shows the next step in the synthetic cycle: reductive amination with $NaBH_3CN$ is used to initially extend the backbone followed by an additional reductive amination step with an aldehyde to terminate the secondary amine produced.
Figure 37:
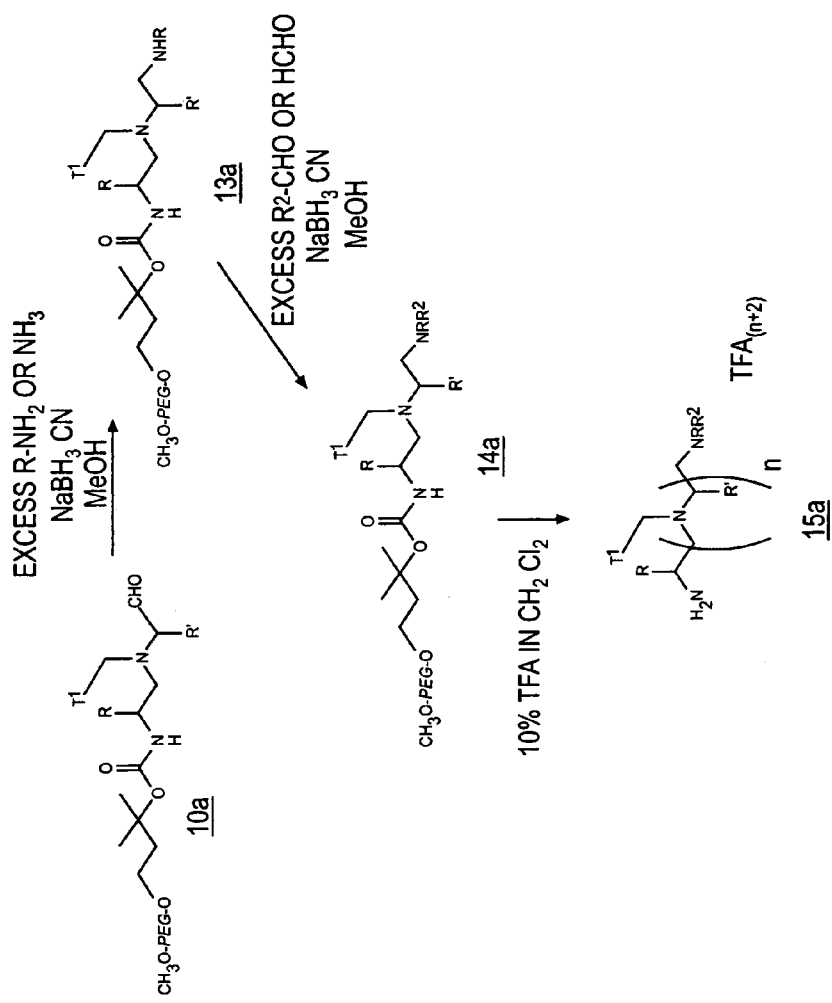
FIG. 37 shows the final steps, including the final capping and the acid-mediated cleavage of the product from the polymeric support as the trifluoroacetate salt of the desired analogue.
Figure 39:
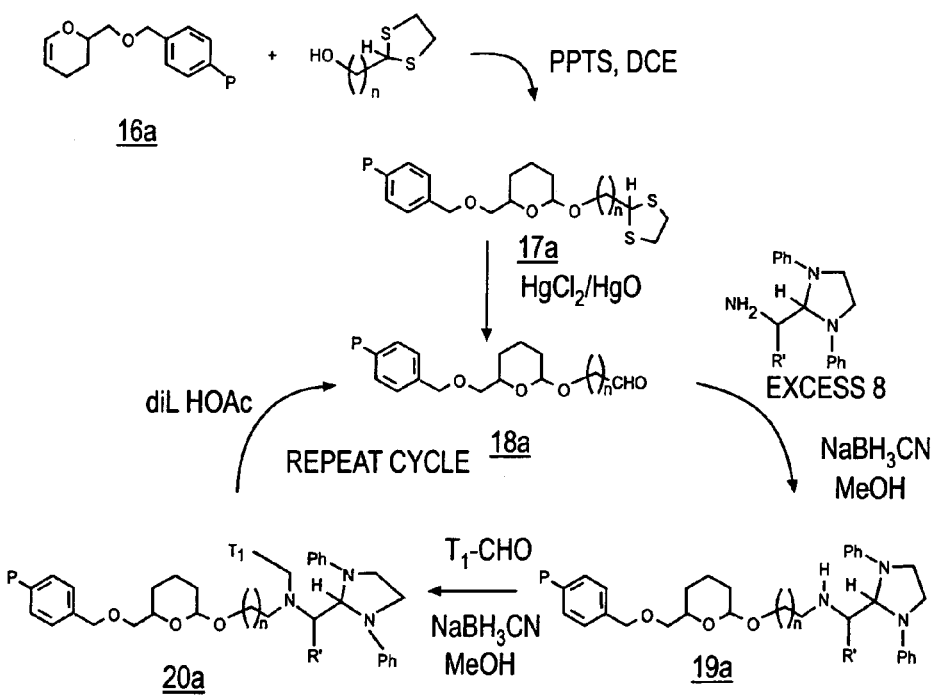
FIG. 39 shows an example of a solid support with alternative linking groups used for solid phase synthesis of polyamine libraries. 3,4-dihydro-2H-pyran-2-ylmethoxymethyl polystyrene is shown.
Figure 40:
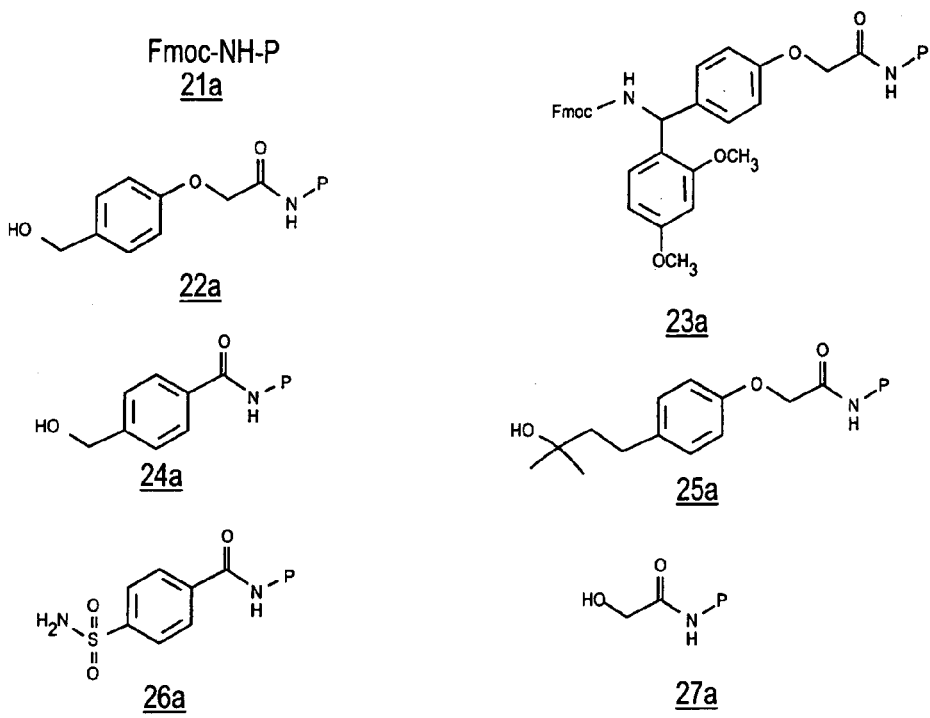
FIG. 40 shows various linkers used in a multipin method of dimensionally stable polypropylene/polyethylene pins to which a graft polymer is covalently linked. The Rink amide linker is shown as structure 23a coupled to the pin.
Figure 41:
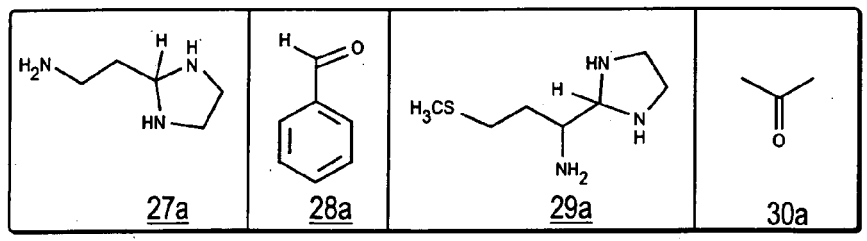
FIG. 41 shows a compound that is synthesized using a solid support and the synthetic approach described for FIGS. 4 and 5. Compound 31a is synthesized using the blocked 3-aminopropanal 27a as the first extender, benzaldehyde 28a as the first terminator, the blocked methioninal 29a as the second extender and acetone as the final terminator.
Figure 41:
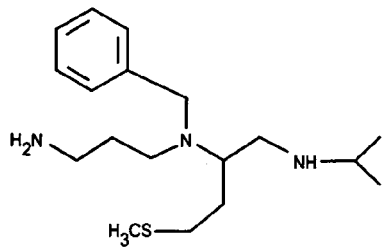

Using the approach outlined in FIGS. 36 and 37, compound 31a (FIG. 39) is synthesized using the blocked 3-aminopropanal 27a, benzaldehyde 28a as the first terminator, the blocked methioninal 29a as an extender and acetone as the final terminator.

EXAMPLE XXVIII

A library of compounds is synthesized by using the appropriate blocked aminoaldehydes, aldehydes or ketones. The general structures are shown below.

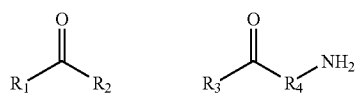

In the case of aldehydes and aminoaldehydes, $R_1$ and $R_3$ are both hydrogen. In the case of ketones and aminoketones $R_1$=$R_3$=H or —$(CH_2)_n CH_3$ where n=0 to 6. The ketofunction can also be a part of a ring structure. $R_2$ and $R_4$ can be aliphatic, alicyclic, aromatic and heterocyclic. Examples of compounds that could be contain aldehyde, ketone, amino-aldehyde or amino-ketone functions are dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, piperidine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 2-[1,2-dihydro-2H-1,410 benzodioxepinyl]thiazole, benzene, naphthalene, phenanthrene, anthracene, pyrene, alkanes containing 2 to 10 carbons, alkenes containing 1 to 3 unsaturations and 3 to 10 carbons, alkynes containing 1 to 3 unsaturations and 3 to 10 carbons, branched alkanes, alkenes, alkynes containing 3 to 10 carbon atoms. Many aldehydes, ketones, aminoaldehydes and aminoketones containing one or more of the functional groups listed above, are commercially available. A number of aminoalcohols, precursors for aminoaldehydes are listed in Table 2, below.

TABLE 2

Aminoalcohol Extenders

Alinol
L-methioninol
R,S-2-amino-1-butanol
3-amino-1-propanol
5-aminopentanol
R,S-2-amino-2-phenylethanol
6-amino-1-hexanol
2-amino-3-methyl-1-pentanol
2-(2-amino-4-nitroanilino)ethanol
2-aminophenethyl alcohol
2-amino-3-methyl-1-pentanol
(S)-(–)-2-amino-3-phenyl-1-propanol
D,L-1-amino-2-propanol
3-amino-1-propanol
D-mannosamine
2-amino-2-methyl-1-propanol
D-glucosamine
4-aminobutanol
trans-2-aminocyclohexanol
(S)-(+)-2-amino-3-cyclohexyl-1-propanol
DL-2-amino-1-hexanol
1-(1S,2S)(+)2-amino-3-methoxy-1-phenyl-1-propanol
2-amino-4-methyl-1-pentanol
D,L-2-amino-1-pentanol
2-amino-1-phenethylethanol
(R)-(+)-2-amino-3-phenyl-1-propanol
2-(-3aminophenylsulfonyl)ethanol
D,L-2-amino-1-propanol
D-galactosamine

EXAMPLE XXIX

A library of compounds is synthesized by using the appropriate blocked aminoaldehydes, aldehydes or ketones selected from commercially available sources or from synthetic routes known in the art. Aminoaldehydes are synthesized in a variety of ways from various starting materials such as L- and D-amino acids, aminoalcohols, or alcohols or carboxylic acid substituted with $NO_2$ or —CN groups. Aminoaldehydes are synthesized from appropriately blocked aminoalcohols by known procedures (Larack, R., In: *Comprehensive Organic Transformations*, VCH Publishers, Inc., NY, 1989, pp. 604–616). Aminoaldehydes are directly synthesized from appropriately blocked aminocarboxylic acids or blocked aminonitrile (supra at P 616–617).

EXAMPLE XXX

Ki Determinations and Structure Activity Relationships

The polyamine analogues and derivatives of the invention may be evaluated for their ability to inhibit the uptake of spermidine into MDA cells in culture. Joro spider toxin JSTx-3 is available from Calbiochem; 1-Naphthylacetyl-spermine is available from RBI. Deoxyspergualin was a generous gift from Paul Gladstone. $K_i$s were measured for the polyamine analogues in FIG. 44 and the results are shown therein.

Compound 1111, the Joro spider toxin JSTx-3 (Aramaki, Y. et al. Chemical characterization of spider toxin, JSTX and NSTX. Proc. Japan, Acad. 1986, 62, Ser. B, 359–362), and compound 1022, a simplified synthetic analog (Asami, T.; Kagechika, H.; Hashimoto, Y.; Shudo, K.; Miwa, A.; Kawai, N.; Nakajima, T. Acylpolyamines mimic the action of Joro spider toxin (JSTX) on crustacean muscle glutamate receptors. *Biomedical Res* 1989, 10, 185–189) were both were found to be effective polyamine transport inhibitors with $K_i$ values of 190 and 230 nM respectively. An additional natural product, deoxyspergualin (compound named 1085) was also shown to have good affinity to the polyamine uptake system of MDA cells ($K_i$=81 nM). These results showed that these polyamine natural products had equal or better affinities for the polyamine uptake system than any analogs yet reported in the literature.

Simple polyamine amides were equally effective at inhibition of spermidine uptake. Non-functionalized acyl groups were placed at the $N^1$ position of spermine to give compounds 1110, 1107, 1163, 1166, 1212, 1235, and 1244. The best analog in this series was $N^1$-boc-spermine (1163), with a $K_i$ of 83 nM. This molecule has been reported in the chemical literature as a protected polyamine intermediate. It is interesting to note that $N^1$-acetylspermine (1110) has a 3-fold greater affinity for the transport system ($K_i$=162 nM) than spermidine ($K_m$=520 nM). It appears that the presence of a hydrophobic propylacetylamide moiety increases the affinity over the unsubstituted spermidine structure. Insights into the steric environment of this hydrophobic pocket can be seen by comparison of amides 1212 ($K_i$=198 nM) and 1235 ($K_i$=1140 nM). The bulky adamantyl group is tolerated if a methylene spacer is included.

Further increases in affinity for the transport system are obtained by placing an amino group at the end of the linear acyl group. The glycine, β-alanine, δ-aminobutyric and 6-aminohexanoic acid conjugates (1125, 1177, 1150, and 1094, respectively) showed $K_i$s of 87, 71, 42 and 69 nM respectively. The advantage in having an additional amino group at this position can be seen by the direct comparison of the amide 1094 with its deaza counterpart 1107 (Ki values of 69 versus 182 nM).

Given the high affinities of the linear amino-substituted analogs for the transport system, the affinities of α-amino acid/spermine conjugates were examined. A series of α-alkyl substituted amino acids was produced. All tested amino acid derivatives are the L-stereoisomers unless otherwise noted. This series included the α-Ala-Spm, aminoisobutyric-Spm (Aib-Spm), L-Val-Spm, D-Val-Spm, tBu-tylGly-Spm, Ile-Spm, Leu-Spm, cyclohexylalanine-Spm (Cha-Spm), Pro-Spm, and pyroglutamate-Spm (pGlu-Spm) conjugates (1178, 1220, 1157, 1196, 1194, 1228, 1230, 1227, 1159, and 1188, respectively, in FIG. 44). α-Methyl substitution had a negative impact on the affinity (compare Gly-Spm, 1125, with $K_i$; =87 nM to α-Ala-Spm, 1178, with $K_i$=244 nM to Aib-Spm, 1220, with $K_i$=160 nM). Comparison of the L-Val-Spm, 1157, with $K_i$=84 nM to D-Val-Spm, 1196, with $K_i$=48 nM) conjugate showed a stereochemical preference for binding.

Very strong steric effects were suggested by subtle changes in the placement of alkyl groups on the side-chain. Addition of an extra methyl group at the methine center of the Val side-chain reduced the affinity (tButylGly-Spm, 1194, with $K_i$=212 nM). Addition of this extra methyl group at the methyl center of the Val conjugate again reduced the affinity for the transporter (Ile-Spm, 1228, with $K_i$=124 nM). By simply moving this methyl group one position a dramatic improvement in binding was observed (Leu-Spm, 1230, with $K_i$=32 nM). Increased steric bulk on this derivative again reduced the affinity (Cha-Spm, 1227, with $K_i$=241 nM). Formation of a ring by coupling proline with spermine produced a tight binding analog (Pro-Spm, 1159, with $K_i$=38 nM). The requirement for a basic amino group on the amino acid side-chain is dramatically shown by the pGlu-Spm analog, 1188, with $K_i$=10600 nM.

The effects of using functionalized amino acids as conjugates with spermine were examined next. This series includes Asn-Spm, Gln-Spm, Asp-Spm, Glu-Spm, Met-Spm, Ser-Spm, Thr-Spm, Orn-Spm, Lys-Spm, Arg-Spm, and the di-guanidinoLys-Spm conjugates (1131, 1154, 1186, 1171, 1164, 1187, 1207, 1224, 1202, 1250, 1260, and 1304, respectively in FIG. 44). The asparagine ($K_i$=32 nM) and glutamine ($K_i$=47 nM) spermine conjugates, 1131 and 1154, respectively, were better inhibitors in comparison to their free acid counterparts, the aspartic ($K_i$=167 nM) and glutamine ($K_i$=76 nM) conjugates, 1186 and 1171, respectively. The Met-Spm ($K_i$=34 nM), Ser-Spm ($K_i$=45 nM), Orn-Spm ($K_i$=47 nM), Lys-Spm ($K_i$=37 nM) and Arg-Spm ($K_i$=99 rNM) conjugates, 1164, 1187 and 1224, 1202, and 1260, respectively, all had $K_i$ values below 100 nM.

Amino acids containing aromatic groups were also examined. This series included the L-Trp-Spm, D-Trp-Spm, Phe-Spm, Tyr-Spm, and $N^2,N^6$-dibenzyl-Lys-Spm conjugates, 1095, 1309, 1148, 1173, and 1310, respectively in FIG. 44. The D-Trp-Spm ($K_i$=26 nM), Tyr-Spm ($K_i$=77 nM) and $N^2,N^6$-dibenzyl-Lys-Spm ($K_i$=41 nM) conjugates, 1309, 1173, and 1310, respectively, were the most effective in this series and each had $K_i$ values below 100 nM.

EXAMPLE XXXI $IC_{50}$ against MDA cells with DFMO and spermidine

A cellular assay was developed to highlight the ability of the amino acid/spermine amides to work in concert with the ODC inhibitor DFMO in the presence of added 1 µM spermidine. In this assay, no growth inhibition is observed with DFMO alone because the cells are able to utilize the spermidine added to the culture media even when polyamine biosynthesis is inhibited. Thus inhibition of uptake of the exogenously added spermidine by any of the tested analogues or derivatives results in observable growth inhibition due to polyamine depletion.

Analysis of the data from this assay in FIG. 44 shows that several of the conjugates are able to inhibit the growth of MDA cancer cells in combination with 230 µM DFMO even in the presence of 1 µM spermidine. The synthetic spider toxin (1022) with a $K_i$ of 230 nM was able to inhibit the growth of MDA cells with an $IC_{50}$ of 8.3 µM. Among the simple spermine amides the 2-(adamantyl)acetyl-spermine conjugate, 1212, with $K_i$=26 nM, showed an $IC_{50}$ of 9 µM against these cells. The 6-aminocaproic acid-spermine conjugate, 1094, with $K_i$=69 nM showed an $IC_{50}$ of 32 nM. Among the alkyl substituted amino acid conjugates the following had effective $IC_{50}$ values: Aib-Spm, 1220, with $K_i$=160 nM, $IC_{50}$=8 µM, L-Val-Spm, 1157, with $K_i$=84 nM, $IC_{50}$=16 µM, D-Val-Spm, 1196, with $K_i$=48 nM, $IC_{50}$=9 µM, $^t$ButylGly-Spm, 1194, with $K_i$=212 nM, $IC_{50}$=11 µM, Ile-Spm, 1228, with $K_i$=124 nM, $IC_{50}$=9 µM; and Cha-Spm, 1227, with $K_i$=241 nM, $IC_{50}$=82 M.

The conjugates with functionalized aminoacids that gave low $IC_{50}$ values in the presence of DFMO are the following: Ser-Spm, 1187, with $K_i$=45 nM, $IC_{50}$=26 µM, Thr-Spm, 1207, with $K_i$=130 nM, $IC_{50=6}$ µM, Orn-Spm, 1224, with $K_i$=47 nM, $IC_{50}$=3 µM; and Lys-Spm, 1159, with $K_i$=37 nM, $IC_{50}$=5 µM. The aromatic group containing aminoacid-spermine conjugates that gave $IC_{50}$ values below 30 µM were L-Trp-Spm, 1095, with $K_i$=162 nM, $IC_{50}$=15 µM; and $N^2,N^6$-dibenzyl-Lys-Spm, 1310, with $K_i$=41 nM, $IC_{50}$=8 µM Overall, there appears to be no correlation between an analogue's ability to inhibit transport of spermidine and its ability to inhibit cell growth in the presence of DFMO. Some analogues with $K_i$ values below 100 nM failed to give effective $IC_{50}$ values with DFMO. Examples of this type of analogue include Gly-Spm, 1125; β-Ala-Spm, 1177; Leu-Spm, 1230; Gln-Spm, 1154; Glu-Spm, 1171; and Met-Spm, 1164 conjugates. A possible explanation for this observation is the ability of these analogs to act as substrates for the polyamine transporter thereby supplying the cells with their necessary polyamines. Upon further testing, conjugates Gly-Spm, 6-aminocaproic acid-Spm, and Pro-Spm, 1125, 1094, and 1159, respectively, were able to rescue cells from growth inhibitory effects of DFMO, suggesting that they are substrates. Conjugates L-Val-Spm, Orn-Spm, and Lys-Spm, 1157, 1224, and 1202, respectively, were not able to rescue from the effects of DFMO, suggesting they are not substrates for the polyamine transporter.

EXAMPLE XXXII

Nuclear Magnetic Resonance Data for Selected Polyamine Analogues and Derivatives $N^1$-Spermine 2-(1-adamantyl)acetamide (1212)-$^1$H NMR ($D_2O$, δ): 2.98 (t, 2H), 2.82 (m, 10H), 1.80 (m, 2H), 1.76 (s, 3H), 1.63 (m, 6H), 1.48 (m, 4H), 1.36 (m, 4H), 1.22 (s, 6H).

$N^1$-spermine 1-adamantylamide (1235)-$^1$H NMR ($D_2O$, δ): 3.24 (t, 2H), 3.00 (m, 10H), 1.95(m, 4H), 1.74 (m, 10H), 1.62 (m, 9H).

$N^1$-Spermine 2-(2-indolyl)acetamide (1244)-$^1$H NMR ($D_2O$, δ): 7.43 (d, 1H), 7.38 (d, 1H), 7.17 (s, 1H), 7.11 (t, 1H), 7.02 (t, 1H), 3.56 (s, 2H), 3.08 (t, 2H), 1.93 (m, 4H), 2.84 (t, 2H), 2.61 (m, 4H), 1.94 (m, 2H), 1.62 (m, 2H), 1.48 (m, 4H). 13CNMR (D2O, ppm): 178.3, 138.7, 129.0, 127.6, 124.6, 122.1, 120.8, 114.6, 110.1, 49.4, 49.2, 47.3, 47.0, 39.1, 38.4, 34.9, 28.0, 26.3, 25.2, 25.0.

$N^1$-Spermine-glycinyl amide (1125)-$^1$H NMR ($D_2O$, δ): 3.91 (s, 2H), 3.43 (t, 2H), 3.20 (m, 10H), 2.21 (m, 2H), 2.18 (m, 2H), 1.87 (m, 4H). $^{13}$C NMR ($D_2O$, ppm): 175.4, 47.8, 47.7, 46.0, 45.3, 41.2, 37.4, 37.1, 26.2, 24.5, 23.6 (2C).

$N^1$-Spermine-β-alanyl amide (1177)-$^1$H NMR ($D_2O$, δ): 3.29 (m, 4H), 3.10 (m, 10H), 2.68 (t, 2H), 2.09 (m, 2H), 1.90 (m, 2H), 1.78 (m, 4H). $^{13}$C NMR ($D_2O$, ppm): 175.0, 49.6, 49.5, 47.8, 47.1, 39.2, 38.8, 38.3, 34.5, 28.1, 26.3, 25.4 (2C).

N$^1$-Spermine-L-alanyl amide (1178)-$^1$H NMR(D$_2$O, δ): 4.08 (quart, 1H), 3.19 (t, 2H), 3.08 (m, 10H), 2.13 (m, 2H), 1.96 (m, 2H), 1.79 (m, 4H), 1.52 (d, 3H). $^{13}$C NMR (D$_2$O, ppm): 173.6, 51.7, 49.6, 49.5, 47.8, 47.2, 39.2, 40.0, 28.1, 26.4, 25.4 (2C), 19.2.

N$^1$-Spermine-α-aminoisobutyryl amide (1220)-$^1$H NMR (D$_2$O, δ): 3.37 (t, 2H), 3.14 (m, 10H), 2.13 (m, 2H), 1.96 (m, 2H), 1.82 (m, 4H), 1.64 (s, 6H). $^{13}$C NMR (D$_2$O, ppm): 173.5, 57.6, 47.7, 47.6, 45.9, 45.3, 37.3 (2C), 26.2, 24.4, 24.0 (2C), 23.5 (2C).

N$^1$-Spermine-L-valinyl amide (1157)-$^1$H NMR (D$_2$O, δ): 3.36 (d, 1H), 3.18 (m, 2H), 3.11 (m, 10H), 2.02 (m, 3H), 1.82 (m, 2H), 1.54 (m, 4H), 0.90 (d, 6H). $^{13}$C NMR (D$_2$O, ppm): 172.1, 61.3, 49.6, 49.5, 47.9, 47.2, 39.2, 39.1, 32.4, 28.1, 26.4, 25.4 (2C), 20.3, 19.7. MS (ESI+): 302 (M+H).

N$^1$-Spermine-D-valinyl amide (1196)-$^1$H NMR and $^{13}$C NMR were the same as above.

N$^1$-Spermine-L-$^t$butylglycinyl amide (1194)-$^1$H NMR (D$_2$O, δ): 3.50 (s, 1H), 3.15 (t, 2H), 2.91 (m, 12H), 1.90 (m, 2H), 1.74 (m, 2H). 1.58 (m, 4H), 0.85 (s, 9H). $^{13}$C NMR (D$_2$O, ppm): 171.2, 67.9, 64.4, 49.6, 49.5, 47.8, 47.1, 39.2, 39.0, 35.3, 28.2, 28.0, 26.3.25.3.

N$^1$-Spermine-L-isoleucinyl amide (1228)-$^1$H NMR (D$_2$O, δ): 3.84 (d, 1H), 3.37 (t, 2H), 3.11 (m, 10H), 2.09 (m, 2H), 1.96 (m, 3H), 1.78 (m, 4H), 1.50 (m, 1H), 1.26 (m, 1H), 0.99 (d, 3H), 0.93 (t, 3H). $^{13}$C NMR (D$_2$O, ppm): 172.1, 60.4, 49.5, 47.8, 47.1, 39.2, 39.0, 38.8, 28.0, 26.8, 26.3, 25.4 (2C), 25.2, 16.7, 13.1.

N$^1$-Spermine-L-leucinyl amide (1230)-$^1$H NMR (D$_2$O, δ): 3.98 (t, 1H), 3.33 (m, 2H), 3.09 (m, 10H), 2.09 (m, 2H), 1.91 (m, 2H), 1.74 (m, 7H), 0.93 (dd, 6H). $^{13}$C NMR (D$_2$O,ppm): 173.2, 54.6, 49.6, 47.8, 47.2, 42.4, 39.2, 39.0, 28.0, 27.9, 26.5, 26.3, 25.4 (2C), 24.4, 23.8.

N$^1$-Spermine-L-cyclohexanealanyl amide (1227)-$^1$H NMR (D$_2$ δ): 4.03 (t, 1H), 3.36 (m, 2H), 3.12 (m, 10H), 2.11 (m, 2H), 1.95 (m, 2H), 1.77 (m, 12H), 1.11 (m, 5H). $^{13}$C NMR (D$_2$O,ppm): 173.4, 54.0, 49.6, 49.5, 47.8, 47.1, 41.0, 39.2, 39.0, 35.7, 35.2, 34.6, 28.3, 28.2, 28.0, 26.3, 25.4.

N$^1$-Spermine-L-prolinyl amide (1159)-$^1$H NMR (D$_2$O, δ): 4.45 (t, 1H), 3.53 (m, 2H), 3.50 (t, 2H), 3.18 (m, 14H), 2.19 (m, 4H), 2.01 (m, 2H), 1.86 (m, 2H). $^{13}$C NMR (D$_2$O, ppm): 172.9, 63.2, 57.1, 50.4, 50.3, 49.8, 48.6, 47.9, 40.1, 40.0, 33.1, 28.8, 27.3, 27.2, 26.3.

N$^1$-Spermine-L-asparaginyl amide (1131)-$^1$H NMR (D$_2$O, δ): 4.33 (m, 1H), 3.30 (m, 2H), 3.10 (m, 12H), 2.09 (m, 2H), 1.92 (m, 2H), 1.78 (m, 4H). $^{13}$C NMR (D$_2$O, ppm): 173.8, 173.7, 52.3, 52.1, 49.6, 47.7, 47.1, 39.1, 38.7, 37.4, 37.0, 28.1, 26.3, 25.4.

N$^1$-Spermine-L-glutaminyl amide (1154)-$^1$H NMR (D$_2$O, δ): 4.05 (m, 1H), 3.34 (t, 2H), 3.13 (m, 10H), 2.48 (m, 2H), 2.18 (m, 4H), 1.93 (m, 2H), 1.79 (m, 4H). $^{13}$C NMR (D$_2$O, ppm): 176.1, 170.1, 57.7, 53.2, 47.7, 45.8, 45.2, 37.3, 36.8, 29.9, 26.3, 26.0, 24.4, 23.5 (2C).

N$^1$-Spermine-L-methionyl amide (1164)-$^1$H NMR (D$_2$O, δ):4.10(t,1H), 3.34 (m 2H), 3.10 (m, 12H), 2.60 (t, 2H), 2.18 (m, 2H), 2.11 (s, 3H), 2.07 (m, 2H), 1.78 (m, 4H). $^{13}$C NMR (D$_2$O, ppm): 172.1, 55.0, 49.6, 49.5, 47.8, 47.1, 39.1, 32.4, 30.8, 28.0, 26.3, 25.4 (2C), 16.6. MS (ESI$^+$): 334 (M+H).

N$^1$-Spermine-L-serinyl amide (1187)-$^1$H NMR(D$_2$, δ): 4.13 (t, 1H), 4.00 (m, 2H), 3.36 (t, 2H), 3.12 (m, 10H), 2.13 (m, 2H), 2.09 (m, 2H), 1.93 (m, 4H). $^{13}$C NMR (D$_2$O,ppm): 168.7, 61.0, 55.4, 47.9, 47.8, 46.0, 45.4, 37.5, 37.4, 36.4, 24.6, 23.7 (2C).

N$^1$-Spermine-L-threoninyl amide (1207)-$^1$H NMR (D$_2$O, δ): 4.04 (m, 1H), 3.72 (m, 2H), 3.23 (t, 2H), 2.97 (m, 12H), 1.96 (m, 2H), 1.81 (m, 2H), 1.65 (m, 4H), 1.16 (m, 3H). $^{13}$C NMR (D$_2$O, ppm): 169.8, 67.2, 58.4, 57.7, 47.4, 46.3, 45.4, 37.6, 37.5, 37.1, 25.3, 24.2 (2C), 20.1.

N$^1$-Spermine-L-ornithyl amide (1224)-$^1$H NMR (D$_2$O, δ): 4.04 (t, 1H), 3.38 (m, 2H), 3.12 (m, 14H), 2.11 (m, 2H), 1.96 (m, 4H), 1.80 (m, 6H). $^{13}$C NMR (D$_2$O, ppm): 170.0, 53.6, 47.8, 47.7, 46.1, 45.4, 39.6, 37.4, 28.7, 26.3, 24.6, 23.7, 23.6, 23.4.

N$^1$-Spermine-L-lysinyl amide (1202)-$^1$H NMR (D$_2$O, δ): 4.09 (t, 1H), 3.39 (m, 2H), 3.17 (m, 14H), 2.16 (m, 2H), 1.99 (m, 4H), 1.85 (m, 4H), 1.51 (m, 2H). $^{13}$C NMR (D$_2$O, ppm): 173.2, 56.4, 50.3, 50.2, 48.5, 47.9, 42.4, 40.0, 39.8, 33.6, 29.6, 28.8, 27.1, 26.4 (2C), 24.7. MS (ESI$^+$):

N$^1$-Spermine-L-arginyl amide (1304)-$^1$H NMR (D$_2$O, δ): 4.04 (t, 1H), 3.38 (m, 2H), 3.12 (m, 14H), 2.11 (m, 2H), 1.96 (m, 4H), 1.80 (m, 6H).

N$^1$-Spermine-L-tryptophanyl amide (1095)-$^1$H NMR (D$_2$O, δ): 7.67 (d, 1H), 7.58 (d, 1H), 7.37 (s, 1H), 7.32 (t, 1H), 7.23 (t, 1H), 4.27 (t, 1H), 3.37 (m, 2H), 3.19 (m, 8H), 2.89 (t, 2H), 2.53 (m, 2H), 2.15 (m, 2H), 1.73 (m, 4H), 1.59 (m, 2H). $^{13}$C NMR (D$_2$O, ppm): 170.5, 136.6, 127.3, 126.0, 123.0, 120.2, 118.6, 112.7, 108.8, 54.6, 47.7, 47.4, 45.6, 45.5, 37.2, 37.1, 27.7, 25.4, 24.6, 23.9 (2C). MS (ESI$^+$): 389 (M+H).

N$^1$-Spermine-D-tryptophanyl amide (1309)-$^1$H NMR and $^{13}$C NMR were the same as above.

N$^1$-Spermine-L-phenylalanyl amide (1148)-$^1$H NMR (D$_2$O, δ): 7.46 (m, 5H), 4.28 (dd, 1H), 3.25 (m, 12H), 2.85 (t, 2H), 2.19 (m, 2H), 1.86 (m, 6H). $^{13}$C NMR (D$_2$O, ppm): 171.71, 136.66, 132.11, 131.84, 130.64, 83.75, 57.19, 49.70, 49.57, 47.68, 47.22, 39.51, 39.28, 39.00, 27.73, 26.40, 25.45.

N$^1$-Spermine-L-tyrosinyl amide (1173)-$^1$H NMR (D$_2$O, δ): 7.20 (d, 2H), 6.96 (d, 2H), 4.15 (t, 1H), 3.36 (m, 2H), 3.18 (m, 10H), 2.77 (t, 2H), 2.14 (m, 2H), 1.82 (m, 6H).

EXAMPLE XXXIII

Preparation of ORI 1202 and its thioamide analog, ORI 1380

Figure 47:
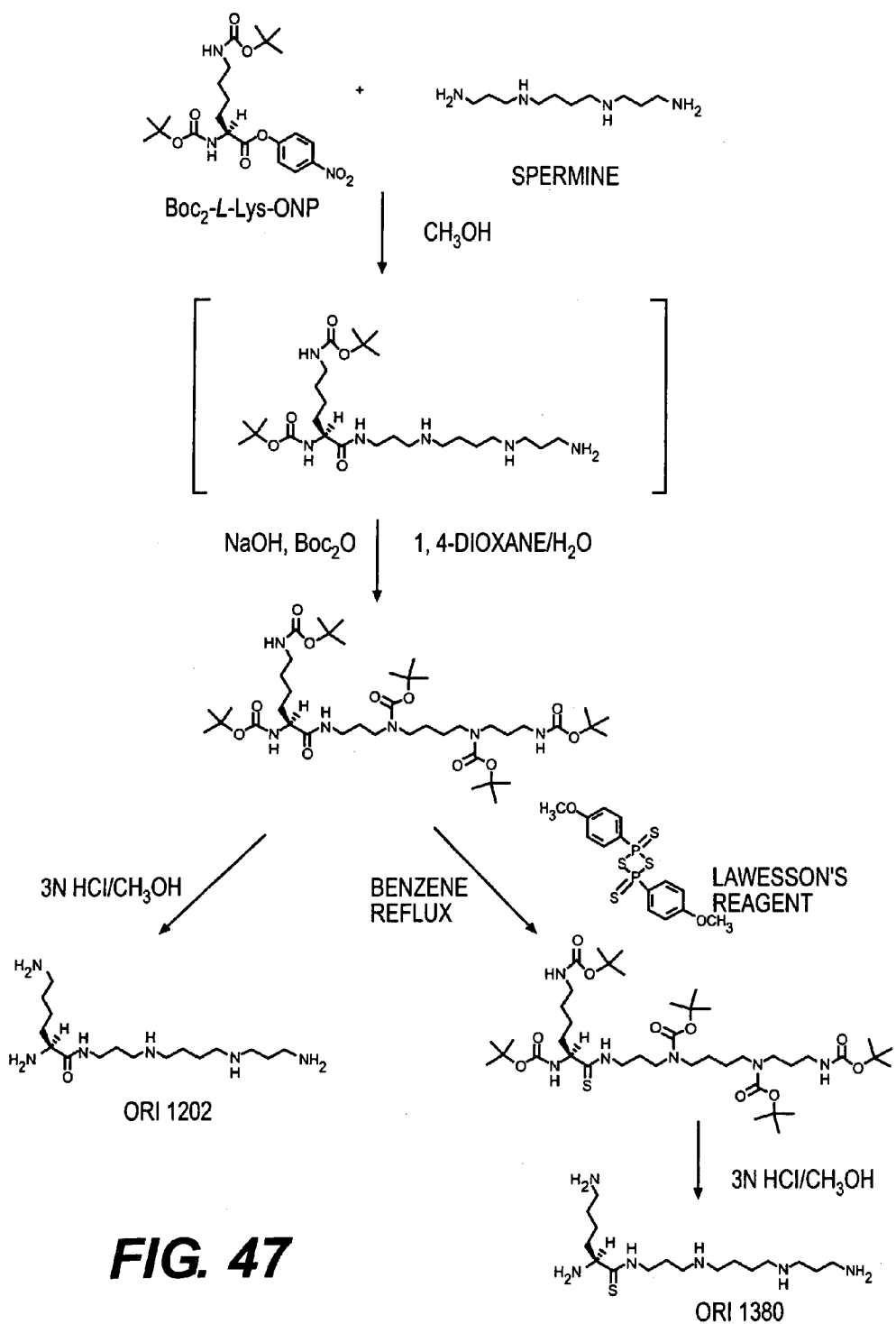
FIG. 47 shows a synthetic method for the production of compound 1202 and its thioamide derivative, compound 1380.

FIG. 47 represents a exemplary synthetic method for the preparation of ORI 1202 (L-Lys-Spm conjugate) and its metabolically stable thioamide derivative ORI 1380. The method may be used to produce the compounds on a multigram scale. The method utilizes tBoc protecting groups to produce an intermediate that is sufficiently lipophilic to be purified by silica gel chromatography, thus eliminating the less efficient ion exchange chromatography used in other synthetic routes.

Spermine is covalently coupled to the N-di-tBoc protected p-nitrophenyl active ester of L-lysine. After dropwise addition of a methanol solution of the active ester to a methanol solution of spermine, the yellow-colored crude reaction solution containing a mixture of un-, mono-, and di-substituted spermine derivatives is evaporated in vacuo. To the homogenous solution produced from this crude oil and a 3:1 mixture of 1,4-dioxane and water is added a solution containing five equivalents of di-tert-butoxydicarbonate in 1,4-dioxane. The resulting mixture is periodically adjusted to pH 11 by the addition of 1N NaOH.

After stirring for 18 hours, most of the 1,4-dioxane is removed in vacuo and the resulting heterogenous mixture is dissolved in a mixture of water and ethyl acetate. After removal of the organic layer, the aqueous layer is extracted 3 additional times with additional portions of ethyl acetate. The combined organic layers are washed with brine, dried with MgSO$_4$ and evaporated. This crude reaction product was purified by chromatography over silica gel using stepwise elution with 1:1 ethyl acetate/hexane containing 0%, 2%, 3% and then finally 4% methanol. The order of elution is tBoc$_4$-spermine (25% yield), the desired $^t$Boc$_2$-L-Lys-$^t$Boc$_2$ (52% yield) and finally the $^t$Boc$_2$-L-Lys-spermine ($^t$Boc)$_2$ (18% yield) disubstituted side product.

The resultant, fully $^t$Boc-protected intermediate can be directly deprotected using 3N HCl in methanol to give the 5HCl salt of ORI1202 at 98% yield. Alternatively, this intermediate can be refluxed in benzene with Lawesson's reagent for 3 hours to yield the penta-tBoc protected metabolically stable thioamide analog of ORI1202 (ORI1380). Following purification by chromatography over silica gel using 8:2 and then 1:1 hexane/ethyl acetate, the desired protected thioamide analog is produced at 52% yield. This material is then deprotected in quantitative yield using 3N HCl in methanol.

EXAMPLE XXXIV

Characterization of a preferred polyamine analogue: compound 1202

In the course of identifying optimal polyamine transport inhibitors, compound 1202 was selected for detailed studies because of its desirable transport and growth inhibition properties. Compound 1202 is soluble in water at ≧100 mM, pH 7.0. It is stable at 37° C. in water and cell culture media with FBS and AG for at least six days, as determined by HPLC analysis.

Compound 1202 was tested for its ability to inhibit $^3$H-putrescine ($^3$H-PUT), $^3$H-spermidine ($^3$H-SPD), and $^{14}$C-spermine ($^{14}$C—SPM) uptake in MDA human breast carcinoma cells. 300 nM 1202 was the maximum concentration tested in initial rate transport assays. Concentrations of 1202 and labeled polyamine substrates were varied over a 4 log concentration range in order to obtain actual $K_i$ values. Table 3 below shows the obtained inhibition constants as well as the standard deviation of the values. Compound 1202 competitively inhibited uptake of putrescine, spermidine and spermine.

TABLE 3

Inhibition constants ($K_i$ values) with 1202 on MDA cells. Multiple concentrations of substrate and 1202 were used to determine $K_i$ values in a 15 min initial rate transport assay.

| Substrate | 1202 $K_i$ | Characterization |
| --- | --- | --- |
| $^3$H-Putrescine | 28 ± 9 nM | Competitive |
| $^3$H-Spermidine | 32 ± 15 nM | Competitive |
| $^{14}$C-Spermine | 83 ± 15 nM | Competitive |

EXAMPLE XXXV

1202 Mediated Polyamine Transport Inhibition and Lack of Cellular Accumulation

Figure 48:
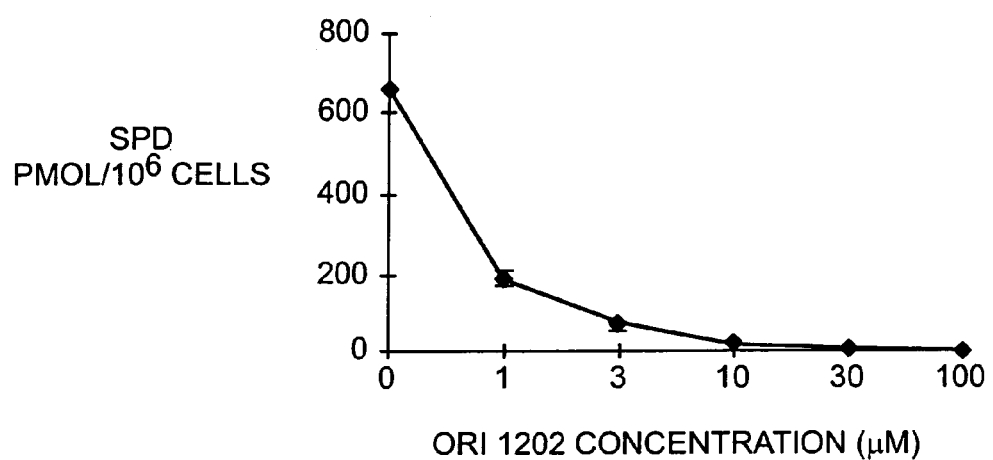
FIG. 48 shows accumulation of spermidine in cells treated with compound 1202.

Compound 1202 was assayed for its ability to inhibit cellular accumulation of [3H]SPD over 20 h (FIG. 48). At 1 µM, 1202 inhibited SPD uptake to 28% of the levels in untreated cells. At 30 and 100 µM 1202, the concentrations that show maximal growth inhibition (see below), only 1.5% (10.1±1.2 pmol SPD/10$^6$ cells) and 1.1% (7.0±0.9 pmol SPD/10$^6$ cells), respectively, of SPD levels remains in untreated cells (660 pmol SPD/10$^6$ cells). Compound 1202 effectively prevents the uptake of SPD by MDA cells. In the presence of all concentrations of 1202 tested, cells were greater than 90% viable at 20 h.

Figure 49A:
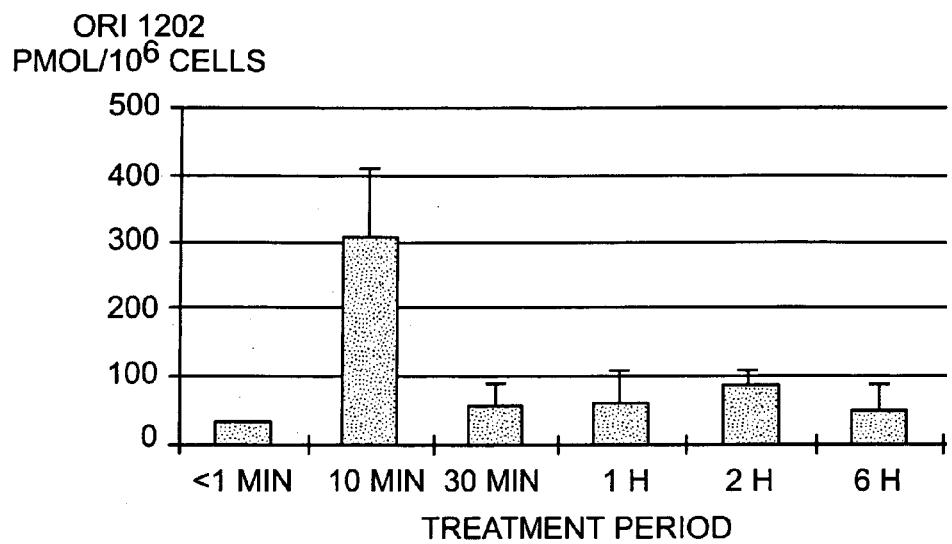
FIG. 49 shows accumulation of polyamines and compound 1202 in cells over time.
Figure 49B:
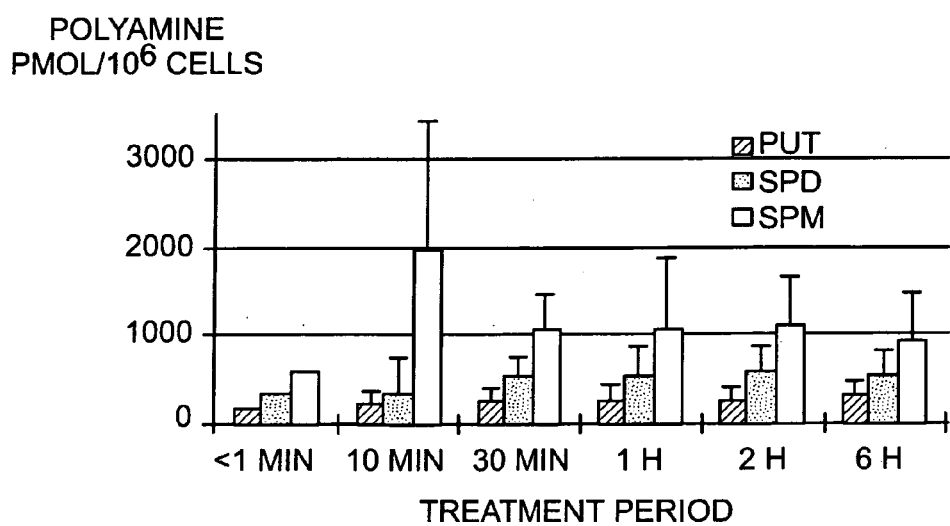

In order to determine if 1202 was a substrate for the polyamine transport system, we determined the steady-state level of 1202 in MDA cells over 6 h. MDA cells were incubated with 1202 (30 µM) and 1 mM AG for varying lengths of time, from less than 1 min (background) to 6 h (FIG. 49). At 10 min, there was a 9 fold increase in 1202 levels associated with the cell lysates and a 3 fold increase in SPM levels compared to background levels. The levels of 1202 and the three polyamines were essentially unchanged between 30 min and 6 h, stabilizing at levels only 30–50% greater than initial cellular levels. Since incubation with 30 µM 1202 resulted in only ~50 pmoles of detectable 1202 per million cells between 0.5–6 h, the reproducible increases in 1202 (9×) and SPM (3×) at 10 min suggests that there may be some initial uptake and degradation that is subsequently inhibited, or an equilibrium with SPM breakdown or export was reached.

EXAMPLE XXXVI

Delayed Transport Recovery and Growth Inhibition and Rescue

Figure 50:
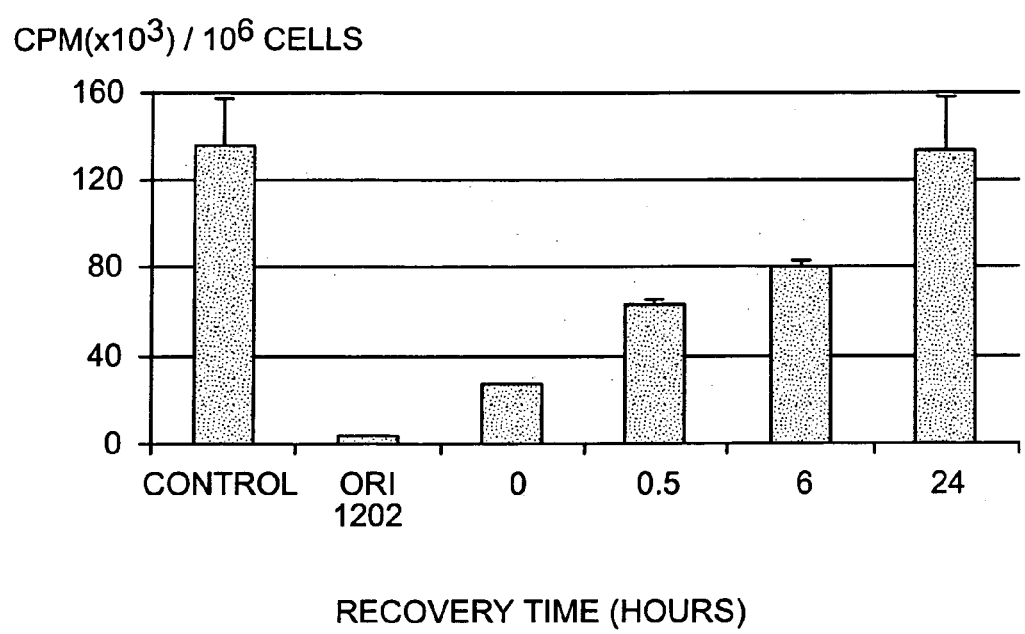
FIG. 50 shows recovery of spermidine transport in cells treated with compound 1202.

A 3 day incubation with DFMO resulted in maximum 3 fold up-regulation of SPD transport in MDA cells (data not shown). With 100 µM 1202 present during the 15 min transport assay, SPD transport was inhibited by 98% (FIG. 50). An advantage of this transport inhibitor is that normal transport activity is inhibited for several hours after the compound has been washed out of cell cultures. After 1 h treatment with 1202, AG, and DFMO, followed by washing, transport was 19% of control immediately, and 47% and 60% of control at 0.5 h and 6 h, respectively. Transport was equivalent to untreated cells by 24 h after washing.

Figure 51:
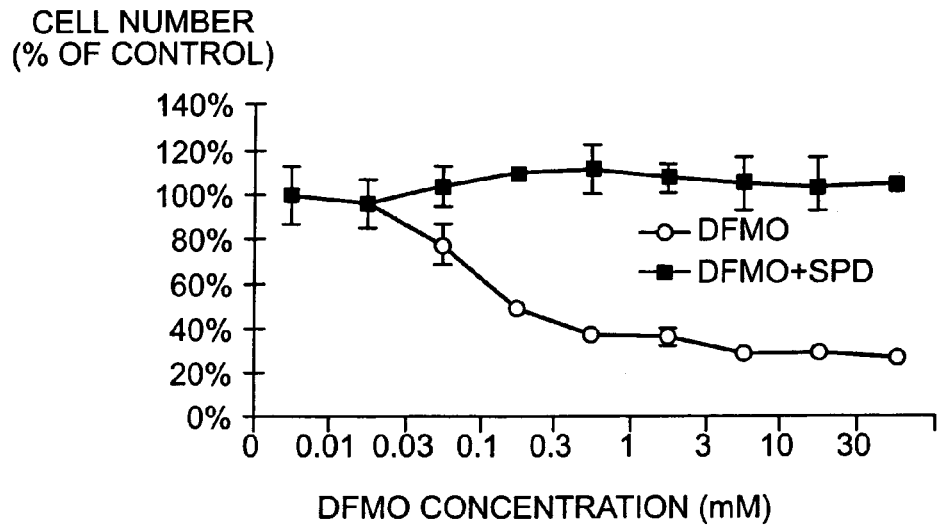
FIG. 51 shows growth inhibition and rescue of cells treated with DFMO.
Figure 52:
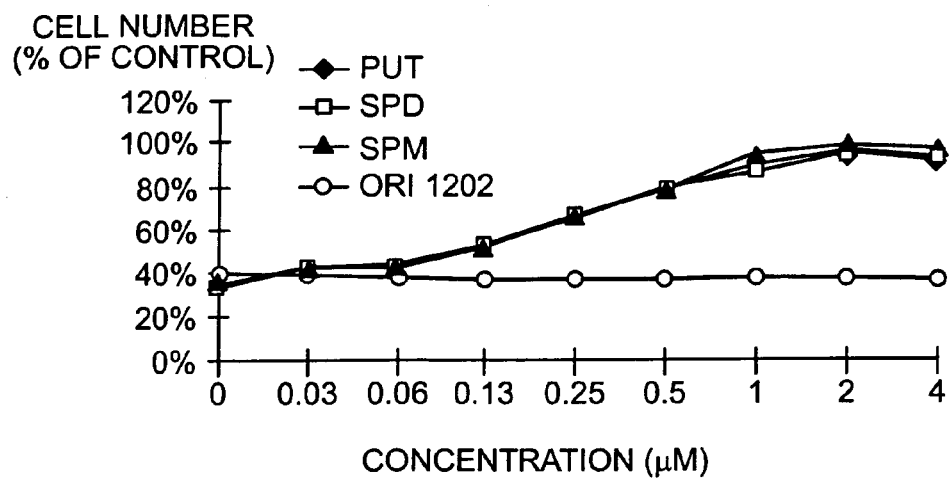
FIG. 52 shows rescue of cells from DFMO induced growth inhibition.

Compound 1202 was selected because of its growth inhibitory properties when used with the polyamine synthesis inhibitor, DFMO. Growth assays were done over a six day period in order to allow for polyamine depletion within cells. When synthesis of polyamines is inhibited, cells compensate by increasing transport of extracellular polyamines into the cell. Over the time course of the assay, polyamines in the culture media may be depleted resulting in growth inhibition. MDA cells grown for six days with DFMO and no added SPD showed dose dependent growth inhibition (FIG. 51). This is probably due to depletion of external polyamines, since the cells were rescued from growth inhibition by the addition of 1 µM SPD and 1 mM AG to the culture media Similar concentrations of PUT, SPD, and SPM rescued MDA breast carcinoma cells from DFMO-induced growth inhibition in a dose dependent manner (FIG. 52). DFMO (230 µM) caused a reduction in MDA cell number to 35% of control when no additional polyamines were added to the culture media of the six day growth assay. As little as 0.03 µM of any of the polyamines showed a slight rescue and increased cell number to 42% of control cultures. Polyamines at 0.5 µM raised cell number to 80% of control cultures. A similar rescue was demonstrated with the addition of acetylated SPD or acetylated SPM (data not shown). We assayed for the effect on growth when cells were grown with compound 1202, rather than added natural polyamines. 1202, up to 30 µM (data not shown), does not rescue the cells from DFMO induced-growth inhibition, suggesting that 1202 does not enter the cells, or if it does get in, it cannot substitute for normal polyamines in growth functions.

EXAMPLE XXXVII

Growth Inhibition with 1202 and DFMO

Figure 53:
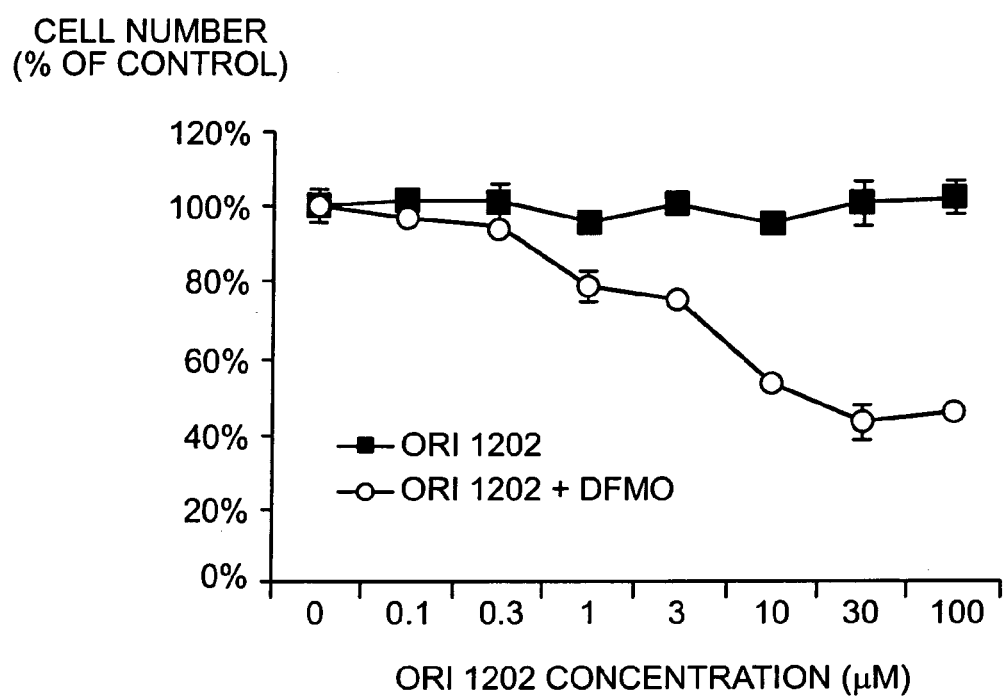
FIG. 53 shows growth inhibition of cells treated with compound 1202 and DFMO.

The combined effect of the polyamine synthesis inhibitor DFMO and the transport inhibitor 1202 on the growth of MDA breast carcinoma cells is shown in FIG. 53. In the presence of 1 µM SPD, the effect of 1202 alone or DFMO alone was minimal. However, the combination of 1202 with DFMO synergistically inhibited cell growth. With 230 µM DFMO, the growth inhibition with 1202 was dose dependent, with 30 µM giving maximum growth inhibition and >90% viability. At higher 1202 concentrations, a plateau appears at approximately 40–45% of control cell number and cells maintain >90% viability.

Figure 54:
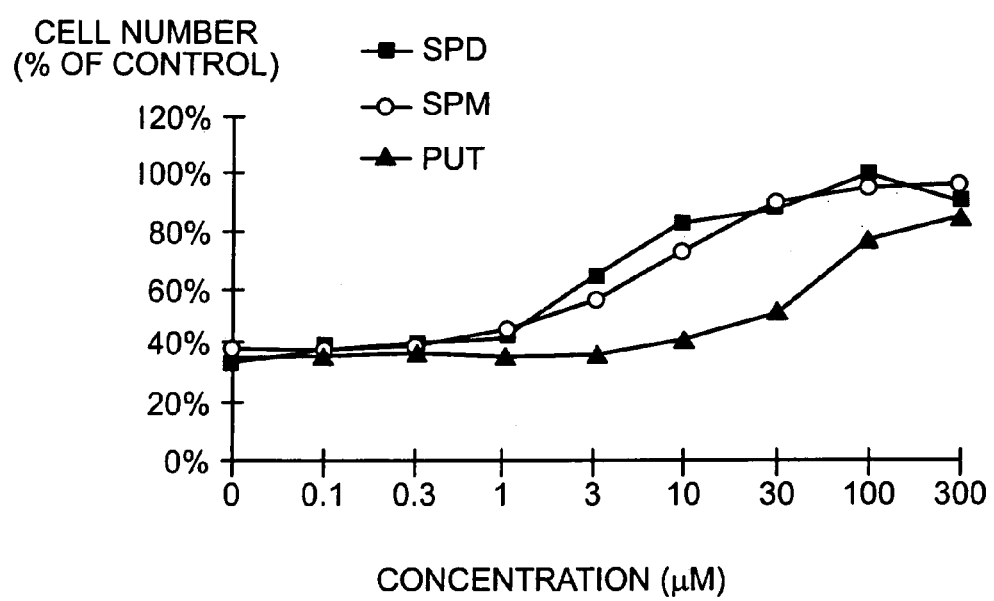
FIG. 54 shows rescue of cells from growth inhibition.

Because 1202 is an inhibitor of the polyamine transport system, we determined the concentrations of PUT, SPD, and SPM that were required as additions to the culture media to rescue cells from growth inhibition due to 1202 and DFMO. SPD and SPM both began to reverse growth inhibition at 1 µM, whereas greater than 10 µM PUT was required for the same degree of rescue (FIG. 54). The greater levels of PUT that were required would be expected based on the lower $K_i$ of 1202 against PUT (see Table 3 above).

The ability of the combined inhibition of polyamine synthesis and transport to induce growth inhibition was tested in multiple cell lines. For each cell line tested, a DFMO titration curve, without addition of SPD, was used to determine the optimal inhibitory concentration of DFMO. In our six day growth assays, 1202 was tested at increasing concentrations with the optimal concentration of DFMO. 1 µM SPD was included to ensure that growth inhibition reflected inhibition of transport. 1202 with DFMO inhibited growth of multiple tumor cell lines in culture.

Most $IC_{50}$ values were in the low micromolar range (Table 4 below) and 1202 inhibited cell growth synergistically with DFMO. The exceptions were the two non-small cell lung carcinoma cell lines. Their growth responses may reflect cell line or tissue specific differences in transport or metabolism

TABLE 4

Growth inhibition by polyamine depletion in multiple tumor types. 1202 $IC_{50}$ values were determined in a 6 day growth assay with the optimal DFMO concentration for each cell line.

| Tumor type | Cell Line | Cmpd 1202 + DFMO $IC_{50}$ (µM) | DFMO Conc. (mM) |
|---|---|---|---|
| Breast carcinoma | MDA-MB-231 | 4.8 | 0.23 |
| Prostate carcinoma | PC-3 | 5.3 | 1.0 |
|  | DU 145 | 5.0 | 1.0 |
|  | LNCaP | 2.6 | 5.0 |
| Bladder carcinoma | T-24 | 1.6 | 5.0 |
| Lung carcinoma (non-small cell) | NCI H157 | 140 | 0.23 |
|  | NCI H226 | >300 | 3.0 |

EXAMPLE XXXVIII

Long Term Treatment Affects Growth Rate and Intracellular Polyamine Levels

Figure 55:
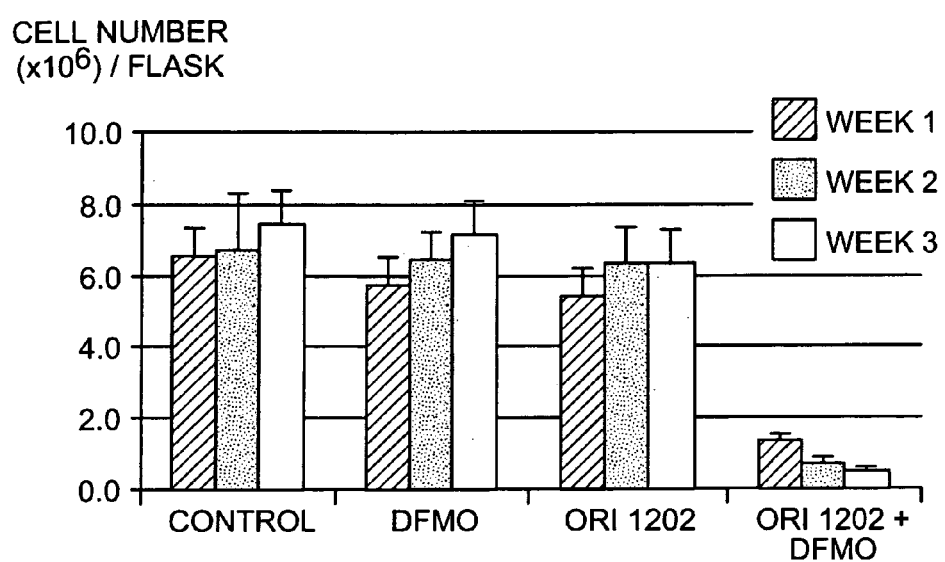
FIG. 55 shows cell growth over time after treatment with compound 1202, DFMO, or both.

It was predicted that growth inhibition after incubation with the combination of a polyamine synthesis and transport inhibitor would be due to a decrease in intracellular polyamine levels. We examined the intracellular polyamine levels in MDA cells after 6 and 20 days of growth in the presence of polyamine synthesis inhibitor or transport inhibitor, or both. Changes in the rates of cell growth, reflected in total cell number in the cultures at the time of passage over three weeks, are shown in FIG. 55.

MDA cells cultured in DFMO (500 µM) or 1202 (60 µM) alone showed little difference in growth rate as determined by weekly cell counts over the three week studies. However, MDA cells grown in the presence of both 60 µM 1202 and 500 µM DFMO showed decreasing rates of growth with time: 79%, 89% and 93% fewer cells after one, two and three weeks of treatment, respectively. Even after three weeks with dual compound treatment, cells were greater than 90% viable, as determined by trypan blue exclusion.

Figure 56:
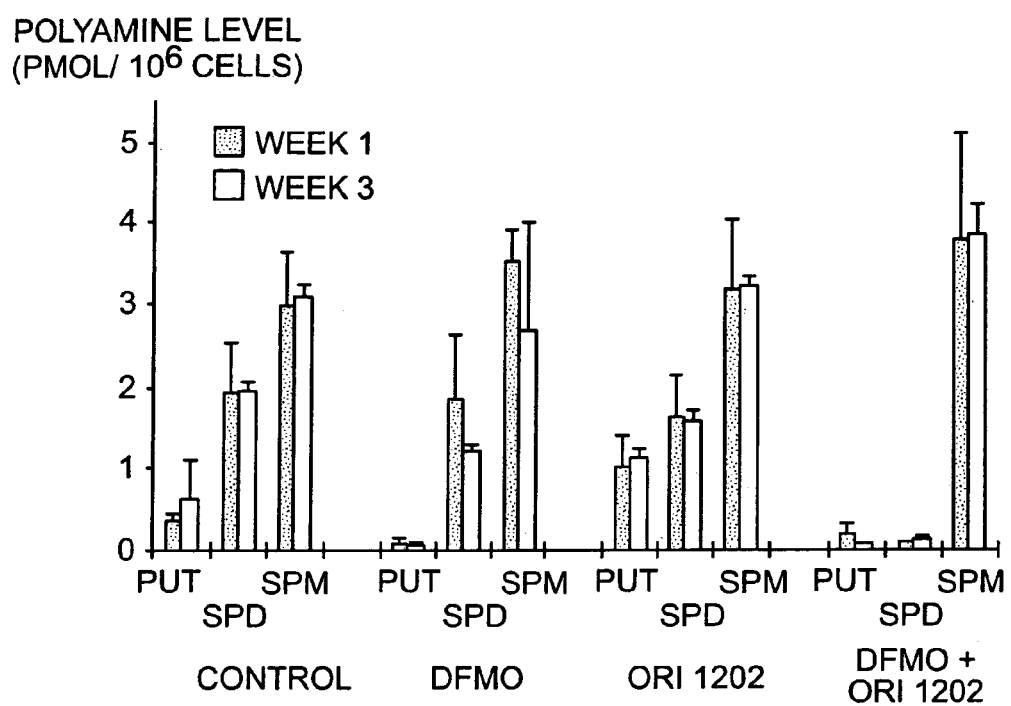
FIG. 56 shows cellular polyamine levels after treatment with compound 1202, DFMO, or both.

In order to correlate growth with polyamine levels, polyamine levels were analyzed after one and three weeks of drug treatment (FIG. 56). There were no significant changes in SPM levels over the three week period with any of the treatments. With single compound treatment, the most striking differences were in PUT levels compared to control cultures. Polyamine synthesis inhibition with DFMO resulted in a 69–86% decrease in PUT levels. In contrast, after treatment with 1202, PUT levels increased 1.8 to 3.0 fold (approx. 1.10 nmol/$10^6$ cells), compared to control cultures. These intracellular polyamine changes were not reflected in cell growth changes from control cells Treatment with both 1202 and DFMO did have an effect on cell growth and caused the greatest changes in intracellular polyamine levels. PUT was reduced to levels similar to those seen with DFMO treatment alone (0.20 and 0.07 nmol/$10^6$ cells, weeks 1 and 3, respectively). In addition, SPD levels were reduced by approximately 95% (0.06 and 0.13 nmol/$10^6$ cells, weeks 1 and 3, respectively) compared to control cultures.

EXAMPLE XXXIX

Transport Characteristics after Treatment

Figure 57A:
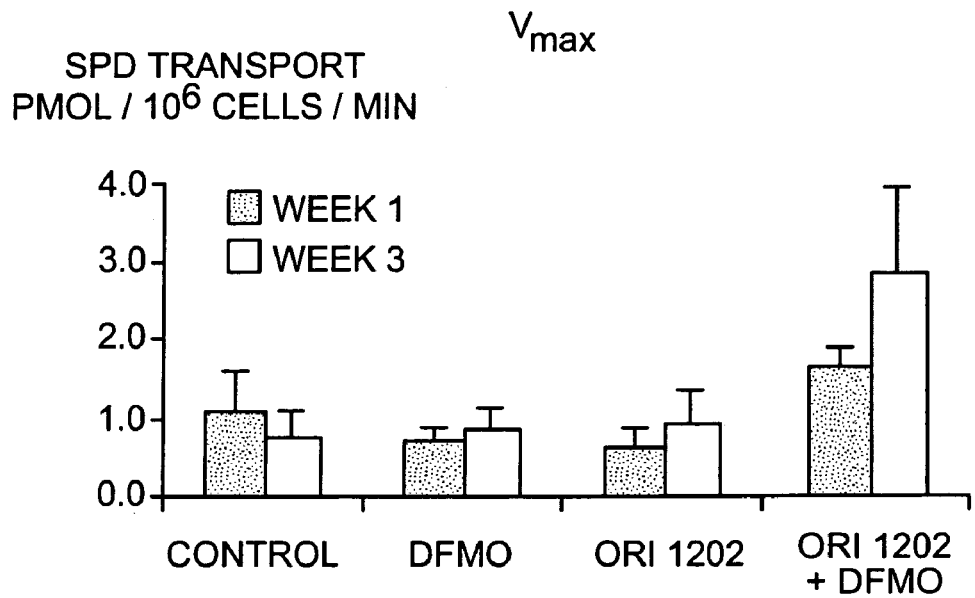
FIG. 57, panels A and B, shows spermidine transport in cells after treatment with compound 1202, DFMO or both.
Figure 57B:
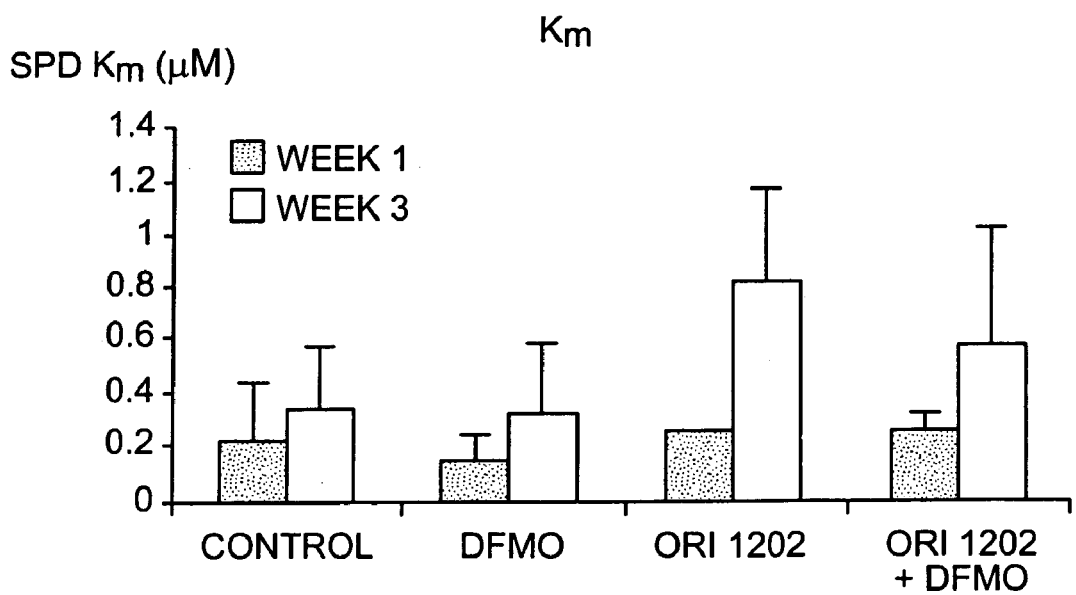

Treating cells with DFMO for 24 h has been shown to increase the $V_{max}$ of polyamine transport without changing the $K_m$. We wished to determine the effects of long term treatment with DFMO, 1202, or both, on polyamine transport characteristics. The MDA cell cultures that were analyzed for growth and intracellular polyamine levels, were also assayed for changes in transport $K_m$ and $V_{max}$ with $^3$H—SPD after approx. 1.5 and 3.5 weeks of treatment (FIG. 57). The most striking changes were the increases in $V_{max}$ for SPD after dual compound treatment: approximately 1.5 and 3.3 fold increases at 1.5 and 3.5 weeks, respectively. There was no change in $V_{max}$ after treatment with DFMO in the presence of SPD. There was considerable variation in $K_m$ between experiments but there appeared to be increases in $K_m$ after treatment with 1202 alone and in conjunction with DFMO, especially after 3.5 weeks. These results suggest that there have been significant changes in the activity, conformation, or structure of the polyamine transport system after prolonged dual compound treatment.

All references cited herein are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features herein before set forth as follows in the scope of the appended claims.

What is claimed is:

1. A $N^1$-monosubstituted polyamine analogue or derivative represented by the formula

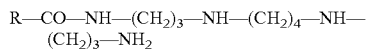

wherein R is selected from a D or L amino acid; D or L ornithine, an alicyclic, a single or multi-ring aromatic; aliphatic-substituted single or multi-ring aromatic; and a substituted or unsubstituted, single or multi-ring heterocyclic and wherein when R is a substituted single or multi-ring heterocyclic, heterocyclic is substituted with at least one member of the group consisting of: OH, halogen, $NO_2$, $NH_2$, $NH(CH_2)_nCH_3$, $N((CH_2)_nCH_3)_2$, CN, $(CH_2)_nCH_3$, $O(CH_2)_nCH_3$, $S(CH_2)_nCH_3$, $NHCO(CH_2)_nCH_3$, $O(CF_2)_nCF_3$, $COO(CH_2)_nCH_3$, wherein n is 0–10 and wherein said analogue or derivative does not have a formula represented by ID 1022, 1043, or 1202.

2. An analogue or derivative according to claim 1 wherein R is a D or L amino acid or D or L ornithine.

3. A composition comprising a polyamine analogue or derivative according to claim 1 or 2 and a pharmaceutically acceptable excipient.

4. A composition comprising a polyamine analogue or derivative according to claim 1, a pharmaceutically acceptable excipient, and an inhibitor of polyamine synthesis.

5. A composition according to claim 4 herein said inhibitor of polyamine synthesis is difluoromethylornithine (DFMO).

6. A method for treating a disease or a condition in a subject associated with undesired cell proliferation and/or which is treatable by inhibition of polyamine transport, comprising administering to said subject a polyamine analogue or derivative according to claim 1.

7. A method according to claim 6 wherein said undesired cell proliferation is associated with proliferation of cells of the immune system, cells of the vascular neontima, tumor cells or with undesired angiogenesis.

8. A method according to claim 6 wherein said disease or condition is cancer or post-angioplasty injury.

9. A method according to claim 6 further comprising administration of an inhibitor of polyamine synthesis.

10. A method according to claim 9 wherein said inhibitor of polyamine systhesis is difluoromethylornithine (DFMO).

11. A composition according to claim 4 or 5 in solid form.

12. A composition according to claim 4 or 5 in liquid form.

13. A method according to any one of claims 6–10 wherein said administering is performed orally, parenterally, topically, transdermally, intravaginally, intranasally, intrabronchially, intracranially, intraocularly, intraaurally, or rectally, or by injection.

14. A method according to claim 13 wherein said administering by injection is intravenous, subcutaneous, intramuscular, intracranial, or intraperitoneal.

15. The analogue or derivative of claim 1, wherein said substituted or unsubstituted heterocyclic is a pyrrolidine or a substituted pyrrolidine.

16. The analogue or derivative of claim 15, wherein said substituted pyrrolidine is a N-substituted pyrrolidine.

17. The analogue or derivative of claim 16 represented by the formula ID 1158.

18. The analogue or derivative of claim 1 represented by the formula ID 1224.

19. A method according to claim 6 wherein said condition is associated with cancer.

* * * * *